(12) United States Patent
Stadtmueller

(10) Patent No.: US 8,889,684 B2
(45) Date of Patent: Nov. 18, 2014

(54) AZAINDOLYLPHENYL SULFONAMIDES AS SERINE/THREONINE KINASE INHIBITORS

(75) Inventor: Heinz Stadtmueller, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 125 days.

(21) Appl. No.: 13/359,555

(22) Filed: Jan. 27, 2012

(65) Prior Publication Data

US 2013/0029993 A1    Jan. 31, 2013

(30) Foreign Application Priority Data

Feb. 2, 2011 (EP) ..................................... 11153087
Sep. 14, 2011 (EP) ..................................... 11181258

(51) Int. Cl.

| C07D 487/04 | (2006.01) |
|---|---|
| C07D 471/04 | (2006.01) |
| A61K 31/519 | (2006.01) |
| A61K 31/496 | (2006.01) |
| A61K 31/4985 | (2006.01) |
| A61K 31/506 | (2006.01) |
| A61P 35/00 | (2006.01) |

(52) U.S. Cl.
CPC ............ C07D 471/04 (2013.01); C07D 487/04 (2013.01)
USPC . 514/249; 514/256; 514/253.04; 514/252.16; 514/265.1; 546/113; 544/350; 544/280; 544/333

(58) Field of Classification Search
CPC .......................... C07D 487/04; C07D 471/04
USPC ............ 544/295, 333; 546/113; 514/300, 256
See application file for complete search history.

(56) References Cited

U.S. PATENT DOCUMENTS

| 7,166,628 B2 | 1/2007 | Cogan et al. |
|---|---|---|
| 7,214,802 B2 | 5/2007 | Cogan et al. |
| 7,485,657 B2 | 2/2009 | Cogan et al. |
| 7,511,042 B2 | 3/2009 | Cogan et al. |
| 7,514,458 B2 | 4/2009 | Cogan et al. |
| 7,531,560 B2 | 5/2009 | Cogan et al. |
| 7,569,568 B2 | 8/2009 | Cogan et al. |
| 7,858,804 B2 | 12/2010 | Frutos et al. |
| 8,198,308 B2 | 6/2012 | Steurer et al. |
| 2004/0102492 A1 | 5/2004 | Cogan et al. |
| 2005/0153972 A1 | 7/2005 | Cogan et al. |
| 2005/0256113 A1 | 11/2005 | Cogan et al. |
| 2006/0079519 A1 | 4/2006 | Cogan et al. |
| 2006/0100204 A1 | 5/2006 | Cogan et al. |
| 2007/0032492 A1 | 2/2007 | Cogan et al. |
| 2007/0142371 A1 | 6/2007 | Cogan et al. |
| 2008/0182837 A1 | 7/2008 | Steurer et al. |
| 2009/0127815 A1 | 5/2009 | Tani et al. |
| 2010/0240657 A1 | 9/2010 | Sapountzis et al. |
| 2011/0059938 A1 | 3/2011 | Steurer et al. |
| 2011/0183952 A1 | 7/2011 | Sapountzis et al. |

FOREIGN PATENT DOCUMENTS

| WO | 2008003770 A1 | 1/2008 |
|---|---|---|
| WO | 2009003998 A2 | 1/2009 |
| WO | 2009003999 A2 | 1/2009 |
| WO | 2009012283 A1 | 1/2009 |
| WO | 2010034838 A2 | 4/2010 |
| WO | 2010042337 A1 | 4/2010 |
| WO | 2011117381 A1 | 9/2011 |
| WO | 2012085126 A1 | 6/2012 |
| WO | 2012085127 A1 | 6/2012 |
| WO | 2012101238 A1 | 8/2012 |
| WO | 2012104388 A1 | 8/2012 |

OTHER PUBLICATIONS

International Search Report for PCT/EP2012/051796 mailed Apr. 16, 2012.

*Primary Examiner* — Susanna Moore
(74) *Attorney, Agent, or Firm* — Michael P. Morris; Anthony P. Bottino; Alan R. Stempel

(57) ABSTRACT

The present invention encompasses compounds of general formula (I)

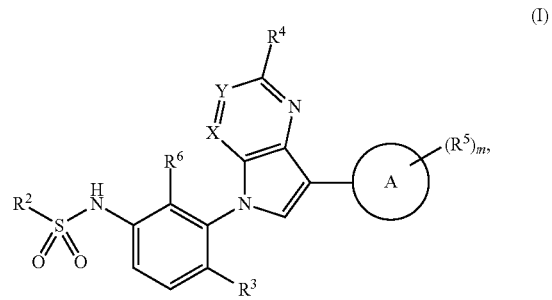

wherein the groups $R^2$ to $R^6$, A, X, Y and m are defined as in claim 1, which are suitable for the treatment of diseases characterized by excessive or abnormal cell proliferation, pharmaceutical preparations which contain compounds of this kind and their use as medicaments.

34 Claims, No Drawings

AZAINDOLYLPHENYL SULFONAMIDES AS SERINE/THREONINE KINASE INHIBITORS

The present invention relates to new azaindolylphenyl sulfonamides of general formula (I)

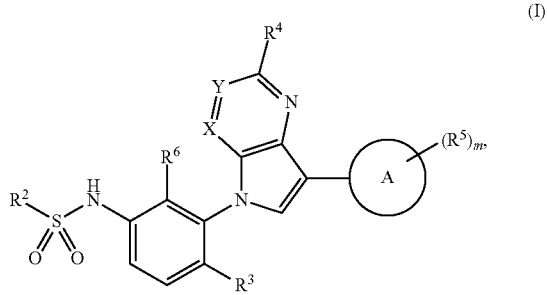

wherein the groups $R^2$ to $R^6$, A, X, Y and m have the meanings given in the claims and specification, pharmaceutical preparations which contain compounds of this kind and their use as medicaments.

BACKGROUND TO THE INVENTION

Various fluorine-substituted phenyl sulfonamides are described in WO 2009/012283 as modulators of various kinases.

The aim of the present invention is to indicate new azaindolylphenyl sulfonamides which may be used for the prevention and/or treatment of diseases characterised by excessive or abnormal cell proliferation. The azaindolylphenyl sulfonamides according to the invention are distinguished by their great inhibitory effect on B-Raf V600E and their improved high potency against tumour cells, e.g. melanoma cells, which is achieved by the selective inhibition of B-Raf V600E and can also be demonstrated in vivo. Apart from the inhibitory effect and the cell potency the compounds additionally have good pharmacokinetic properties. As a result of this overall profile, the compounds according to the invention are suitable for the development of a drug.

The RAS-RAF-MAPK (mitogen-activated protein kinase) signaling pathway plays a critical role in transmitting proliferation signals generated by the cell surface receptors and cytoplasmic signaling elements to the nucleus. Constitutive activation of this pathway is involved in malignant transformation by several oncogenes. Activating mutations in RAS occur in approximately 15% of cancers, and recent data has shown that B-RAF is mutated in about 7% of cancers (Wellbrock et al., Nature Rev. Mol. Cell. Biol. 2004, 5:875-885), identifying it as another important oncogene in this pathway. In mammals, the RAF family of serine/threonine kinases comprises three members: A-RAF, B-RAF and C-RAF. However, activating mutations have so far been only identified in B-RAF underlining the importance of this isoform. It is believed that B-RAF is the main isoform that couples RAS to MEK, and that C-RAF and A-RAF signal to ERK only to fine-tune cellular responses (Wellbrock et al., Nature Rev. Mol. Cell. Biol. 2004, 5:875-885). The most common cancer mutation in B-RAF results in a valine to glutamic acid exchange at position 600 of the protein (V600E), which dramatically enhances B-RAF activity, presumably because its negative charge mimics activation loop phosphorylation (Wan et al., Cell 2004, 116: 855-867). The highest incidence of B-RAF V600 mutations occurs in malignant melanoma (38%), thyroid cancer (38%), colorectal cancer (10%), bilary tract cancer (12%) and ovarian cancer (12%), but they also occur at a low frequency in a wide variety of other cancers (frequencies of mutations according to COSMIC (*Catalogue Of Somatic Mutations In Cancer; Wellcome Trust Sanger Institute*) release v49, 29 Sep. 2010). Literature supported the hypothesis that B-RAF$^{V600E}$ mutated tumour cells seem to rely heavily on the continued activation of this pathway—a phenomenon termed "oncogene addiction"—whereas normal B-RAF$^{wt}$ cells use a broader range of signals. This provides an Achilles' heel that can be exploited therapeutically by treating patients with somatically mutated B-RAF$^{V600E}$ using orally available B-RAF inhibitors.

The key role of B-RAF$^{V600E}$ in aberrant ERK signaling and consequently oncogenesis has been demonstrated in several independent experimental approaches such as overexpression of oncogenic/mutated B-RAF in vitro and in vivo (Wan et al., Cell 2004, 116: 855-867; Wellbrock et al., Cancer Res. 2004, 64: 2338-2342), siRNA knock-down in vitro (Karasarides et al., Oncogene 2004, 23: 6292-6298) or in inducible short-hairpin RNA xenograft models where gain-of-function B-RAF signaling was found to be strongly associated with in vivo tumorigenicity (Hoeflich et al., Cancer Res. 2006, 66: 999-1006).

Treatment of B-RAF$^{V600E}$ mutated melanoma or colon carcinoma cells induces a B-RAF inhibition phenotype (e.g. reduction of phospho-MEK and phospho-ERK levels, reduction of cyclin D expression and induction of p27 expression). Consequently, these cells are locked in the G1-phase of the cell cycle and do not proliferate.

DETAILED DESCRIPTION OF THE INVENTION

It has now been found that, surprisingly, compounds of general formula (I) wherein the groups $R^2$ to $R^6$, A, X, Y and m have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (I)

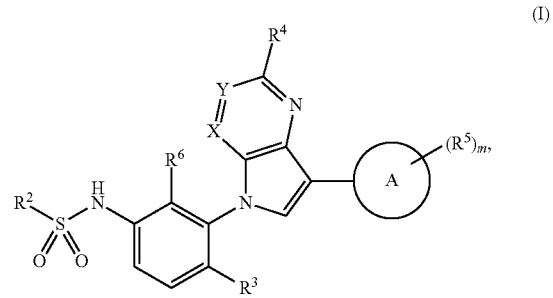

wherein (A0)

$R^2$ is a group optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl or $R^2$ is $-NR^{c1}R^{c1}$;
  each $R^{b1}$ is independently selected from among $-OR^{c1}$, $-NR^{c1}R^{c1}$, halogen, $-CN$, $-O(O)R^{c1}$, $-O(O)OR^{c1}$, $-C(O)NR^{c1}R^{c1}$, $-S(O)_2R^{c1}$, $-S(O)_2NR^{c1}R^{c1}$, $-NHC(O)R^{c1}$ and $-N(C_{1-4}alkyl)C(O)R^{c1}$ as well as the bivalent substituent $=O$, wherein the latter may only be a substituent in non-aromatic ring systems;
  each $R^{c1}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;
(B0)
  $R^3$ is selected from among hydrogen, halogen, $C_{1-4}$alkyl, $C_{1-4}$alkyloxy, $C_{2-4}$alkenyl, $C_{2-4}$alkynyl, $C_{1-4}$haloalkyl, $-CN$, $-NH(C_{1-4}alkyl)$ and $-N(C_{1-4}alkyl)_2$;
(F0)
  $R^4$ denotes hydrogen or a group optionally substituted by one or more, identical or different $R^{a2}$ and/or $R^{b2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-11 membered heterocyclyl, or is selected from among $-OR^{a3}$, $-NR^{a3}R^{a3}$, $-N(OR^{a3})R^{a3}$, halogen, $-CN$, $-C(O)R^{a3}$, $-C(O)OR^{a3}$, $-C(O)NR^{a3}R^{a3}$, $-C(NH)NR^{a3}R^{a3}$, $-S(O)_2NR^{a3}R^{a3}$, $-NHS(O)_2R^{a3}$, $-N(C_{1-4}alkyl)S(O)_2R^{a3}$, $-NHS(O)_2NR^{a3}R^{a3}$, $-NHC(O)R^{a3}$, $-N(C_{1-4}alkyl)C(O)R^{a3}$, $-NHC(O)OR^{a3}$, $-N(C_{1-4}alkyl)C(O)OR^{a3}$, $NHC(O)NR^{a3}R^{a3}$ and $-N(C_{1-4}alkyl)C(O)NR^{a3}R^{a3}$;
    each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
    each $R^{b2}$ is independently selected from among $-OR^{c2}$, $-NR^{c2}R^{c2}$, halogen, $-C(O)R^{c2}$, $-C(O)OR^{c2}$, $-C(O)NR^{c2}R^{c2}$, $-CN$, $-NHC(O)R^{c2}$ and $-NHC(O)OR^{c2}$;
    each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and $-C(O)-C_{1-6}$alkyl;
    each $R^{a3}$ independently of one another denotes hydrogen or a group optionally substituted by one or more, identical or different $R^{b3}$ and/or $R^{c3}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
    each $R^{b3}$ is independently selected from among $-OR^{c3}$, $-NR^{c3}R^{c3}$, halogen, $-C(O)R^{c3}$, $-C(O)OR^{c3}$, $-C(O)NR^{c3}R^{c3}$, $-CN$, $-NHC(O)R^{c3}$ and $-NHC(O)OR^{c3}$;
    each $R^{c3}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O-$C_{1-6}$alkyl, $(C_{1-4}alkyl)HN-C_{1-6}$alkyl, $(C_{1-4}alkyl)_2N-C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl;
(C0)
  ring A is a 5-10 membered heteroaryl;
(D0)
  m denotes the number 0, 1 or 2;

each $R^5$ independently of one another denotes a group optionally substituted by one or more, identical or different $R^{a4}$ and/or $R^{b4}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-11 membered heterocyclyl, or is independently selected from among $-OR^{a5}$, $-NR^{a5}R^{a5}$, $-N(OR^{a5})R^{a5}$, halogen, $-CN$, $-C(O)R^{a5}$, $-C(O)OR^{a5}$, $-C(O)NR^{a5}R^{a5}$, $-C(NH)NR^{a5}R^{a5}$, $-S(O)_2NR^{a5}R^{a5}$, $-NHS(O)_2R^{a5}$, $-N(C_{1-4}alkyl)S(O)_2R^{a5}$, $-NHS(O)_2NR^{a5}R^{a5}$, $-NHC(O)R^{a5}$, $-N(C_{1-4}alkyl)C(O)R^{a5}$, $-NHC(O)OR^{a5}$, $-N(C_{1-4}alkyl)C(O)OR^{a5}$, $-NHC(O)NR^{a5}R^{a5}$ and $N(C_{1-4}alkyl)C(O)NR^{a5}R^{a5}$;
    each $R^{a4}$ independently of one another denotes a group optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
    each $R^{b4}$ is independently selected from among $-OR^{c4}$, $-NR^{c4}R^{c4}$, halogen, $-C(O)R^{c4}$, $-C(O)OR^{c4}$, $-C(O)NR^{c4}R^{c4}$, $-CN$, $-NHC(O)R^{c4}$ and $-NHC(O)OR^{c4}$;
    each $R^{c4}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally is substituted by one or more, identical or different substituents selected from among halogen, $C_{1-6}$alkyl and $-C(O)-C_{1-6}$alkyl;
    each $R^{a5}$ independently of one another denotes hydrogen or a group optionally substituted by one or more, identical or different $R^{b5}$ and/or $R^{c5}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
    each $R^{b5}$ is independently selected from among $-OR^{c5}$, $-NR^{c5}R^{c5}$, halogen, $-C(O)R^{c5}$, $-C(O)OR^{c5}$, $-C(O)NR^{c5}R^{c5}$, $-CN$, $-NHC(O)R^{c5}$ and $-NHC(O)OR^{c5}$;
    each $R^{c5}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O-$C_{1-6}$alkyl, $(C_{1-4}alkyl)HN-C_{1-6}$alkyl, $(C_{1-4}alkyl)_2N-C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl;
(E0)
  X and Y are either both CH or one is CH and the other is CF or one is CH and the other is N;
(G0)
  $R^6$ is chlorine or fluorine;
wherein the compounds (I) may optionally also be present in the form of the tautomers, racemates, enantiomers, diastereomers and the mixtures thereof or as the respective salts of all the above-mentioned forms.

In one aspect (A1) the invention relates to compounds (I), wherein
  $R^2$ is selected from among $C_{1-6}$alkyl, 5-6 membered heteroaryl, $C_{3-6}$cycloalkyl and $C_{4-7}$cycloalkylalkyl.

In another aspect (A2) the invention relates to compounds (I), wherein
  $R^2$ denotes $C_{1-6}$alkyl.

In another aspect (A3) the invention relates to compounds (I), wherein
  $R^2$ is selected from among ethyl, n-propyl, iso-propyl and iso-butyl.

In another aspect (A4) the invention relates to compounds (I), wherein
$R^2$ is n-propyl.

In another aspect (A5) the invention relates to compounds (I), wherein
$R^2$ denotes cyclopropyl or cyclopropylmethyl.

In another aspect (A6) the invention relates to compounds (I), wherein
$R^2$ denotes furyl.

In another aspect (B1) the invention relates to compounds (I), wherein
$R^3$ is halogen.

In another aspect (B2) the invention relates to compounds (I), wherein
$R^3$ is fluorine.

In another aspect (C1) the invention relates to compounds (I), wherein
ring A is a nitrogen-containing 5-10 membered heteroaryl.

In another aspect (C2) the invention relates to compounds (I), wherein
ring A is a nitrogen-containing 5-6 membered heteroaryl.

In another aspect (C3) the invention relates to compounds (I), wherein
ring A is selected from among pyridyl and pyrimidyl.

In another aspect (C4) the invention relates to compounds (I), wherein
ring A is pyridyl.

In another aspect (C5) the invention relates to compounds (I), wherein
ring A is pyrimidyl.

In another aspect (D1) the invention relates to compounds (I), wherein
m is 0.

In another aspect (D2) the invention relates to compounds (I), wherein
m is 1.

In another aspect (CD1) the invention relates to compounds (I), wherein
m denotes 1;
$R^5$ and ring A together is

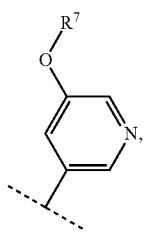

wherein
$R^7$ is $C_{1-6}$alkyl.

In another aspect (CD2) the invention relates to compounds (I), wherein
m denotes 1 and
$R^5$ and ring A together is

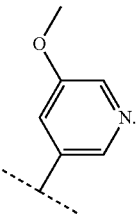

In another aspect (CD3) the invention relates to compounds (I), wherein
m denotes 0 and
ring A is

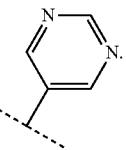

In another aspect (E1) the invention relates to compounds (I), wherein
X is CH and Y is CH.

In another aspect (E2) the invention relates to compounds (I), wherein
X is CH and Y is N.

In another aspect (E3) the invention relates to compounds (I), wherein
X is N and Y is CH.

In another aspect (E4) the invention relates to compounds (I), wherein
X is CH and Y is CF.

In another aspect (F1) the invention relates to compounds (I), wherein
$R^4$ is 3-11 membered heterocyclyl optionally substituted by one or more, identical or different $R^{a2}$ and/or $R^{b2}$;
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and
each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —$C(O)$—$C_{1-6}$alkyl.

In another aspect (F2) the invention relates to compounds (I), wherein
$R^4$ is 4-7 membered, nitrogen-containing heterocyclyl optionally substituted by one or more, identical or different $R^{a2}$ and/or $R^{b2}$;

each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —$C(O)$—$C_{1-6}$alkyl.

In another aspect (F3) the invention relates to compounds (I), wherein $R^4$ is selected from among piperazinyl, piperidinyl and morpholinyl, all optionally substituted by one or more, identical or different $R^{a2}$ and/or $R^{b2}$;

each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —$C(O)$—$C_{1-6}$alkyl.

In another aspect (F4) the invention relates to compounds (I), wherein $R^4$ is selected from among piperazinyl, piperidinyl and morpholinyl, all bound to the azaindole ring system via a nitrogen atom and all optionally substituted by one or more, identical or different $R^{a2}$ and/or $R^{b2}$;

each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —$C(O)$—$C_{1-6}$alkyl.

In further aspects (F5)(F6)(F7)(F8) the invention relates to compounds (I) with structural aspects (F1)(F2)(F3)(F4), wherein each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl and 3-10 membered heterocyclyl;

each $R^{b2}$ is independently selected from among —$OR^{c2}$, —$NR^{c2}R^{c2}$, halogen, —$C(O)NR^{c2}R^{c2}$, and —CN, and each $R^{c2}$ independently of one another denotes hydrogen or a group selected from among $C_{1-6}$alkyl, $C_{3-6}$cycloalkyl and 3-10 membered heterocyclyl, wherein this heterocyclyl is optionally substituted by one or more, identical or different substituents selected from among halogen, $C_{1-6}$alkyl and —$C(O)$—$C_{1-6}$alkyl.

In another aspect (F9) the invention relates to compounds (I), wherein $R^4$ is

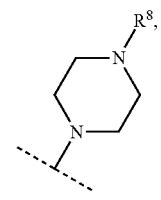

wherein $R^8$ is selected from among $C_{1-6}$alkyl, $C_{3-6}$cycloalkyl, $C_{4-12}$cycloalkylalkyl, —$C(O)C_{1-6}$alkyl and $C_{1-6}$alkyloxy-$C_{1-6}$ alkyl.

In another aspect (F10) the invention relates to compounds (I), wherein $R^4$ is —$NR^{a3}R^{a3}$;

each $R^{a3}$ independently of one another denotes hydrogen or a group optionally substituted by one or more, identical or different $R^{b3}$ and/or $R^{c3}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b3}$ is independently selected from among —$OR^{c3}$, —$NR^{c3}R^{c3}$, halogen, —$C(O)R^{c3}$, —$C(O)OR^{c3}$, —$C(O)NR^{c3}R^{c3}$, —CN, —$NHC(O)R^{c3}$ and —$NHC(O)R^{c3}$;

each $R^{c3}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O—$C_{1-6}$alkyl, $(C_{1-4}$alkyl$)HN$—$C_{1-6}$alkyl, $(C_{1-4}$alkyl$)_2N$—$C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different.

In another aspect (F11) the invention relates to compounds (I), wherein $R^4$ is —$NR^9R^{10}$;

$R^9$ is $C_{1-6}$alkyl and $R^{10}$ is 3-7 membered, nitrogen-containing heterocyclyl, optionally substituted by one or more, identical or different substituents selected from among $C_{1-6}$alkyl, $C_{3-6}$cycloalkyl, $C_{4-12}$cycloalkylalkyl, —$C(O)C_{1-6}$alkyl and $C_{1-6}$alkyloxy-$C_{1-6}$alkyl.

In another aspect (F12) the invention relates to compounds (I), wherein
R⁴ is

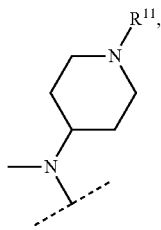

wherein
R¹¹ is selected from among $C_{1-6}$alkyl, $C_{3-6}$cycloalkyl, $C_{4-12}$cycloalkylalkyl, —C(O)$C_{1-6}$alkyl and $C_{1-6}$alkyloxy-$C_{1-6}$alkyl.

In another aspect (F13) the invention relates to compounds (I), wherein
R⁴ is

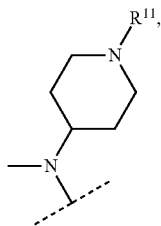

wherein
R¹¹ denotes $C_{1-6}$alkyl.

In another aspect (G1) the invention relates to compounds (I), wherein
R⁶ is chlorine.

In another aspect (G2) the invention relates to compounds (I), wherein
R⁶ is fluorine.

All the above-mentioned structural aspects A1 to A6, B1 and B2, C1 to C5, D1 and D2, CD1 to CD3, E1 to E4, F1 to F13, G1 and G2 are preferred embodiments of the various aspects A0, B0, C0, D0, CD0, E0, F0 and G0, respectively, wherein CD0 (CD) represents the combination of C0 (C) and D0 (D). The structural aspects A0 to A6, B0 to B2, C0 to C5, D0 to D2, CD0 to CD3, E0 to E4, F0 to F13 and G0 to G2 relating to different molecular parts of the compounds (I) according to the invention may be permutated with one another as desired in combinations ABCDEFG, so as to obtain preferred compounds (I). Each combination ABCDEFG represents and defines individual embodiments or generic amounts of compounds according to the invention. Each individual embodiment or partial quantity defined by this combination is expressly also included and is a subject of the invention.

The present invention further relates to hydrates, solvates, polymorphs, metabolites, derivatives and prodrugs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to the use of compounds of general formula (I)—or the pharmaceutically acceptable salts thereof—for preparing a pharmaceutical composition for the treatment and/or prevention of cancer, infections, inflammations and autoimmune diseases.

In another aspect the invention relates to compounds of general formula (I)—or the pharmaceutically acceptable salts thereof—for use in the treatment and/or prevention of cancer.

In another aspect the invention relates to the use of compounds of general formula (I)—or the pharmaceutically acceptable salts thereof—for preparing a pharmaceutical composition for the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to compounds of general formula (I)—or the pharmaceutically acceptable salts thereof—for use in the treatment and/or prevention of colon carcinomas, melanomas, cancer of the gall bladder and thyroid carcinomas.

In another aspect the invention relates to the use of compounds of general formula (I)—or the pharmaceutically acceptable salts thereof—for preparing a pharmaceutical composition for the treatment and/or prevention of colon carcinomas, melanomas, cancer of the gall bladder and thyroid carcinomas.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

DEFINITIONS

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (cycloalkylalkyl, arylalkyl) relates to the total number of carbon atoms of all the carbon ring and carbon chain members.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkenylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

cyclohexyl and

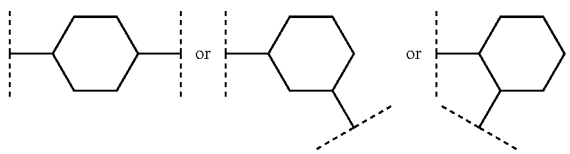

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example: cyclopentenyl and

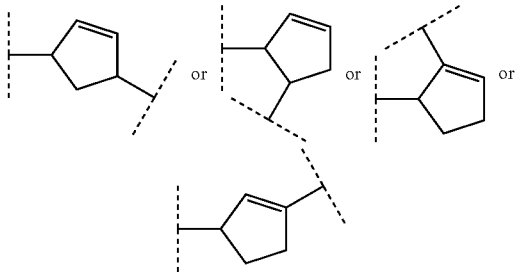

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

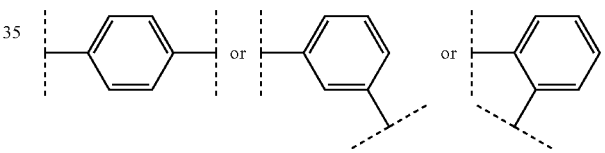

(o, m, p-phenylene), naphthyl and

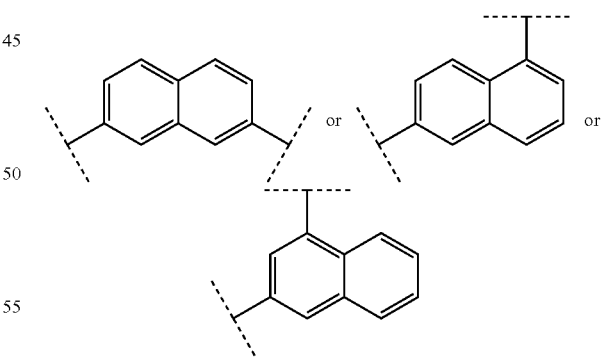

etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-5-oxide, tetrahydrothienyl-S,S-dioxide, homothiomorpholinyl-5-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

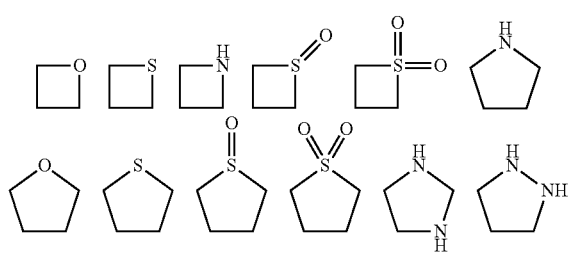

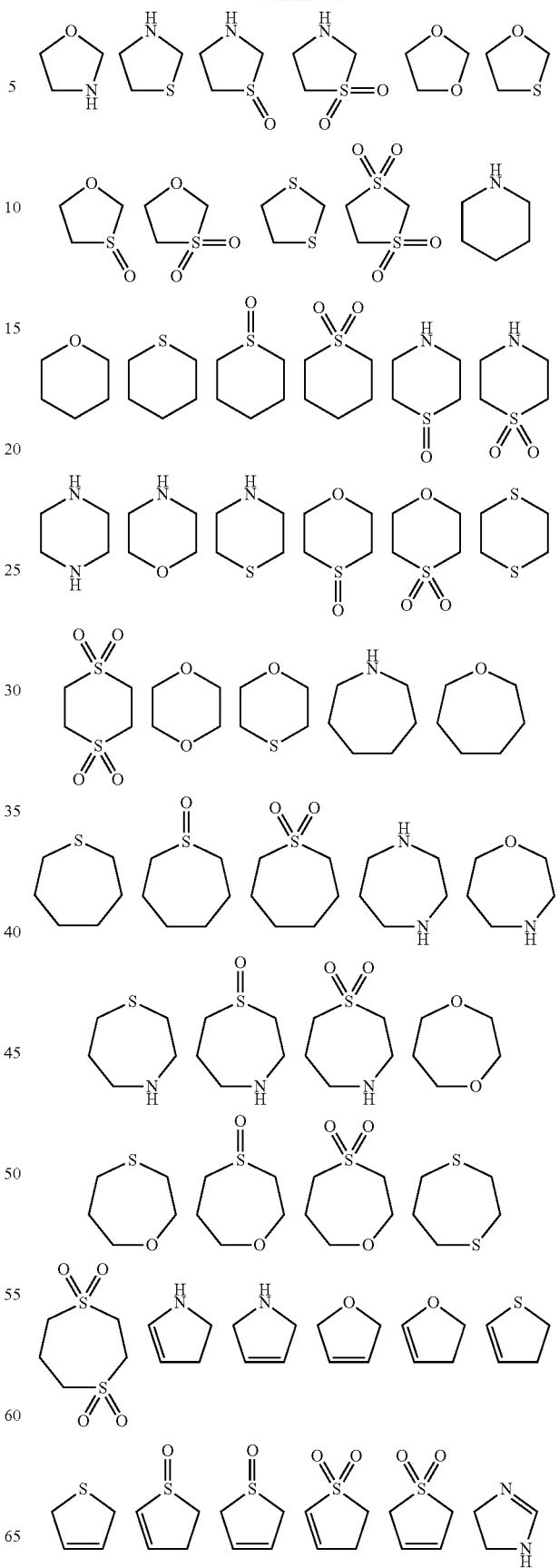

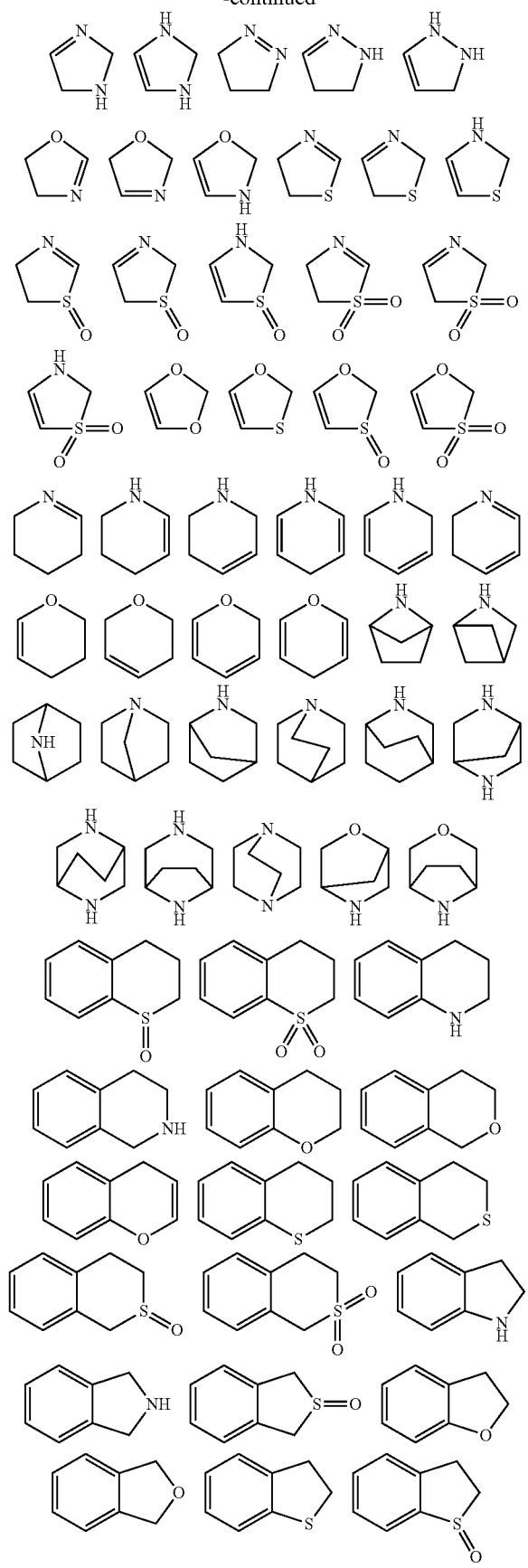
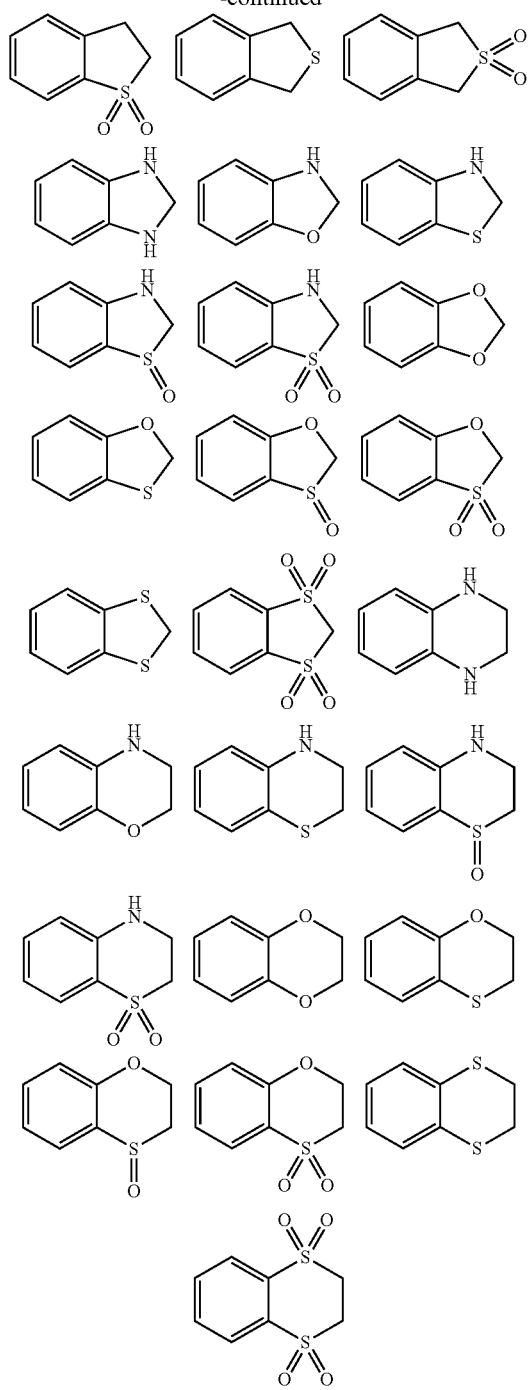

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

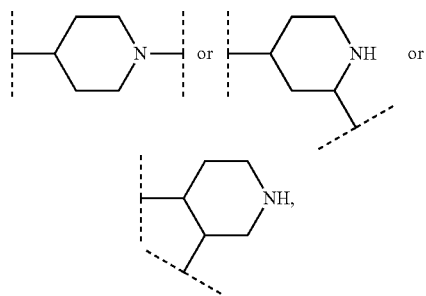

2,3-dihydro-1H-pyrrolyl and

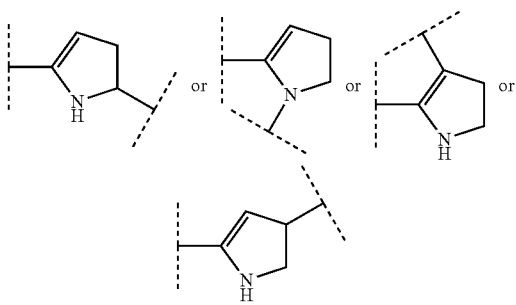

etc.

The above definition of heterocyclylene also applies if heterocyclylene is part of another (combined) group as for example in HO-heterocyclyleneamino or H$_2$N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

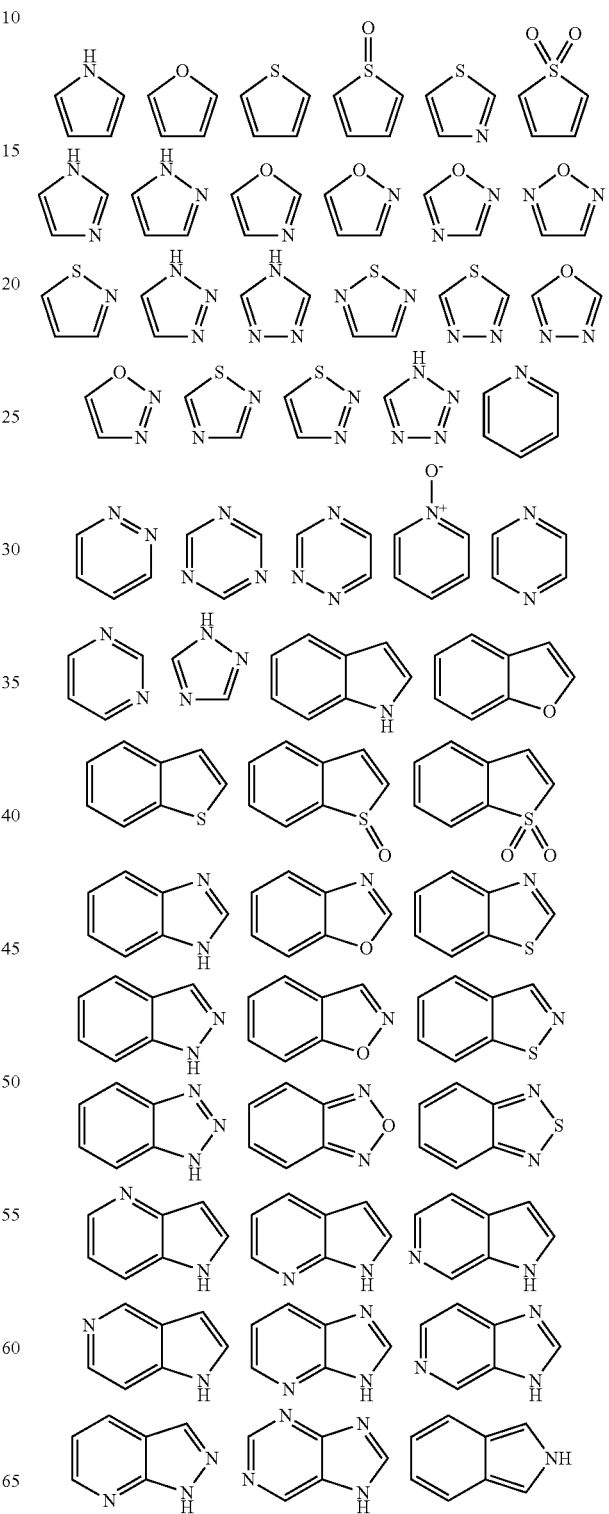

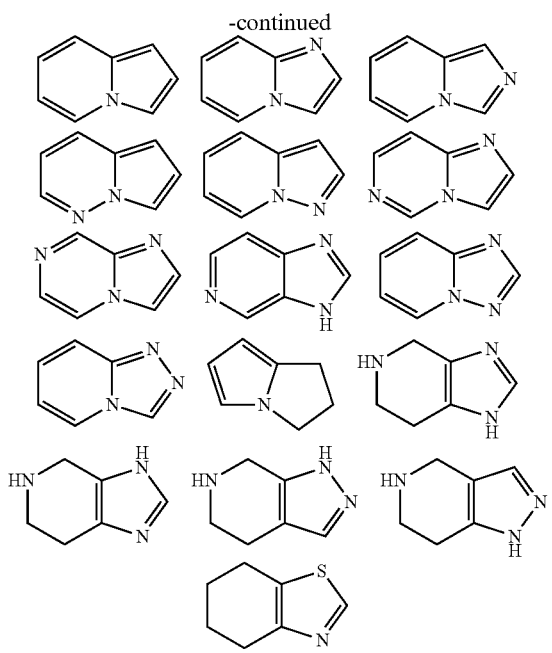

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example: pyrrolyl and

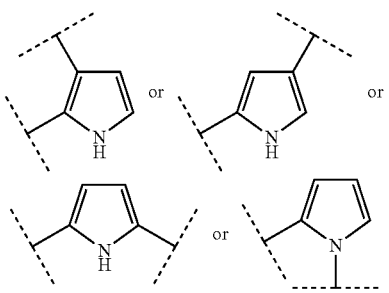

etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH$_2$— or sulphur atoms of a ring system.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

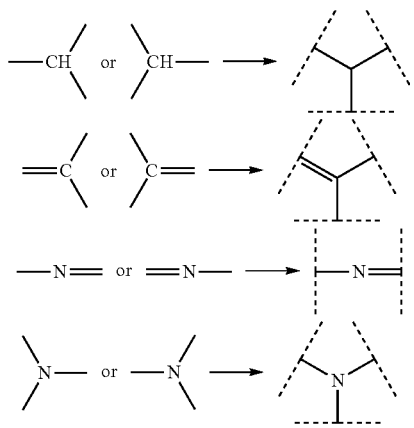

If for example in the sequence X—Y—Z the component Y is supposed to correspond to the structural section —N═, this means both X═N—Z and also X—N═Z.

In a representation such as for example

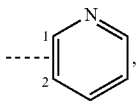

the dotted line means that the ring system may be attached to the molecule via the carbon atom 1 or 2, and is thus equivalent to the following representation

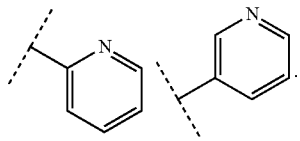

In a representation such as for example

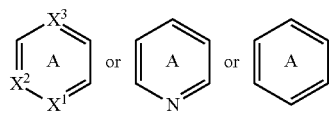

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

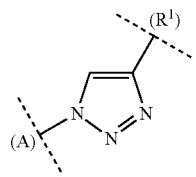

or $(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| | |
|---|---|
| Ac | acetyl |
| AcCN | acetonitrile |
| aq. | aquatic, aqueous |
| ATP | adenosine triphosphate |
| BiPh | biphenyl |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| Et$_2$O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| i | iso |
| Kat., kat. | catalyst, catalytic |
| conc. | concentrated |
| LC | liquid chromatography |
| LiHMDS | lithium bis(trimethylsilyl)amide |
| sln. | solution |
| Me | methyl |
| MeOH | methanol |

-continued

| | |
|---|---|
| min | minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf ($R_f$) | retention factor |
| RP | reversed phase |
| rt | ambient temperature |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the fundamentals of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein).

Microwave reactions are carried out in an initiator/reactor made by Biotage or in an Explorer made by CEM in sealed containers (preferably 2, 5 or 20 mL), preferably with stirring.

Chromatography

For preparative medium pressure chromatography (MPLC) silica gel made by Millipore (name: Granula Silica Si-60A 35-70 μm, NP phase) or C-18 RP-silica gel (RP-phase) made by Macherey Nagel (name: Polygoprep 100-50 C18) is used.

Automated normal phase chromatography is also carried out on a CombiFlash Companion XL apparatus in combination with a CombiFlash Foxy 200 fraction collector made by Isco. For this, commercially obtainable RediSepRf (120 g silica gel) one-way columns are used. Furthermore, automated normal phase chromatography can also be carried out on an Isolera Flash Purification apparatus made by Biotage. For this, commercially obtainable one-way SNAP-Cartridges (e.g. 50 g silica gel) are used.

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out with columns made by Waters (names: XTerra Prep. MS C18, 5 μm, 30×100 mm or XTerra Prep. MS C18, 5 μm, 50×100 mm OBD or Symmetrie C18, 5 μm, 19×100 mm or Sunfire C18 OBD, 19×100 mm, 5 μm or Sunfire Prep C 10 μm OBD 50×150 mm or X-Bridge Prep C18 5 μm OBD 19×50 mm) or X-Bridge Prep C18 10 μm OBD 50×150 mm), Agilent (name: Zorbax SB-C8 5 μm PrepHT 21.2×50 mm) and Phenomenex (names: Gemini C18 5 μm AXIA 21.2×50 mm or Gemini C18 10 μm 50×150 mm). Different gradients of $H_2O$/acetonitrile or $H_2O$/MeOH are used to elute the compounds, while 0.1% HCOOH is added to the water (acidic conditions). For the chromatography under basic conditions $H_2O$/acetonitrile gradients are used as well, while the water is made alkaline as follows: 5 mL $NH_4HCO_3$ solution (158 g in 1 L $H_2O$) and 2 mL $NH_3$ (7 M in MeOH) are replenished to 1 L with $H_2O$.

The preparative high pressure chromatography on normal phase (NP HPLC) of the example compounds according to the invention is carried out with columns made by Macherey & Nagel (name: Nucleosil, 50-7, 40×250 mm) and VDSoptilab (name: Kromasil 100 $NH_2$, 10 μM, 50×250 mm). Different gradients of DCM/MeOH are used to elute the compounds, while 0.1% $NH_3$ is added to the MeOH.

The analytical HPLC (reaction control) of intermediate compounds is carried out using columns made by Agilent (names: Zorbax SB-C8, 5 μm, 21.2×50 mm or Zorbax SB-C8 3.5 μm 2.1×50 mm), Phenomenex (name: Gemini C18 3 μm 2×30 mm) and Waters (names: XBridge™ C18, 3.5 μm, 2.1×50 mm, XBridge™ C18, 5 μm, 2.1×50 mm, XBridge™ C18, 2.5 μm, 2.1×20 mm or Sunfire™ C18, 3.5 μm, 2.1×50 mm. The analytical equipment is also equipped with a mass detector in each case.

HPLC-Mass Spectroscopy/UV-Spectrometry

The retention times/MS-ESI⁺ for characterizing the example compounds according to the invention are produced using an HPLC-MS apparatus (high performance liquid chromatography with mass detector). Compounds that elute at the injection peak are given the retention time $t_{Ret.}$=0.00.

HPLC-MS Method A

HPLC: Agilent 1100 Series
MS: Agilent LC/MSD SL
Column: Waters, XBridge™ C18, 3.5 μm, 2.1×50 mm
Eluent:
 A: $H_2O$ (5 mM $(NH_4)_2CO_3$, 19 mM $NH_3$)
 B: Acetonitrile HPLC grade
Detection: MS: Positive and negative mode
Mass Range: 120-800 m/z
Flow: 1.20 mL/min
Column temperature: rt
Gradient:
 0.00 min 5% B
 0.00-1.25 min 5%→95% B
 1.25-2.00 min 100% B HPLC-MS Method B HPLC: Agilent 1100 Series
MS: Agilent LC/MSD SL
Column: Waters, XBridge™ C18, 5 μm, 2.1×50 mm Eluent:
  A: $H_2O$ (5 mM $(NH_4)_2CO_3$, 19 mM $NH_3$)
  B: Acetonitrile HPLC grade
Detection: MS: Positive and negative mode
Mass Range: 120-800 m/z
Flow: 1.20 mL/min
Column temperature: rt
Gradient:
  0.00 min 5% B
  0.00-1.25 min 5%→95% B
  1.25-2.00 min 95% B
HPLC-MS Method C
HPLC: Agilent 1100 Series
MS: Agilent LC/MSD SL
Column: Waters, XBridge™ C18, 2.5 μm, 2.1×20 mm
Eluent:
  A: $H_2O$ (0.1% $NH_3$)
  B: Acetonitrile HPLC grade
Detection: MS: Positive and negative mode
Mass Range: 120-800 m/z
Flow: 1.00 mL/min
Column temperature: 60° C.
Gradient:
  0.00 min 5% B
  0.00-2.50 min 5%→95% B
  2.50-2.80 min 95% B HPLC-MS method D
HPLC: Agilent 1100 Series
MS: Agilent LC/MSD SL
Column: Waters, Sunfire™ C18, 5 μm, 2.1×50 mm
Eluent:
  A: $H_2O$ (0.2% HCOOH)
  B: Acetonitrile HPLC grade (0.2% HCOOH)
Detection: MS: Positive and negative mode
Mass Range: 120-800 m/z
Flow: 1.20 mL/min
Column temperature: rt
Gradient:
  0.00 min 5% B
  0.00-1.50 min 5%→95% B
  1.50-2.00 min 95% B The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Scheme 1: General synthetic routes towards compounds (I)

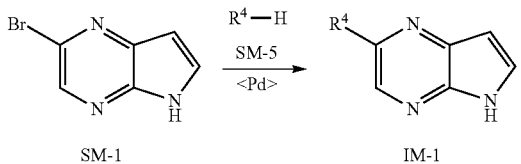

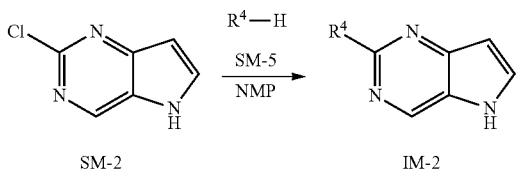

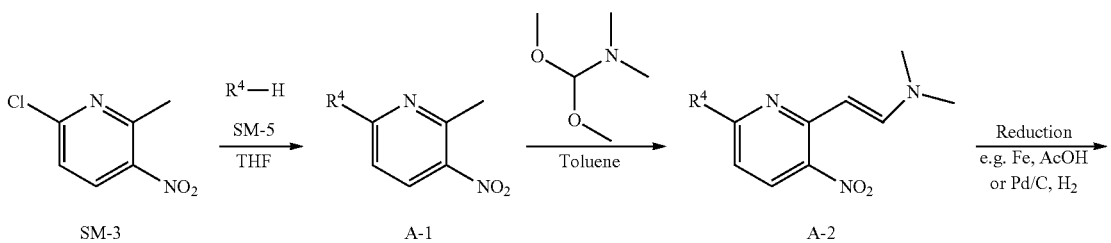

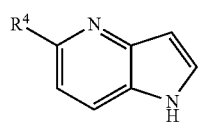

-continued
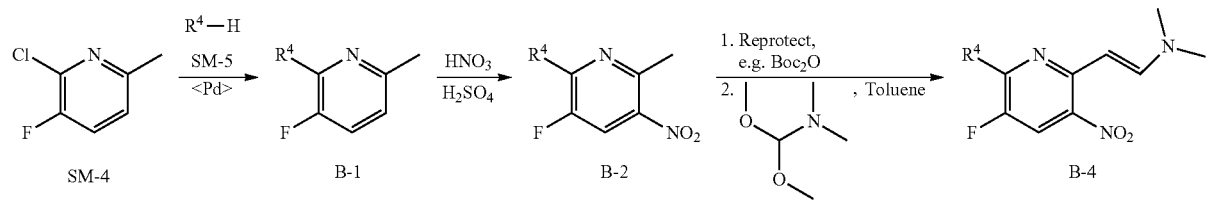
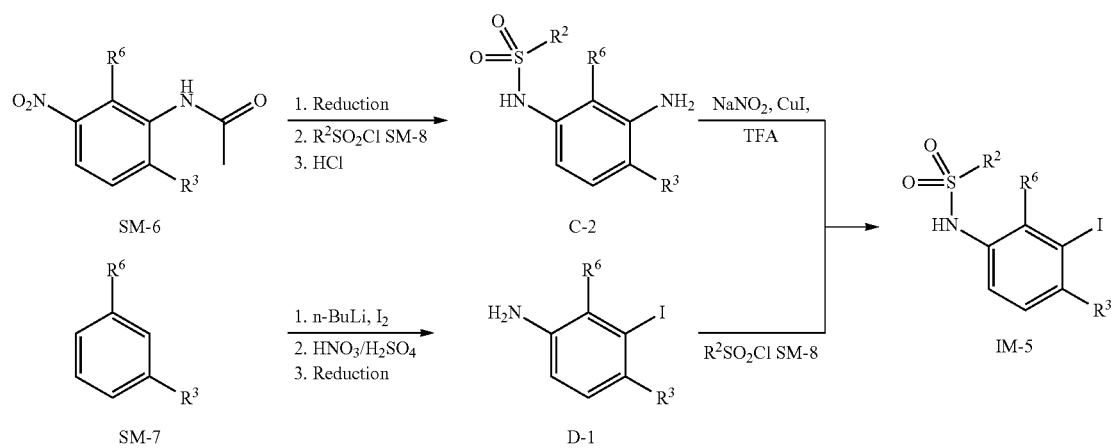
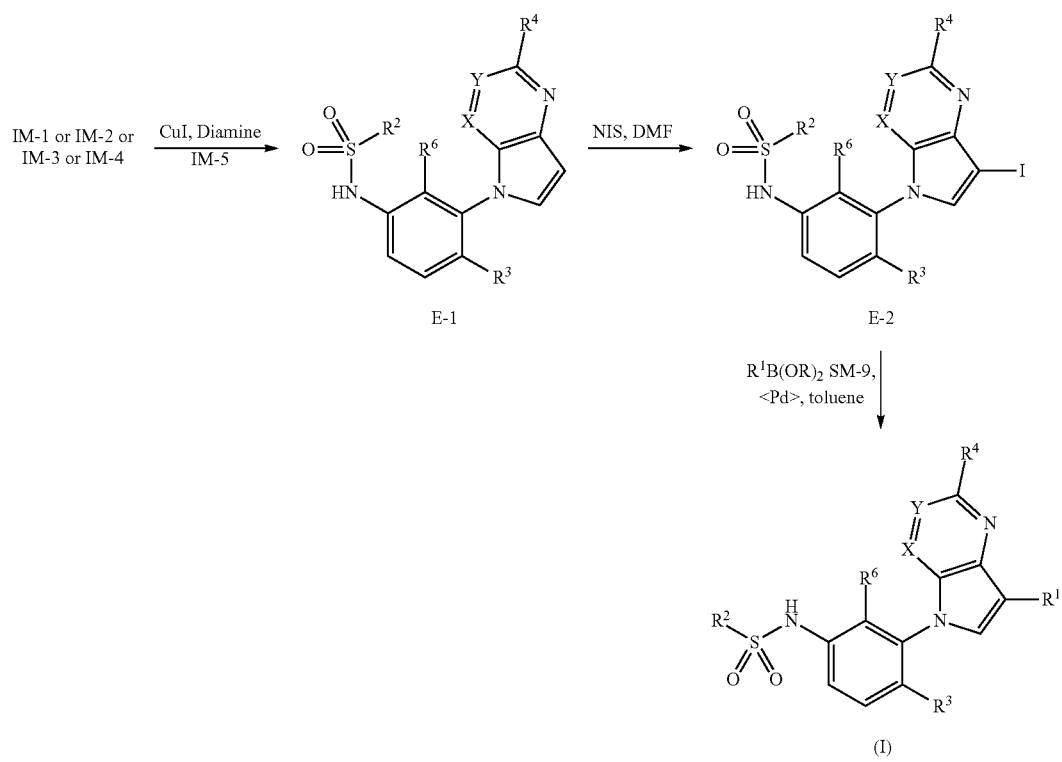

Compounds (I) according to the invention can be prepared in several ways. One way, as described in the general reaction scheme 1, starts from starting materials SM-1 to SM-9 which are either commercially available or can be synthesized as described below.

Intermediate compounds IM-1 are made from the commercially available 2-bromo-5H-pyrrolo[2,3-b]pyrazine via a palladium-catalyzed halogen exchange reaction introducing residue $R^4$.

Intermediate compounds IM-2 can be synthesized by nucleophilic chlorine displacement in starting material 2.

The route to 1H-pyrrolo[3,2-b]pyridines IM-3 starts from 6-chloro-2-methyl-3-nitropyridine SM-3 with a nucleophilic displacement of the halogen. Intermediates IM-3 are then synthesized via Batcho-Leimgruber cyclization.

6-Fluoro-1H-pyrrolo[3,2-b]pyridines IM-4 are synthesized from 2-Chloro-3-fluoro-6-methyl-pyridine SM-4 via a palladium-catalyzed halogen exchange reaction introducing residue $R^4$ and a nitration followed by the Batcho-Leimgruber sequence.

Compounds (I) according to the invention can finally be synthesized through a copper catalyzed coupling Ullmann reaction of iodides IM-5 with pyrrolo derivatives IM-1, IM-2, IM-3 or IM-4, respectively, followed by a iodination and Suzuki reaction.

The iodides IM-5 can be obtained starting from the corresponding anilines via diazotation with $NaNO_2$ and iodide formation with CuI in TFA. The anilines are made from nitro compounds SM-6 through reduction of the nitro function, sulfone amide formation with sulfonic acid chlorides and subsequent deprotection of the amino function with e.g. aqueous HCl. Alternatively, IM-5 can be synthesized starting from the appropriate 1,3 disubstituted benzene SM-7 via deprotonation/iodination and subsequent nitration, reduction and sulfonamidation.

The group $R^1$ in final compounds (I) according to invention as depicted in scheme 1 has structure

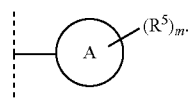

Compounds (I) which are directly synthesized following the synthetic route depicted in scheme 1 and which carry functional groups, either in $R^1$, $R^2$ or $R^4$, that can be further modified such as e.g. halogen atoms, amino and hydroxy groups (including cyclic amines), carboxylic acid or ester functions, nitrils etc. can be optionally derivatized to further compounds (I) by well established organic chemical transformations such as palladium-catalyzed cross coupling reactions, acylation, amidation, addition, reduction or (reductive) alkylation. These additional steps are not depicted in scheme 1.

Likewise, it is also possible to include these additional steps in the synthetic routes depicted in scheme 1, i.e. to carry out derivatization reactions with intermediate compounds.

In addition, it may also be possible that building blocks bearing protecting groups are used, i.e. further steps for deprotection are necessary.

A. Synthesis of Intermediates
A.1. Synthesis of IM-1
A.1.1. Experimental Procedure for the Synthesis of IM-1a

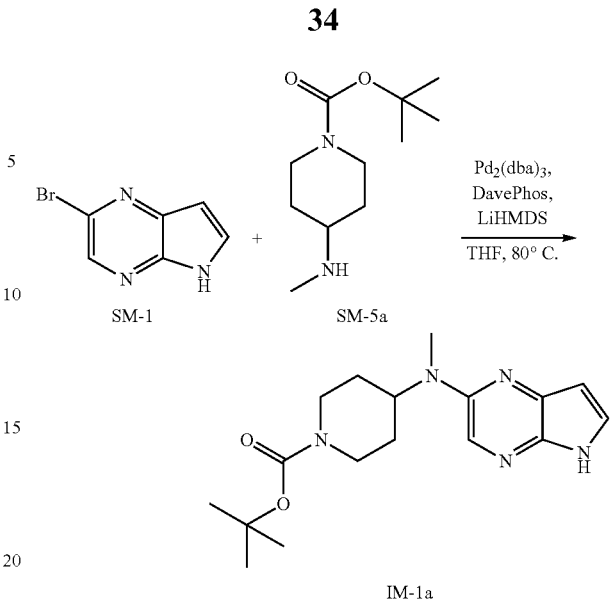

2-Bromo-5H-pyrrolo[2,3-b]pyrazine SM-1 (500 mg, 2.5 mmol), 1-Boc-4-(methylamino)piperidine SM-5a (1.082 g, 5.0 mmol), $Pd_2(dba)_3$ (139 mg, 0.1 mmol), DavePhos (238 mg, 0.6 mmol) and LiHMDS (12.625 mL, 12 mmol) are taken-up in dry THF (10 mL) and the resulting mixture is flushed with Argon and stirred for 1 h at 80° C. The reaction mixture is diluted with $H_2O$ and AcCN, Isolute® is added, the solvent is removed in vacuo and the residue is purified via RP HPLC. The product containing fractions of IM-1a (HPLC-MS method A: $t_{Ret.}$=1.72 min; MS $(M+H)^+$=332) are freeze dried.

A.2. Synthesis of IM-2
A.2.1. Experimental Procedure for the Synthesis of IM-2a

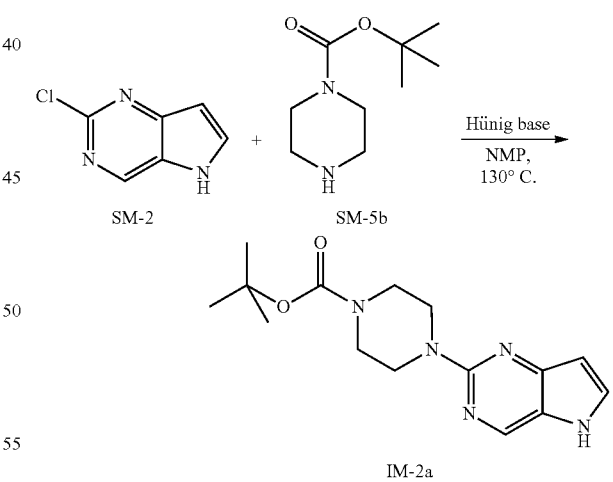

2-Chloro-5H-pyrrolo[3,2-d]pyrimidine SM-2 (1.812 g, 11.8 mmol), N-Boc-piperazine SM-5b (3.296 g, 17.70 mmol) and Hünig base (3.63 mL, 21.01 mmol), are taken-up in dry NMP (2.0 mL) within a sealed tube, and the resulting mixture is stirred for 16 h at 140° C. The reaction mixture is poured into $KHSO_4$ solution (10 and extracted with DCM (100 mL, 3×). The combined organic layer is washed with brine, dried over $MgSO_4$, filtered and evaporated in vacuo. The residue is purified via RP HPLC. The product containing fractions of IM-2a (HPLC-MS method A: $t_{Ret.}$=1.56 min; MS (M+H)$^+$= 304) are combined and evaporated in vacuo.

A.2.2. Experimental Procedure for the Synthesis of IM-2b

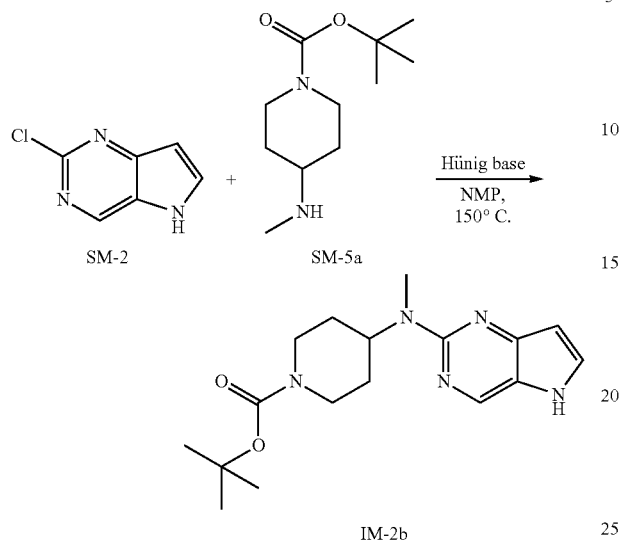

2-Chloro-5H-pyrrolo[3,2-c]pyrimidine SM-2 (3.60 g, 23.44 mmol), 1-Boc-4-(methylamino)piperidine SM-5a (10.05 g, 46.89 mmol) and Hünig base (5.21 mL, 30.48 mmol) are taken-up in dry NMP (5.5 mL) within a sealed tube, and the resulting mixture is stirred for 40 h at 150° C. The reaction mixture is diluted with 400 mL EtOAc and extracted with KHSO$_4$ solution (10%). The pH of the aqueous phase is adjusted to pH 7 with NaOH (1N) and extracted with EtOAc (300 mL, 3×). The combined organic layer is dried over MgSO$_4$, filtered and evaporated in vacuo. The residue is purified via NP-MPLC. The product containing fractions of IM-2b (HPLC-MS method A: $t_{Ret.}$=1.60 min; MS (M+H)$^+$= 332) are combined and evaporated in vacuo.

A.3. Synthesis of IM-3

Experimental Procedure for the Synthesis of IM-3a

Step 1

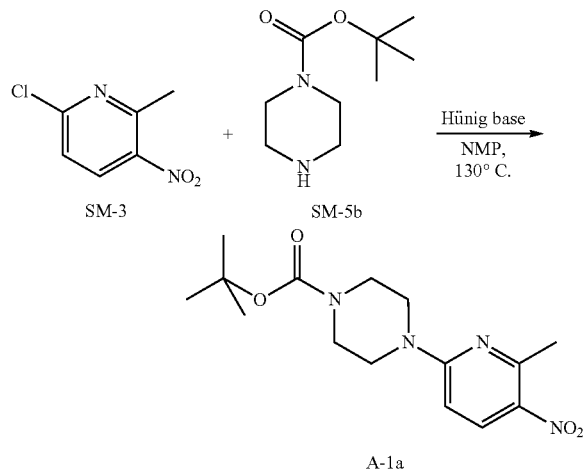

Hünig base (62.82 mL, 0.435 mol) is added to the solution of 6-chloro-3-nitro-2-methylpyridine SM-3 (50 g, 290 mmol) and N-Boc-piperazine SM-5b (53.95 g, 290 mmol) in dry AcCN (200 mL) and stirred for 4 h at 50° C. After the reaction is finished the reaction mixture is diluted with AcCN and water and stirred for 30 min. The precipitated product is collected by filtration, washed with water and the solid is dried in vacuo.

Step 2

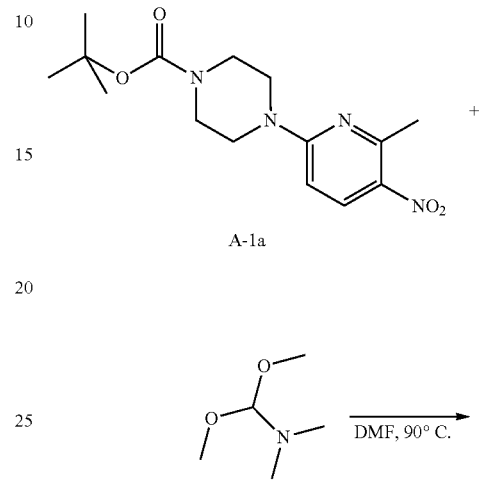

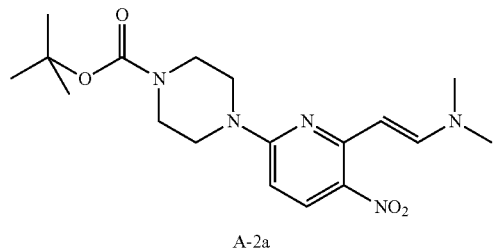

To a stirred solution of 4-(6-methyl-5-nitro-pyridin-2-yl)-piperazine-1-carboxylic acid tert-butyl ester A-1a (13 g, 40.3 mmol) in DMF (35 mL) is added N,N-dimethylformamide dimethylacetal (14.47 g, 121 mmol) and stirred in argon atmosphere for 36 h at 90° C. Additional 1.5 eq. of N,N-dimethylformamide dimethylacetal is added and stirred for 12 h at 90° C. The reaction mixture is poured into water and extracted with DCM. The combined organic layers are washed with water, dried over anhydrous sodium sulphate and concentrated in vacuo. The residue is used without further purification for the next step.

Step 3

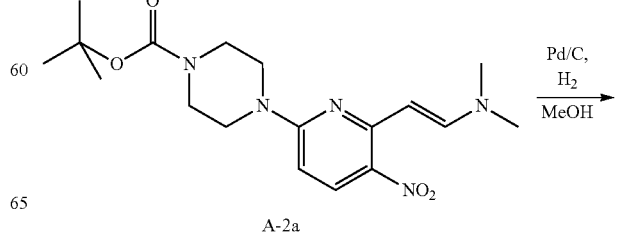

-continued

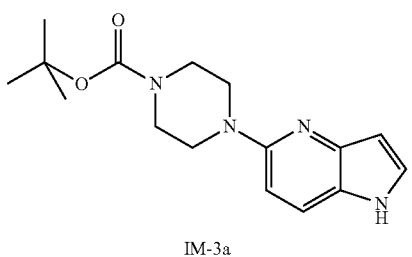

IM-3a

4-[6-((E)-2-Dimethylamino-vinyl)-5-nitro-pyridin-2-yl]-piperazine-1-carboxylic acid tert-butyl ester (36.4 g, 96 mmol) is taken up in MeOH, Pd/C (0.56 g, 10%) is added and the mixture is hydrogenated in an autoclave at 60 psi for 16 h. The reaction mixture is filtered and concentrated under reduced pressure. The residue is purified by column chromatography via NP MPLC. The product containing fractions of IM-3a (HPLC-MS method C: $t_{Ret.}$=1.55 min; MS (M+H)$^+$= 303) are combined and evaporated in vacuo.

Experimental procedure for the synthesis of IM-3b

Step 1

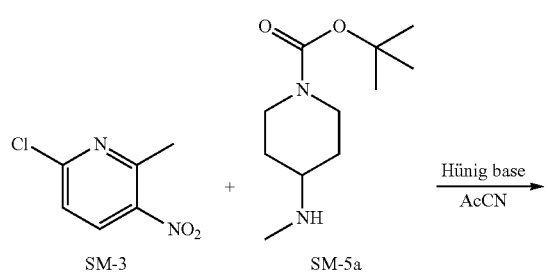

Hünig base (28.03 g, 0.217 mol) is added to the solution of 6-chloro-3-nitro-2-methylpyridine SM-3 (25 g, 145 mmol) and 4-methylamino-piperidine-1-carboxylic acid-tert-butyl-lester SM-5a (40.36 g, 188 mmol) in dry AcCN (200 mL) and stirred for 30 h at 65° C. After the reaction is finished the reaction mixture is diluted with AcCN and water and stirred for 15 min. The precipitated product is collected by filtration, washed with water and the solid is dried in vacuo.

Step 2

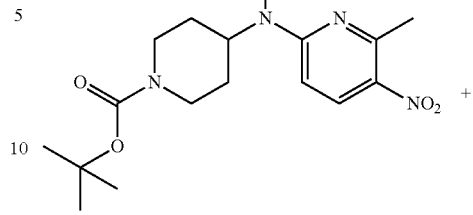

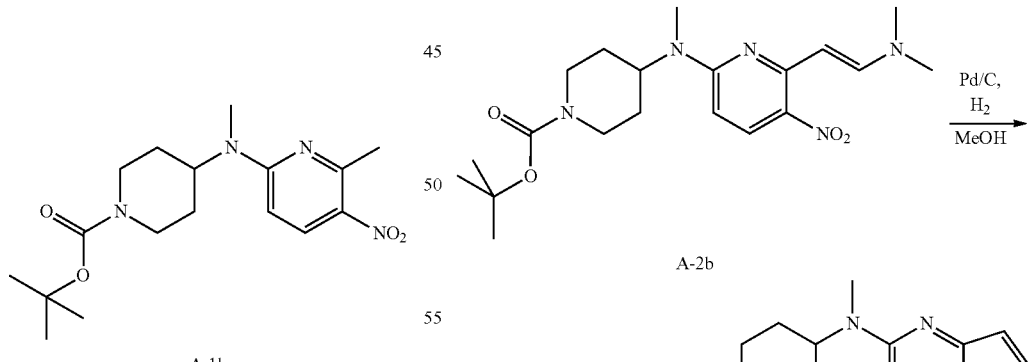

To a stirred solution of tert-butyl 4-[methyl-(6-methyl-5-nitro-2-pyridyl)amino]piperidine-1-carboxylate A-1b (30 g, 85.6 mmol) in DMF (100 mL) is added N,N-dimethylformamide dimethylacetal (30.56 g, 256.8 mmol) and stirred in argon atmosphere for 72 h at 90° C. The reaction mixture is poured into water. The precipitated product is collected by filtration, washed with water and dried (45° C.) over night in vacuo. The residual A-2b is used without further purification for the next step.

Step 3

Tert-butyl 4-[[6-[(E)-2-(dimethylamino)vinyl]-5-nitro-2-pyridyl]-methyl-amino]piperidine-1-carboxylate A-2b (30.0 g, 74 mmol) is taken up in MeOH (100 mL), Pd/C (3.0 g, 10%) is added and the mixture is hydrogenated in an autoclave at 50 psi for 90 min. The reaction mixture is filtered and concentrated under reduced pressure. The residue is purified by column chromatography via NP-MPLC. The product containing fractions of IM-3b (HPLC-MS method C: $t_{Ret.}$=1.55 min; MS (M+H)$^+$=303) are combined and evaporated in vacuo.

A.4. Synthesis of IM-4

Experimental Procedure for the Synthesis of IM-4-a

Step 1

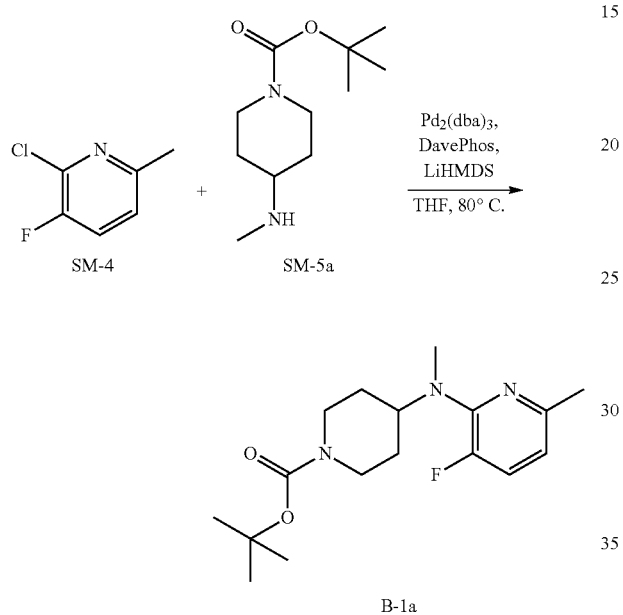

2-Chloro-3-fluoro-6-methylpyrimidine SM-4 (1.0 g, 6.9 mmol), 1-Boc-4-(methylamino)piperidine SM-5a (2.95 g, 13.7 mmol), Pd$_2$(dba)$_3$ (190 mg, 0.2 mmol), DavePhos (324 mg, 0.8 mmol) and LiHMDS (34.35 mL, 134.35 mmol) are taken-up in dry THF (20 mL) and the resulting mixture is flushed with argon and stirred for 45 min at 80° C. The reaction mixture is diluted with DCM, washed with H$_2$O and brine. The organic layer is dried, filtered and concentrated under reduced pressure. Isolute® is added, the solvent is removed in vacuo and the residue is purified via NP-MPLC. The product containing fractions of B-1a are combined and concentrated in vacuo.

Step 2

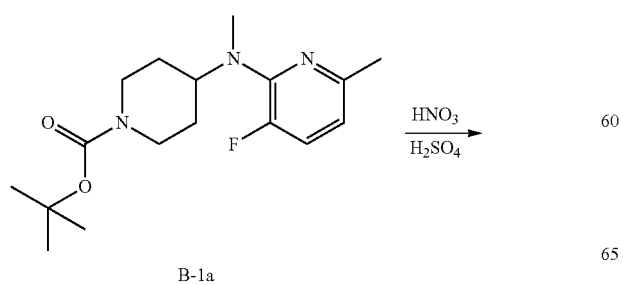

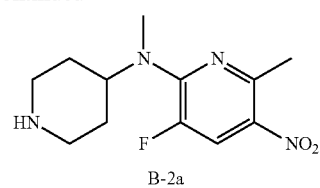

To B-1a (0.3 g, 0.9 mmol) in H$_2$SO$_4$ (conc., 0.1 mL) at 0° C. is slowly added HNO$_3$ (conc., 0.1 mL). The resulting mixture is stirred for 2 h at 25° C. The reaction mixture is poured on ice. The resulting precipitate is filtered, collected and dried (45° C.) over night in vacuo. The residual B-2a is used without further purification for the next step.

Step 3

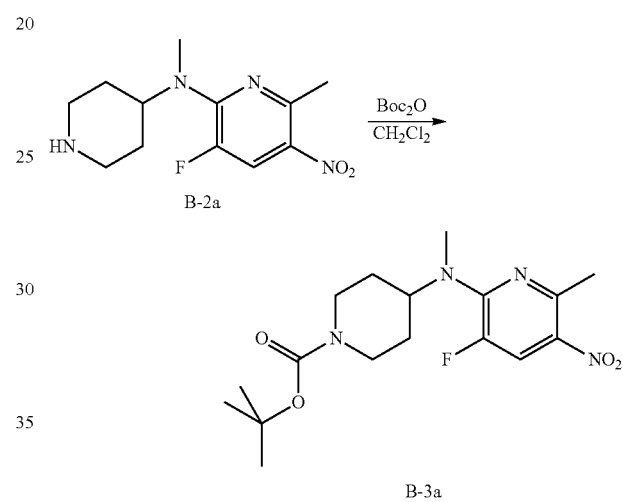

To B-2a (0.15 g, 0.58 mmol) in DCM (2 mL) is slowly added Boc$_2$O (189 mg, 0.87 mmol). The resulting mixture is stirred for 20 min at 25° C. Isolute® is added, the solvent is removed in vacuo and the residue is purified via NP-MPLC. The product containing fractions of B-3a (HPLC-MS method B: $t_{Ret.}$=1.62 min; MS (m−H)$^−$=367) are combined and concentrated in vacuo.

Step 4

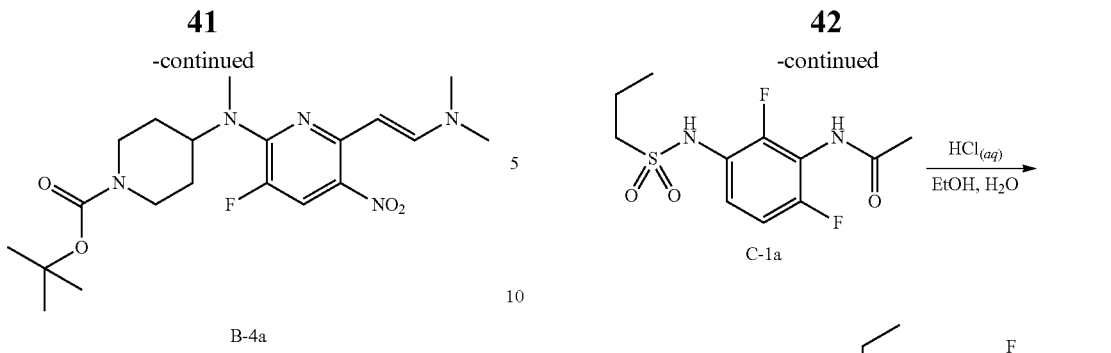

To a stirred solution of B-3a (2.0 g, 5.43 mmol) in DMF (1 mL) is added N,N-dimethylformamide dimethylacetal (5.0 mL, 38.0 mmol) and stirred in argon atmosphere for 36 h at 90° C. The reaction mixture is slowly poured into water and extracted with DCM. The resulting precipitate is filtered, collected and dried (45° C.) over night in vacuo. The residual B-4-a was used without further purification for the next step.

Step 5

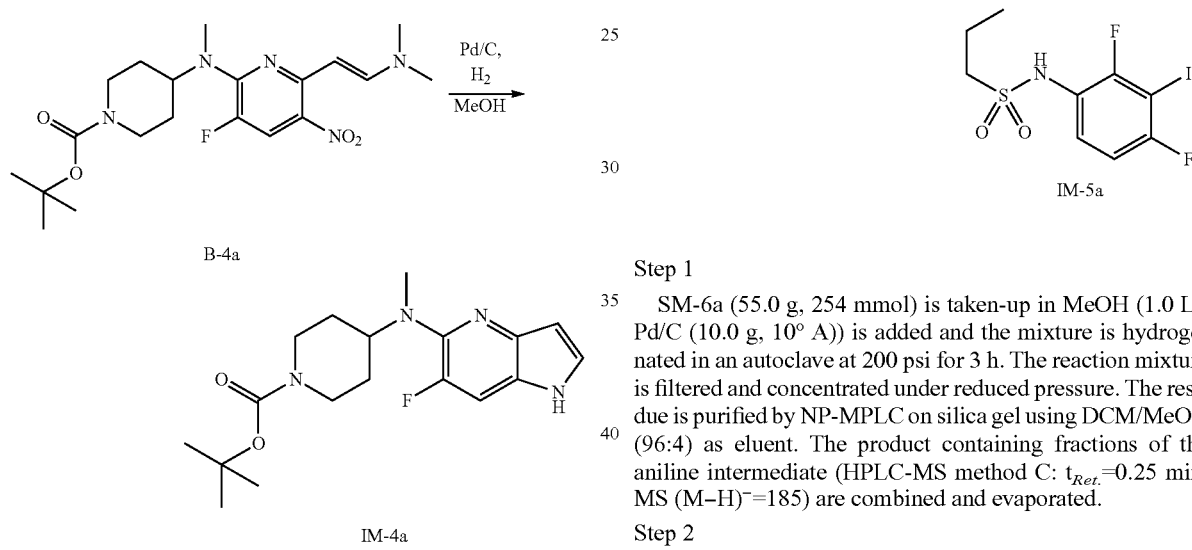

B-4-a (0.5 g, 1.2 mmol) is taken up in MeOH/THF (1:3, 10 mL), Pd/C (0.05 g, 10° A)) is added and the mixture is hydrogenated in an autoclave at 60 psi for 2 h. The reaction mixture is filtered and concentrated under reduced pressure. The residue is purified by column chromatography via NP-MPLC. The product containing fractions of IM-4-a (HPLC-MS method B: $t_{Ret.}$=1.35 min; MS (M+H)$^+$=349) are combined and evaporated in vacuo.

A.5. Synthesis of IM-5

Experimental Procedure for the Synthesis of IM-5a

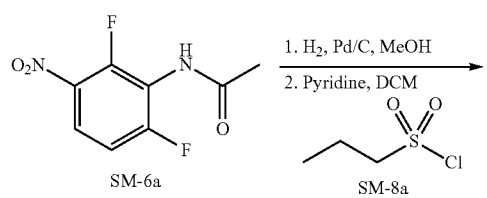

Step 1

SM-6a (55.0 g, 254 mmol) is taken-up in MeOH (1.0 L). Pd/C (10.0 g, 10° A)) is added and the mixture is hydrogenated in an autoclave at 200 psi for 3 h. The reaction mixture is filtered and concentrated under reduced pressure. The residue is purified by NP-MPLC on silica gel using DCM/MeOH (96:4) as eluent. The product containing fractions of the aniline intermediate (HPLC-MS method C: $t_{Ret.}$=0.25 min; MS (M−H)$^−$=185) are combined and evaporated.

Step 2

To the aniline intermediate (35.0 g, 188 mmol) in DCM (100 mL) pyridine (6.6 mL, 75 mmol) and n-propane sulfonyl chloride SM-8a (29.5 mL, 263 mmol) are added and the mixture is stirred at rt for 16 h. The reaction mixture is diluted with EtOAc (200 mL), washed with H$_2$O and HCl (aq., 1 N) and the layers are separated, dried over MgSO$_4$ and evaporated to yield the sulphonylated aniline C-1a which was used without further purification.

Step 3

The sulphonylated aniline C-1a (38.0 g, 130 mmol) is taken-up in EtOH (250 mL), H$_2$O (200 mL) and concentrated hydrochloric acid (200 mL) and heated to 80° C. for 2 h. The reaction mixture is concentrated under reduced pressure, aqueous NaOH (4 N) is added until pH=6 is reached and the mixture is extracted 2× with DCM. The combined organic layer is washed with brine, dried over MgSO$_4$, filtered and evaporated to yield the deacylated aniline C-2a (HPLC-MS method C: $t_{Ret.}$=0.22 min; MS (M−H)$^−$=249) as a hydrochloride which was used without further purification.

Analogously to this procedure additional anilines C-2 can be prepared (also using other nitro compounds SM-6) with various sulfonyl chlorides SM-8.

TABLE 1

Anilines C-2

| # | structure | $t_{Ret.}$ (HPLC) [min] | MS (M+H)$^+$ |
|---|---|---|---|
| C-2a | [structure: propyl-SO2-NH-phenyl(F)(NH2)(F)] | 0.22 | 251 |
| C-2b | [structure: tetrahydrofuran-CH2-SO2-NH-phenyl(F)(NH2)(F)] | n.a. | n.a. |
| C-2c | [structure: cyclopropyl-CH2-SO2-NH-phenyl(F)(NH2)(F)] | n.a. | n.a. |
| C-2d | [structure: cyclopropyl-SO2-NH-phenyl(F)(NH2)(F)] | 1.58 | 249 |
| C-2e | [structure: furan-SO2-NH-phenyl(F)(NH2)(F)] | n.a. | n.a. |
| C-2f | [structure: propyl-SO2-NH-phenyl(Cl)(NH2)(F)] | n.a. | n.a. |

Step 4

The hydrochloride of C-2a is taken-up in DCM and extracted with NaHCO$_3$ solution (semiconc.). The organic layer is dried over MgSO$_4$, filtered and evaporated. To the free base C-2a (3.55 g, 14.21 mmol) in TFA (80 mL) at 0° C. is added NaNO$_2$ (1.96 g, 28.4 mmol) in small portions and the mixture is stirred for 30 min. KI (23.83 g, 142 mmol) is added and stirring is continued for additional 15 min. The reaction mixture is diluted with Et$_2$O and stirred for 1 h. Na$_2$S$_2$O$_3$ solution (semiconc.) is added and the mixture is extracted 3× with Et$_2$O. The combined organic layer is dried over MgSO$_4$, filtered and concentrated in vacuo. The residue is purified by column chromatography via NP-MPLC. The product containing fractions of IM-5a (HPLC-MS method B: $t_{Ret.}$=1.58 min; MS (M–H)$^-$=360) are combined and evaporated in vacuo.

Analogously to this procedure additional iodides IM-5 can be prepared starting with various anilines C-2.

Experimental Procedure for the Synthesis of IM-5b

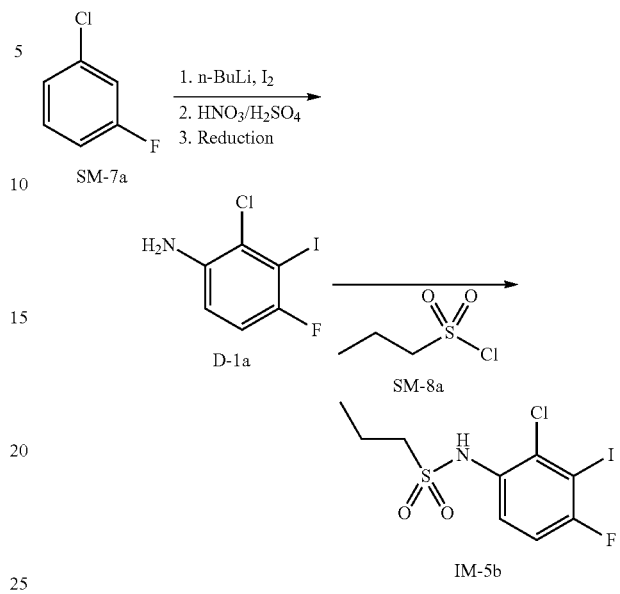

Step 1

N-Butyllithium is added to THF at –78° C. To this SM-7a is added at –78° C. and then stirred for 20 min at –78° C. Iodine (96.9 g, 0.38 mol) dissolved in THF is added dropwise at –78° C. over a period of 1 h and then stirred for 1 h at –78° C. The reaction mixture is then poured into ammonium chloride solution and extracted with EtOAc. The organic layer is washed with Na$_2$S$_2$O$_3$ solution, dried over sodiumsulphate and concentrated in vacuo. The residual 2-chloro-6-fluoro-iodbenzene was used without further purification for the next step.

Step 2

2-Chloro-6-fluoro-iodbenzene (10 g, 39 mmol) is dissolved in sulfuric acid (conc., 17 mL) at 0° C. A mixture of nitric acid (conc, 3.2 mL) and sulfuric acid (conc., 3.2 mL) is added at 0° C. and stirring is continued for 2 h at 25° C. The reaction mixture is poured onto ice. The resulting precipitate is collected, dried and used without further purification for the next step.

Step 3

2-Chloro-6-fluoro-3-nitro-iodobenzene (5 g, 17 mmol) is dissolved in 50 mL EtOH. NH$_4$Cl (8.8 g, 164.5 mmol) and H$_2$O (8 mL) are added. The solution is heated to 60° C., iron (powder, 6.56 g, 117.4 mmol) is added and stirring is continued for 30 min at 70° C. After cooling to 25° C. Celite is added and the suspension is filtrated over Celite. The solvent is removed in vacuo and the residue is redissolved in EtOAc, dried over MgSO$_4$, filtered and reconcentrated in vacuo. The residue is purified by column chromatography via NP-MPLC. The product containing fractions of D-1a (HPLC-MS method D: $t_{Ret.}$=1.66 min; MS (M+H)$^+$272) are combined and the solvent is removed in vacuo.

Step 4

To the aniline intermediate D-1a (3.5 g, 13 mmol) in DCM (35 mL) pyridine (2.2 mL, 26 mmol) and n-propane sulfonyl chloride SM-8a (1.7 mL, 14 mmol) are added and the mixture is stirred at rt for 16 h. The reaction mixture is diluted with EtOAc (100 mL), washed with H$_2$O and KHSO$_4$ solution (10%), dried over MgSO$_4$ and the solvent is removed in vacuo. The residue is purified by column chromatography via NP-MPLC. The product containing fractions of IM-5b (HPLC-MS method B: $t_{Ret.}$=0.99; MS (M−H)⁻=376) are combined and evaporated in vacuo.

B. Synthesis of Final Compounds (I)
B.1. Synthesis of Example Compound I-1
B.1.1. Experimental Procedure for the Synthesis of E-1a

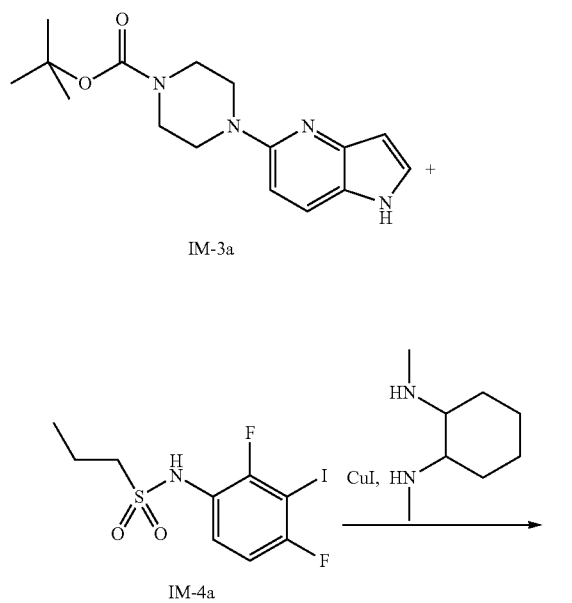

B.1.2. Experimental Procedure for the Synthesis of E-2a

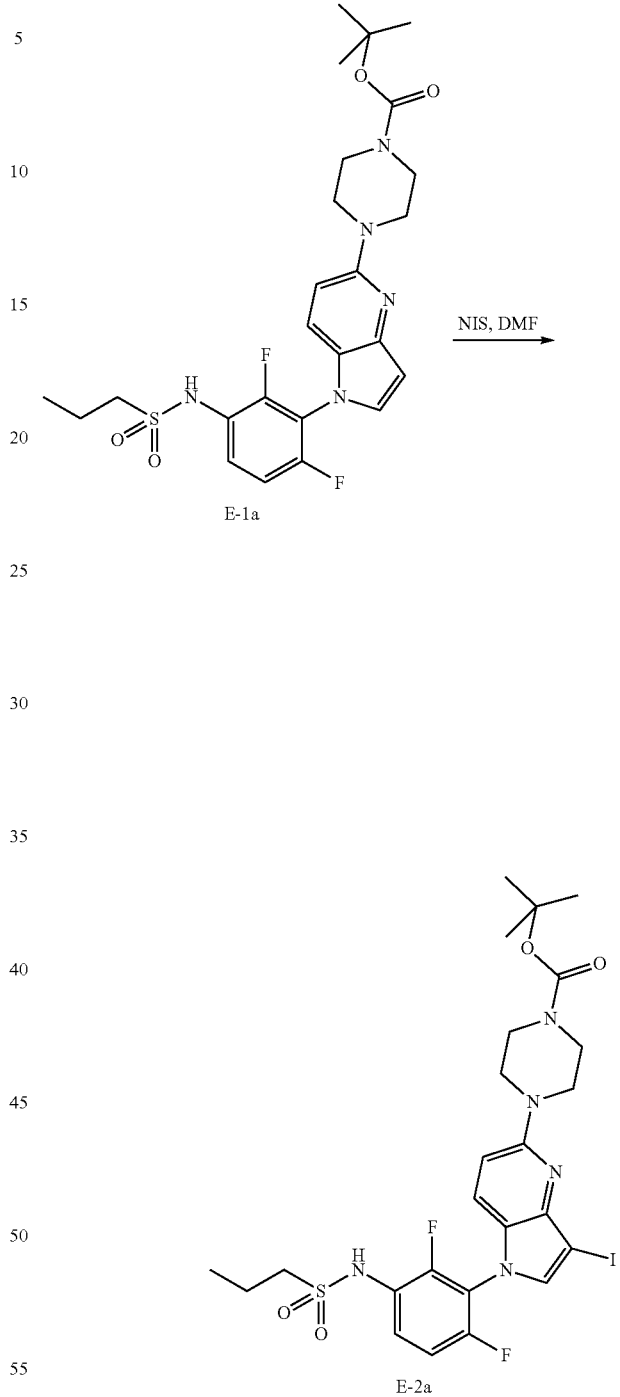

1H-Pyrrolo[3,2-b]pyridin IM-3a (250 mg, 0.83 mmol), sulfonamide IM-4-a (315 mg, 0.83 mmol), CuI (15.8 mg, 0.08 mmol), trans-(1R,2R)—N,N'-bismethyl-1,2-cyclohexandiamine (52.2 µL, 0.33 mmol) and K₃PO₄ (530 mg, 2.50 mmol) are taken-up in dry toluene (3 mL) and the resulting mixture is flushed with argon and stirred for 16 h at 120° C. The reaction mixture is diluted with H₂O and AcCN, Isolute® is added, the solvent is removed in vacuo and the residue is purified via RP HPLC. The product containing fractions of E-1a (HPLC-MS method D: $t_{Ret.}$=1.68 min; MS (M−H)⁻= 534) are freeze dried.

To a solution of sulfonamide E-1a (267 mg, 0.5 mmol) in DMF (3 mL) is added NIS (115 mg, 0.5 mmol) and the mixture is stirred for 1 h at rt. The reaction mixture is diluted with 30 mL DCM and extracted with NaHCO₃ solution (semiconc.). The combined organic layer is dried over MgSO₄, filtered and concentrated under reduced pressure. The residue is purified by column chromatography via RP HPLC. The product containing fractions of E-2a (HPLC-MS method C: $t_{Ret.}$=1.94 min; MS (M+H)⁺=662) are freeze dried.

B.1.3. Experimental Procedure for the Synthesis of 1-1

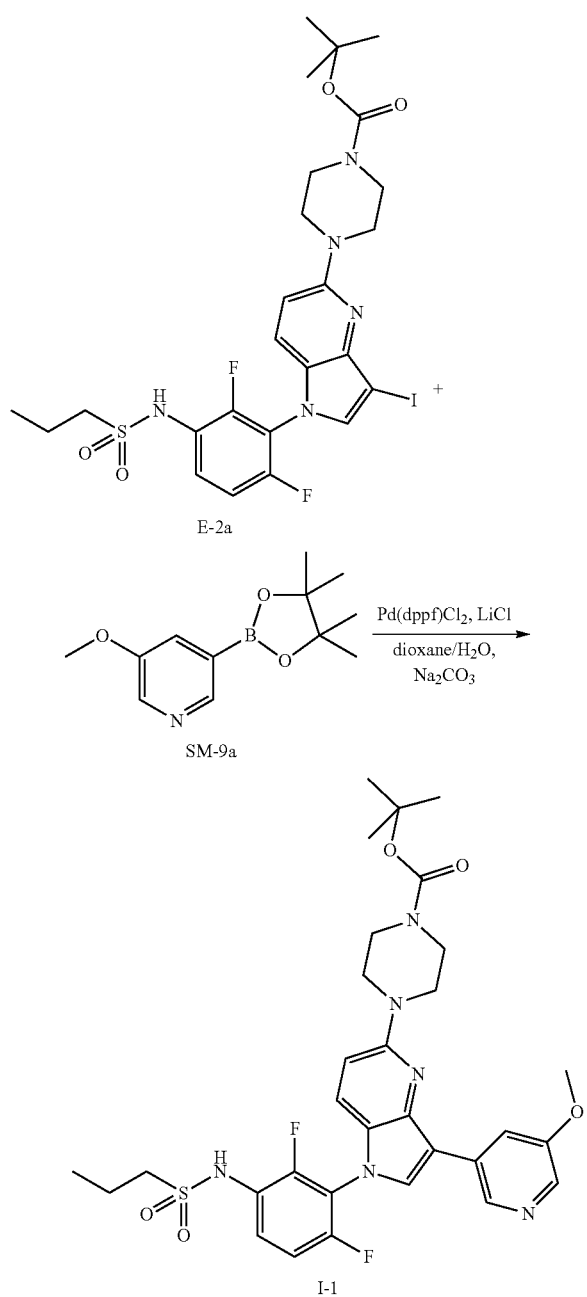

Sulfonamide E-2a (214 mg, 0.32 mmol), 3-methoxy-5-pyridineboronic acid pinacol ester (152 mg, 0.65 mmol), Pd(dppf)Cl$_2$ (24 mg, 0.03 mmol), LiCl (41 mg, 0.98 mmol) and Na$_2$CO$_3$ (85 mg, 0.81 mmol) are taken-up in dioxane/H$_2$O (2:1 mixture, 2 mL), and the resulting mixture is flushed with argon and stirred for 0.5 h at 100° C. in the microwave reactor. The reaction mixture is diluted with H$_2$O and EtOAc.

The organic layer is separated, Isolute® is added to the organic layer, the solvent is removed in vacuo and the residue is purified via RP HPLC. The product containing fractions of I-1 (HPLC-MS method B: $t_{Ret.}$=1.82 min; MS (M+H)$^+$=643) are freeze dried.

B.2. Synthesis of Example Compound I-2
B.2.1. Experimental Procedure for the Synthesis of 1-2

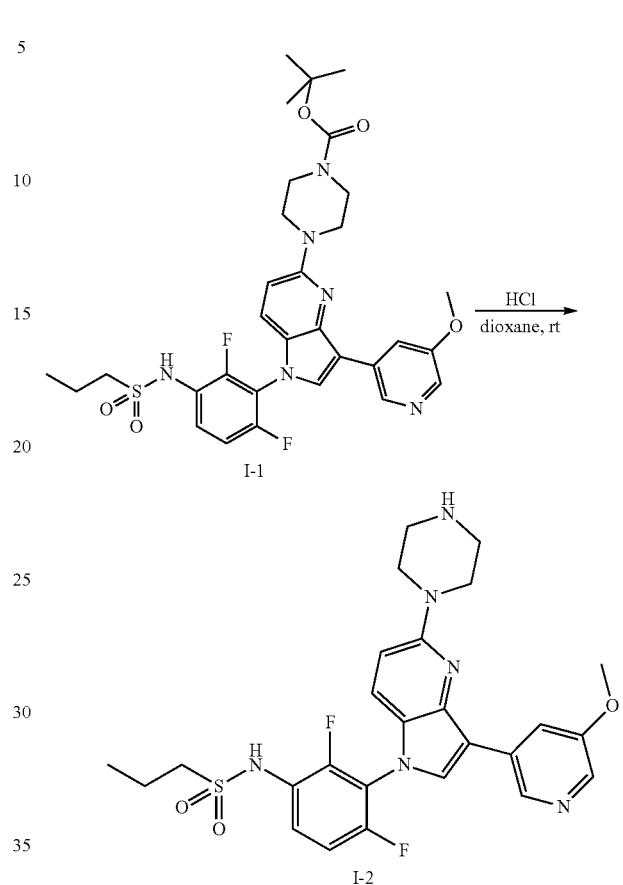

To a solution of example compound I-1 (127 mg, 0.2 mmol) in DCM (2 mL) is added HCl (in dioxane, 4 N, 1 mL) and the mixture is stirred for 45 min at rt. The reaction mixture is diluted with NaHCO$_3$ solution (semiconc., 100 mL) and extracted with DCM. The combined organic layer is dried over MgSO$_4$, filtered and the solvent is removed in vacuo. Optained compound I-2 (HPLC-MS method B: $t_{Ret.}$=1.50 min; MS (M+H)$^+$=543) is used without further purification for the next step.

B.3. Synthesis of Example Compound I-3
B.3.1. Experimental Procedure for the Synthesis of 1-3

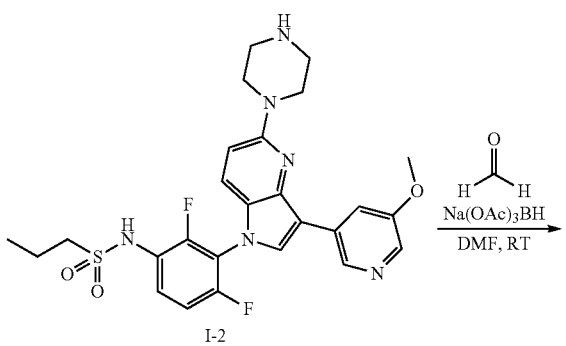

-continued

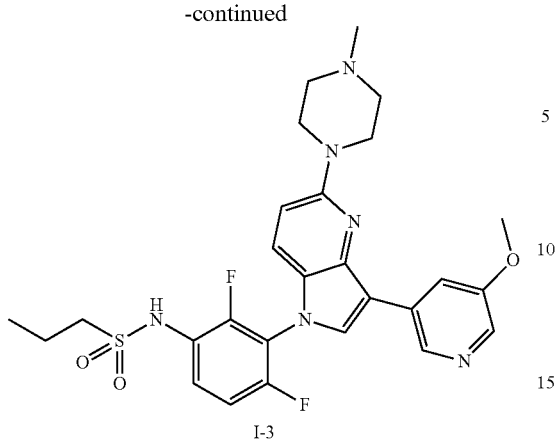

I-3

Example compound I-2 (50 mg, 0.09 mmol), formaldehyde (in H₂O, 28 μL, 0.37 mmol) and AcOH (2.6 μL, 0.05 mmol) are taken-up in DMF (0.5 mL) and the resulting mixture is stirred for 10 min at rt. Na(OAc)₃BH (97 mg, 0.46 mmol) is added and the mixture is stirred for 3 d. The pH of the reaction mixture is adjusted to pH 8 with NH₃ (aq.), diluted with DMF and purified via RP HPLC. The product containing fractions are freeze dried to yield 1-3 (HPLC-MS method C: $t_{Ret.}$=0.98 min; MS (M+H)$^+$=557).

B.4. Synthesis of Example Compound I-4
B.4.1. Experimental Procedure for the Synthesis of I-4

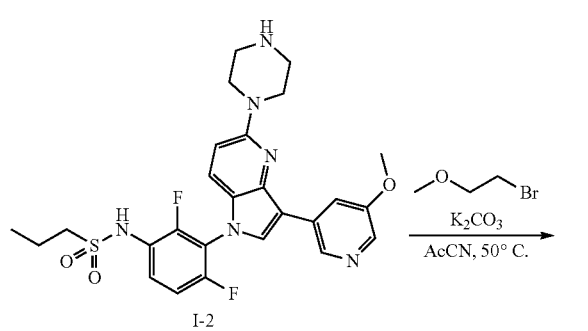

I-4

To a suspension of 1-2 (50 mg, 0.09 mmol) and K₂CO₃ (138.0 mg, 0.46 mmol) in AcCN (0.5 mL) is added 2-bromoethyl-methyl-ether (26 μL, 0.28 mmol) and the mixture is stirred at 50° C. for 14 h. The reaction mixture is diluted with NaHCO₃ solution (semiconc.) and extracted with DCM. The combined organic layer is dried over MgSO₄, filtered and concentrated under reduced pressure. The residue is purified via RP HPLC. The product containing fractions are freeze dried to give I-4 (HPLC-MS: $t_{Ret.}$=1.00 min; MS (M+H)$^+$=601).

B.5. Synthesis of Example Compound I-13
B.5.1. Experimental Procedure for the Synthesis of E-1b

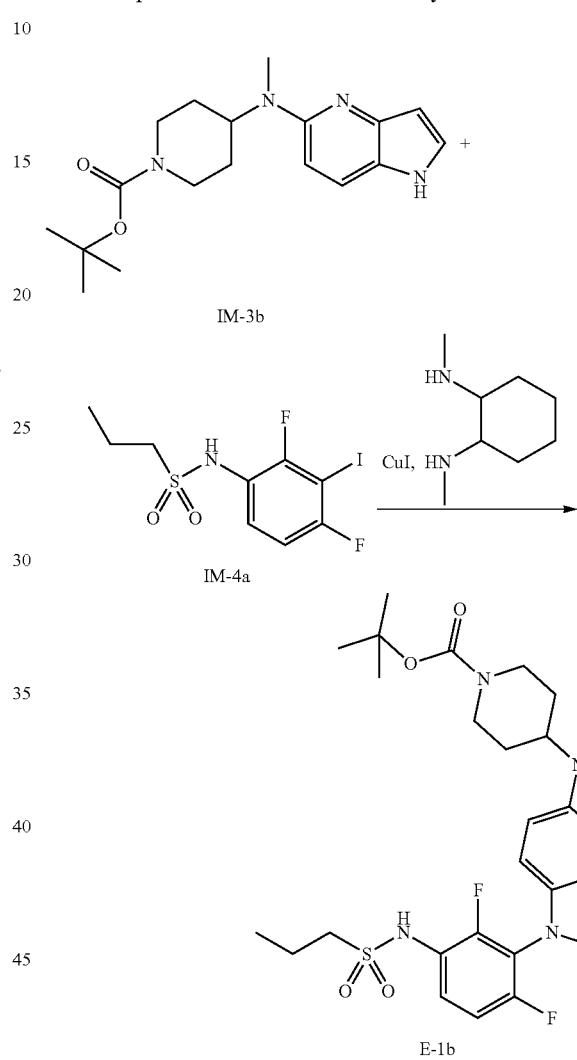

E-1b

1H-Pyrrolo[3,2-b]pyridin IM-3b (10.0 g, 30.27 mmol), sulfonamide IM-4-a (16.4 g, 45.4 mmol), CuI (576 mg, 3.03 mmol), trans-(1R,2R)—N,N'-bismethyl-1,2-cyclohexandiamine (1.91 mL, 12.1 mmol) and Cs₂CO₃ (29.6 g, 90.85 mmol) are taken-up in dry toluene (3 mL) and the resulting mixture is flushed with argon and stirred for 16 h at 120° C. After the addition of further CuI (576 mg, 3.03 mmol), trans-(1R,2R)—N,N'-bismethyl-1,2-cyclohexandiamine (1.91 mL, 12.1 mmol) and Cs₂CO₃ (20.0 g, 60.0 mmol) the reaction mixture is stirred for further 24 h. The solvent is removed in vacuo, the residue is taken up in DCM and extracted with NaHCO₃ solution (semiconc.). The organic layer is dried over MgSO₄, filtered, the solvent is removed in vacuo and the residue is purified via NP-MPLC. The product containing fractions of E-1b (HPLC-MS method D: $t_{Ret.}$=1.62 min; MS (M+H)$^+$=564) are combined and the solvent is removed in vacuo.

B.5.2. Experimental Procedure for the Synthesis of E-2b

B.5.3. Experimental Procedure for the Synthesis of I-13

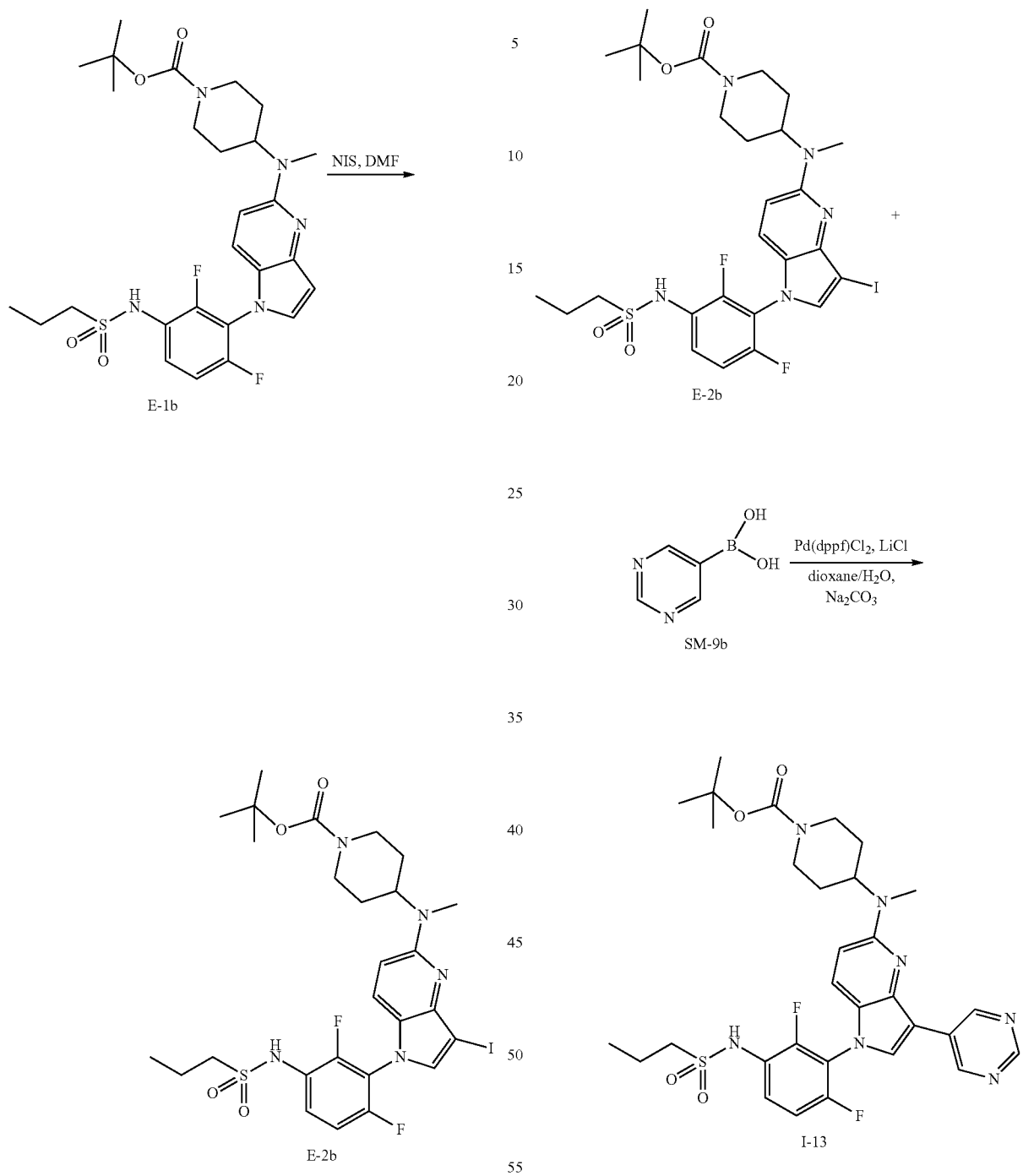

To a solution of sulfonamide E-1b (1.078 g, 1.9 mmol) in DMF (4 mL)/THF (100 μL) is added NIS (474 mg, 2.1 mmol) and the mixture is stirred for 1 h at rt. The reaction mixture is diluted with 30 mL DCM and extracted with NaHCO$_3$ solution (semiconc.). The combined organic layer is dried over MgSO$_4$, filtered and concentrated under reduced pressure. The residue is purified by column chromatography via RP HPLC. The product containing fractions of E-2b (HPLC-MS method C: $t_{Ret.}$=2.035 min; MS (M+H)$^+$=688) are freeze dried.

Sulfonamide E-2b (770 mg, 1.12 mmol), pyrimidin-5-yl-boronic acid (194 mg, 1.57 mmol), Pd(dppf)Cl$_2$ (82 mg, 0.11 mmol), LiCl (142 mg, 3.35 mmol) and Na$_2$CO$_3$ (294 mg, 2.8 mmol) are taken-up in dioxane/H$_2$O (2:1 mixture, 12 mL), and the resulting mixture is flushed with argon and stirred for 1 h at 100° C. The reaction mixture is diluted with DCM and extracted with NaHCO$_3$ solution (semiconc.). The organic layer is dried over MgSO$_4$, filtered, Isolute® is added, the solvent is removed in vacuo and the residue is purified via RP HPLC. The product containing fractions of I-13 (HPLC-MS method D: $t_{Ret.}$=2.149 min; MS (M+H)$^+$=642) are freeze dried.

B.6. Synthesis of Example Compound I-14
B.2.1. Experimental Procedure for the Synthesis of I-14

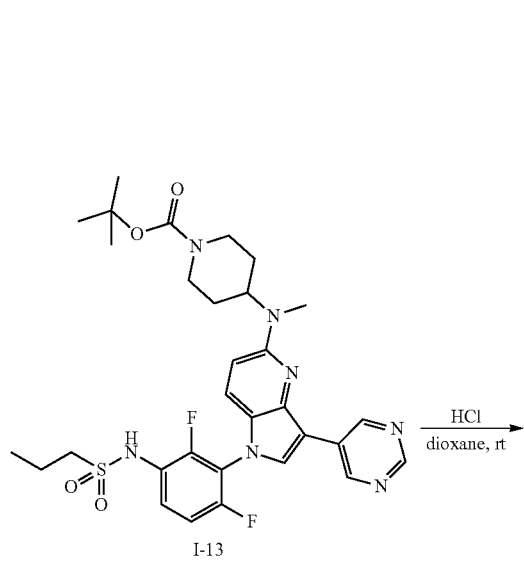

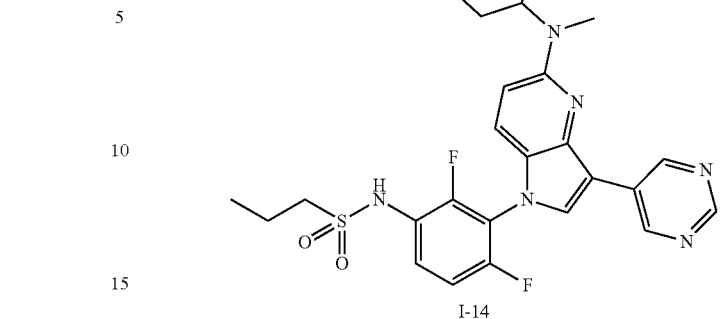

To a solution of example compound I-13 (154 mg, 0.24 mmol) in DCM/MeOH (1:1, 4 mL) is added HCl (in dioxane, 4 N, 2 mL) and the mixture is stirred for 3 h at rt. The solvent is removed in vacuo. Optained compound I-14 (HPLC-MS method C: $t_{Ret.}$=1.02 min; MS (M+H)$^+$=542) is used without further purification.

According to the synthesis of example compounds I-1 to I-4, I-13 and I-14 additional compounds (I) can be prepared using iodides IM-5 with the respective intermediates IM-1 to IM-4 in combination with the corresponding boronic acid derivative and optionally a suitable carbonyl derivative or alkylating agent for (reductive) alkylation.

TABLE 2

Structure and analytical data of example compounds I-1 to I-47

| # | structure | $t_{Ret.}$ (HPLC) [min] | MS (M + H)$^+$ |
|---|---|---|---|
| I-1 | 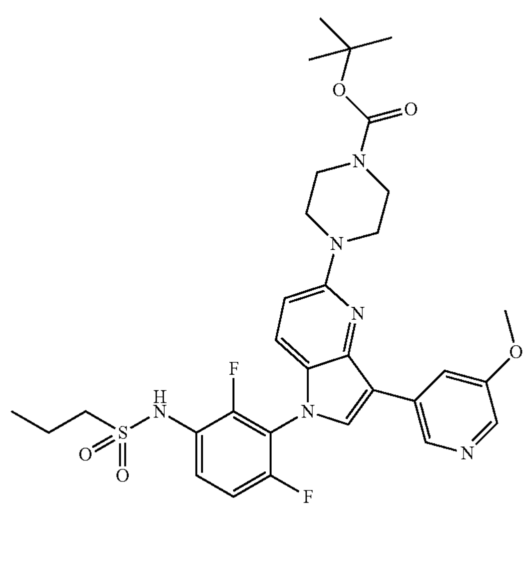 [SMILES: CCCS(=O)(=O)Nc1ccc(F)c(-n2cc(-c3cncc(OC)c3)c3nc(N4CCN(C(=O)OC(C)(C)C)CC4)ccc32)c1F] | 1.82 method B | 643 |

TABLE 2-continued

Structure and analytical data of example compounds I-1 to I-47

| # | structure | t$_{Ret.}$ (HPLC) [min] | MS (M + H)$^+$ |
|---|---|---|---|
| I-2 | 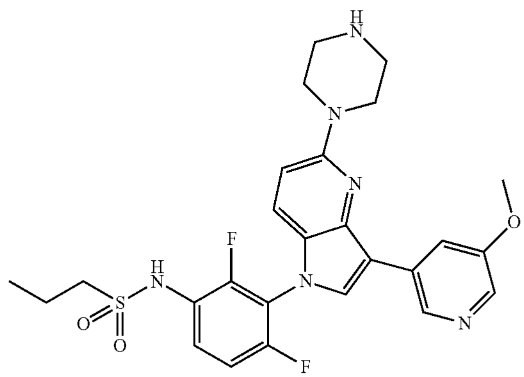 [SMILES: CCCS(=O)(=O)Nc1ccc(F)c(-n2cc(-c3cncc(OC)c3)c3nc(N4CCNCC4)ccc32)c1F] | 1.50 method B | 543 |
| I-3 | 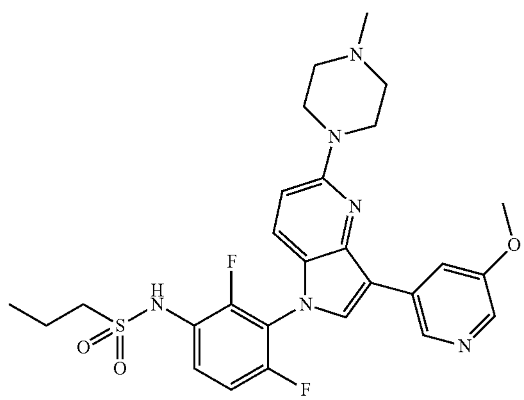 | 0.98 method C | 557 |
| I-4 | 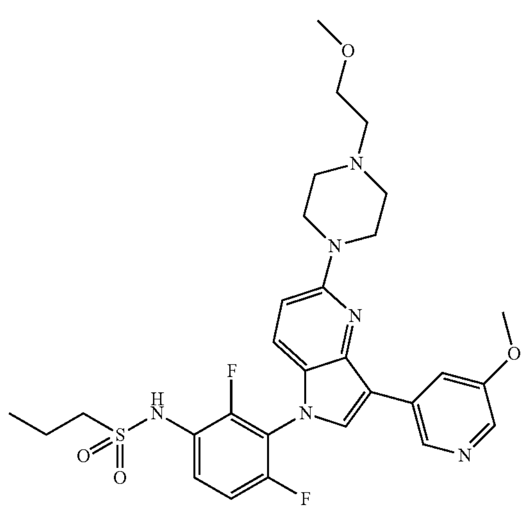 [SMILES: CCCS(=O)(=O)Nc1ccc(F)c(-n2cc(-c3cncc(OC)c3)c3nc(N4CCN(CCOC)CC4)ccc32)c1F] | 1.00 method C | 601 |

TABLE 2-continued

Structure and analytical data of example compounds I-1 to I-47

| # | structure | t_Ret. (HPLC) [min] | MS (M + H)+ |
|---|-----------|---------------------|-------------|
| I-5 | 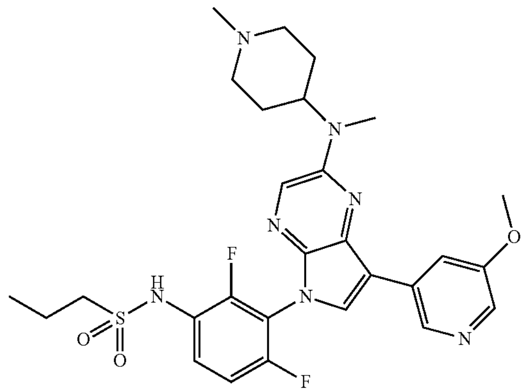 [SMILES: CCCS(=O)(=O)Nc1ccc(F)c(-n2cc(-c3cncc(OC)c3)c3nc(N(C)C4CCN(C)CC4)cnc32)c1F] | 1.03 method C | 586 |
| I-6 | 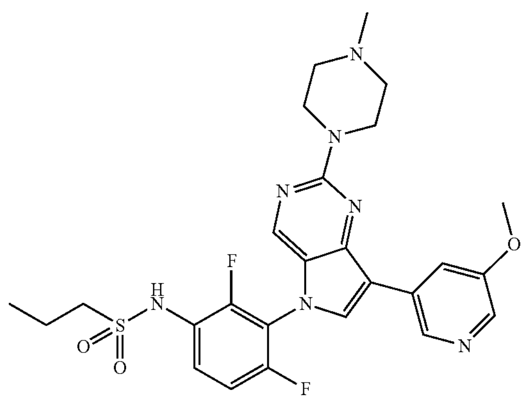 [SMILES: CCCS(=O)(=O)Nc1ccc(F)c(-n2cc(-c3cncc(OC)c3)c3nc(N4CCN(C)CC4)ncc32)c1F] | 1.02 method C | 558 |
| I-7 | 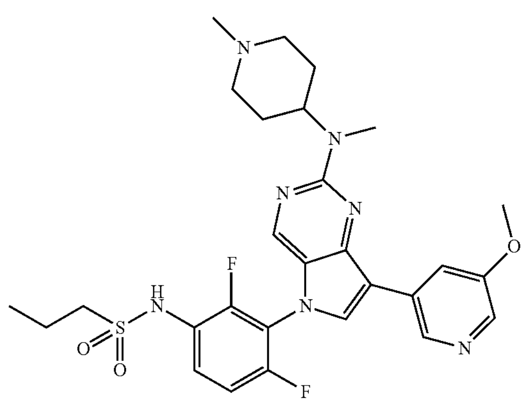 [SMILES: CCCS(=O)(=O)Nc1ccc(F)c(-n2cc(-c3cncc(OC)c3)c3nc(N(C)C4CCN(C)CC4)ncc32)c1F] | 1.03 method C | 586 |

TABLE 2-continued

Structure and analytical data of example compounds I-1 to I-47

| # | structure | t_Ret. (HPLC) [min] | MS (M + H)+ |
|---|---|---|---|
| I-8 | 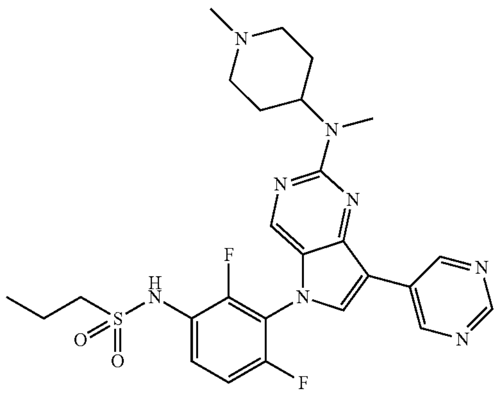 [SMILES: CCCS(=O)(=O)Nc1ccc(F)c(-n2cc(-c3cncnc3)c3nc(N(C)C4CCN(C)CC4)ncc32)c1F] | 0.92 method C | 557 |
| I-9[1] | 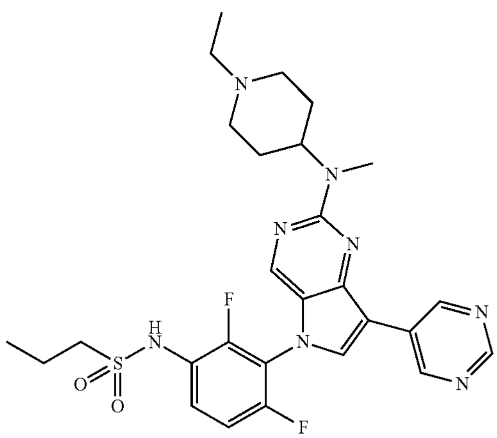 [SMILES: CCCS(=O)(=O)Nc1ccc(F)c(-n2cc(-c3cncnc3)c3nc(N(C)C4CCN(CC)CC4)ncc32)c1F] | 1.05 method C | 571 |
| I-10[2] | 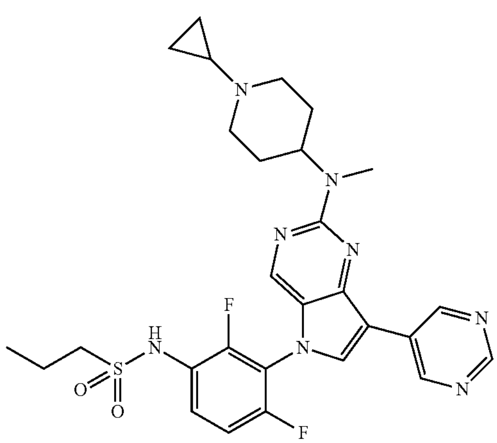 [SMILES: CCCS(=O)(=O)Nc1ccc(F)c(-n2cc(-c3cncnc3)c3nc(N(C)C4CCN(C5CC5)CC4)ncc32)c1F] | 1.10 method C | 583 |

TABLE 2-continued

Structure and analytical data of example compounds I-1 to I-47

| # | structure | t_Ret. (HPLC) [min] | MS (M + H)+ |
|---|---|---|---|
| I-11 | 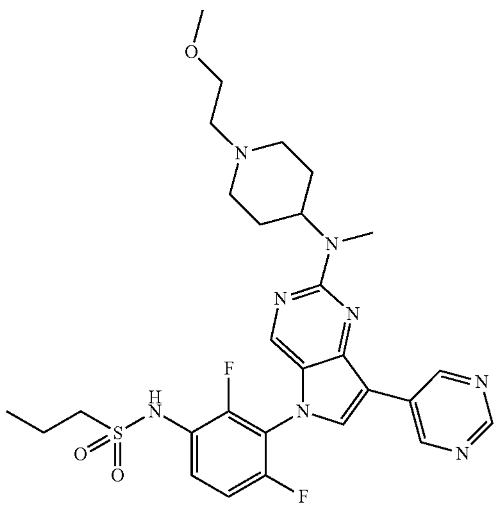 [SMILES: CCCS(=O)(=O)Nc1ccc(F)c(-n2cc(-c3cncnc3)c3nc(N(C)C4CCN(CCOC)CC4)ncc32)c1F] | 1.03 method C | 601 |
| I-12 | 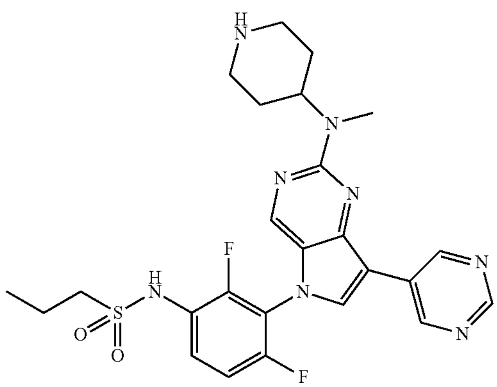 | 1.00 method C | 543 |
| I-13 | 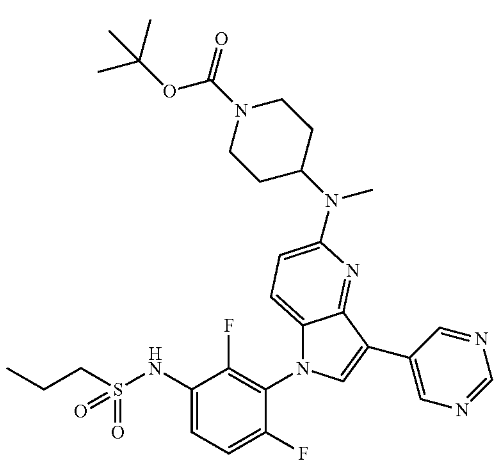 [SMILES: CCCS(=O)(=O)Nc1ccc(F)c(-n2cc(-c3cncnc3)c3nc(N(C)C4CCN(C(=O)OC(C)(C)C)CC4)ccc32)c1F] | 1.20 method C | 642 |

TABLE 2-continued

Structure and analytical data of example compounds I-1 to I-47

| # | structure | $t_{Ret.}$ (HPLC) [min] | MS $(M + H)^+$ |
|---|---|---|---|
| I-14 | 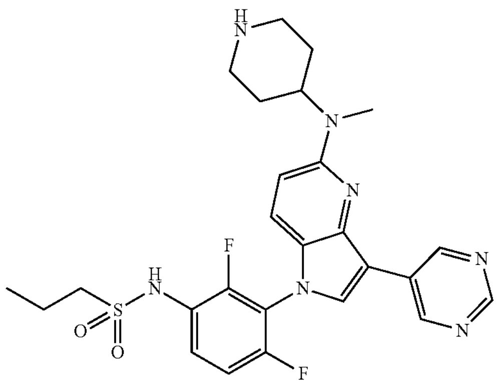 [SMILES: CCCS(=O)(=O)Nc1ccc(F)c(-n2cc(-c3cncnc3)c3nc(N(C)C4CCNCC4)ccc32)c1F] | 1.02 method C | 542 |
| I-15 | 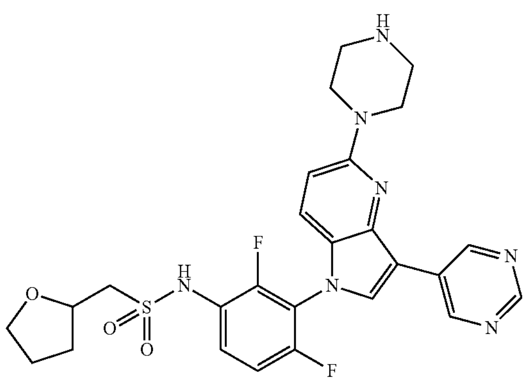 [SMILES: O=S(=O)(CC1CCCO1)Nc1ccc(F)c(-n2cc(-c3cncnc3)c3nc(N4CCNCC4)ccc32)c1F] | 0.95 method C | 556 |
| I-16[1] | 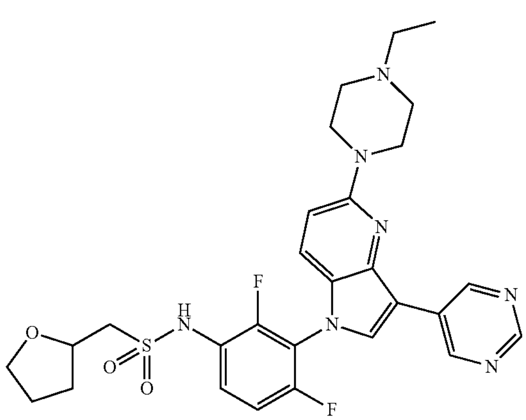 [SMILES: CCN1CCN(c2ccc3c(n2)c(-c2cncnc2)cn3-c2c(F)ccc(NS(=O)(=O)CC3CCCO3)c2F)CC1] | 0.98 method C | 584 |

TABLE 2-continued

Structure and analytical data of example compounds I-1 to I-47

| # | structure | t<sub>Ret.</sub> (HPLC) [min] | MS (M + H)⁺ |
|---|---|---|---|
| I-17 | 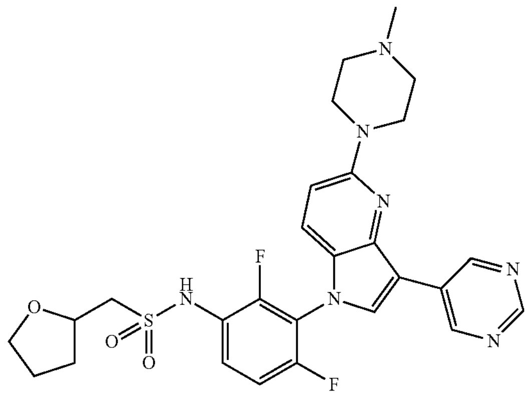 [SMILES: CN1CCN(c2ccc3c(n2)c(-c2cncnc2)cn3-c2c(F)ccc(NS(=O)(=O)CC3CCCO3)c2F)CC1] | 0.93 method C | 570 |
| I-18[1] | 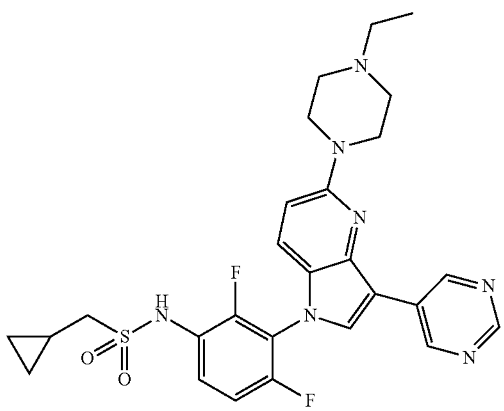 [SMILES: CCN1CCN(c2ccc3c(n2)c(-c2cncnc2)cn3-c2c(F)ccc(NS(=O)(=O)CC3CC3)c2F)CC1] | 1.01 method C | 554 |
| I-19 | 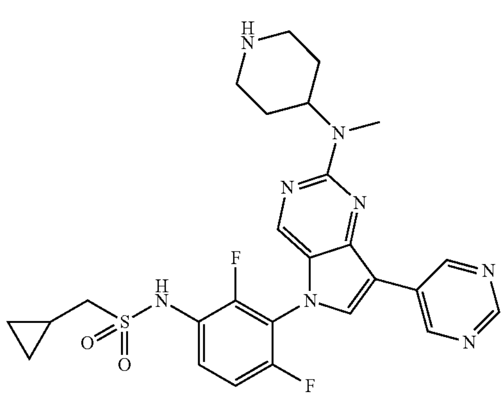 [SMILES: CN(c1ncc2c(n1)c(-c1cncnc1)cn2-c1c(F)ccc(NS(=O)(=O)CC2CC2)c1F)C1CCNCC1] | 0.93 method C | 555 |

TABLE 2-continued
Structure and analytical data of example compounds I-1 to I-47
| # | structure | $t_{Ret.}$ (HPLC) [min] | MS $(M + H)^+$ |
|---|---|---|---|
| I-20 | 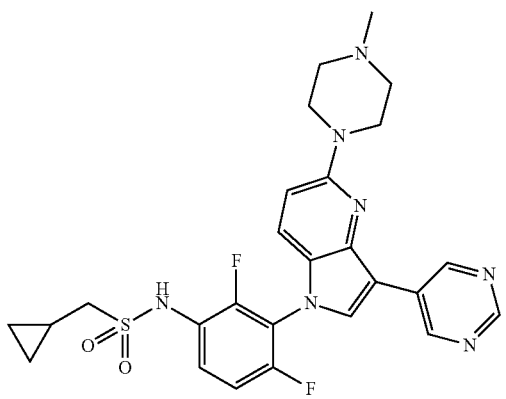 [SMILES: CN1CCN(c2ccc3c(n2)c(-c2cncnc2)cn3-c2c(F)ccc(NS(=O)(=O)CC3CC3)c2F)CC1] | 0.96 method C | 540 |
| I-21[1] | 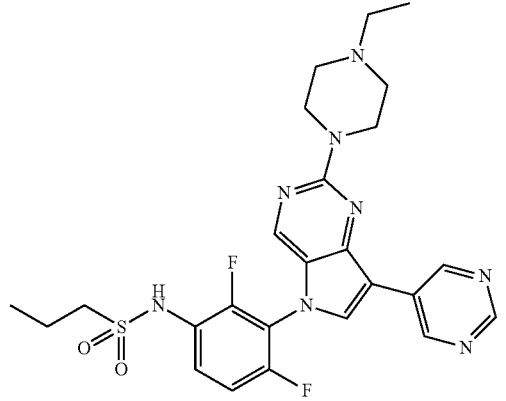 [SMILES: CCCS(=O)(=O)Nc1ccc(F)c(-n2cc(-c3cncnc3)c3nc(N4CCN(CC)CC4)ncc32)c1F] | 0.98 method C | 543 |
| I-22 | 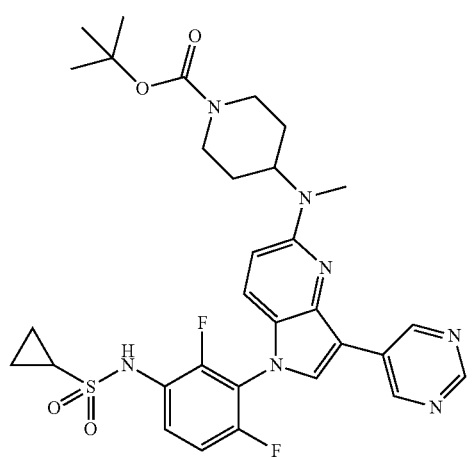 [SMILES: CN(c1ccc2c(n1)c(-c1cncnc1)cn2-c1c(F)ccc(NS(=O)(=O)C2CC2)c1F)C1CCN(C(=O)OC(C)(C)C)CC1] | 1.21 method C | 640 |

TABLE 2-continued

Structure and analytical data of example compounds I-1 to I-47

| # | structure | t_Ret. (HPLC) [min] | MS (M + H)+ |
|---|---|---|---|
| I-23 | 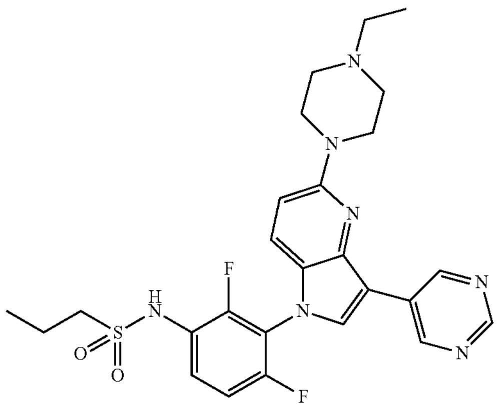 [SMILES: CCCS(=O)(=O)Nc1ccc(F)c(-n2cc(-c3cncnc3)c3nc(N4CCN(CC)CC4)ccc32)c1F] | 0.99 method C | 542 |
| I-24 | 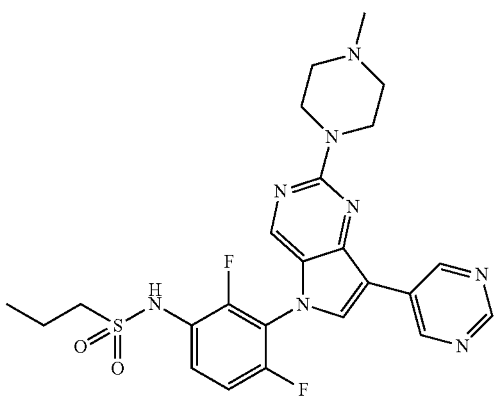 [SMILES: CCCS(=O)(=O)Nc1ccc(F)c(-n2cc(-c3cncnc3)c3nc(N4CCN(C)CC4)ncc32)c1F] | 0.93 method C | 529 |
| I-25 | 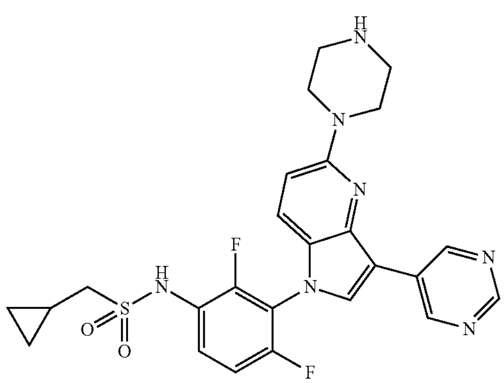 [SMILES: O=S(=O)(CC1CC1)Nc1ccc(F)c(-n2cc(-c3cncnc3)c3nc(N4CCNCC4)ccc32)c1F] | 0.89 method C | 526 |

TABLE 2-continued

Structure and analytical data of example compounds I-1 to I-47

| # | structure | t_Ret. (HPLC) [min] | MS (M + H)+ |
|---|---|---|---|
| I-26 | 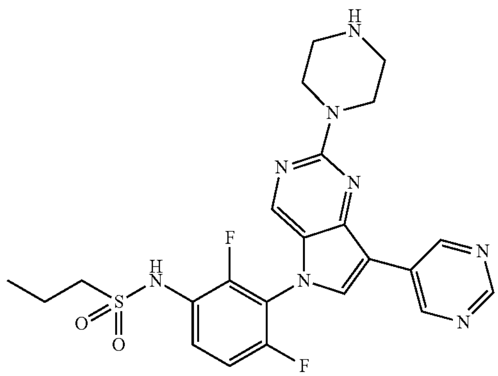 [SMILES: CCCS(=O)(=O)Nc1ccc(F)c(-n2cc(-c3cncnc3)c3nc(N4CCNCC4)ncc32)c1F] | 0.86 method C | 515 |
| I-27[3] | 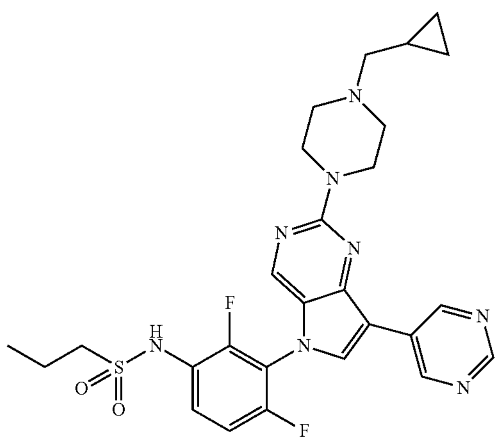 [SMILES: CCCS(=O)(=O)Nc1ccc(F)c(-n2cc(-c3cncnc3)c3nc(N4CCN(CC5CC5)CC4)ncc32)c1F] | 1.27 method C | 569 |
| I-28[3] | 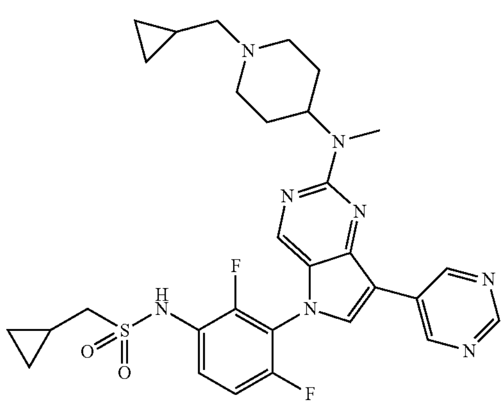 [SMILES: CN(c1ncc2c(n1)c(-c1cncnc1)cn2-c1c(F)ccc(NS(=O)(=O)CC2CC2)c1F)C1CCN(CC2CC2)CC1] | 1.09 method C | 609 |

TABLE 2-continued

Structure and analytical data of example compounds I-1 to I-47

| # | structure | $t_{Ret.}$ (HPLC) [min] | MS $(M + H)^+$ |
|---|---|---|---|
| I-29[2] | 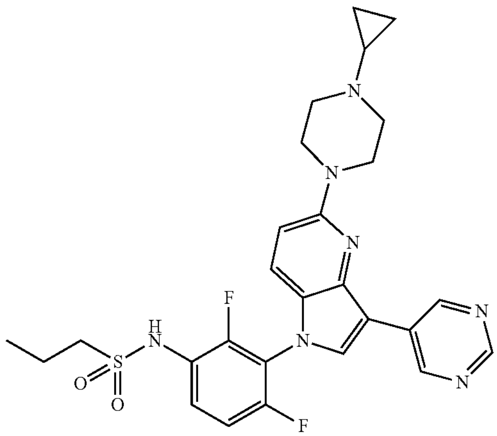 [SMILES: CCCS(=O)(=O)Nc1ccc(F)c(-n2cc(-c3cncnc3)c3nc(N4CCN(C5CC5)CC4)ccc32)c1F] | 1.10 method C | 554 |
| I-30 | 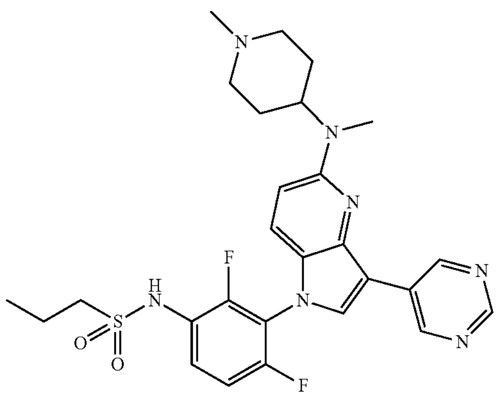 [SMILES: CCCS(=O)(=O)Nc1ccc(F)c(-n2cc(-c3cncnc3)c3nc(N(C)C4CCN(C)CC4)ccc32)c1F] | 1.01 method C | 556 |
| I-31[3] | 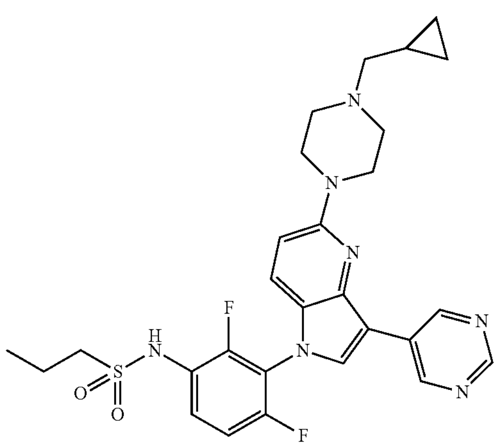 [SMILES: CCCS(=O)(=O)Nc1ccc(F)c(-n2cc(-c3cncnc3)c3nc(N4CCN(CC5CC5)CC4)ccc32)c1F] | 1.07 method C | 568 |

TABLE 2-continued

Structure and analytical data of example compounds I-1 to I-47

| # | structure | t$_{Ret.}$ (HPLC) [min] | MS (M + H)$^+$ |
|---|---|---|---|
| I-32 | 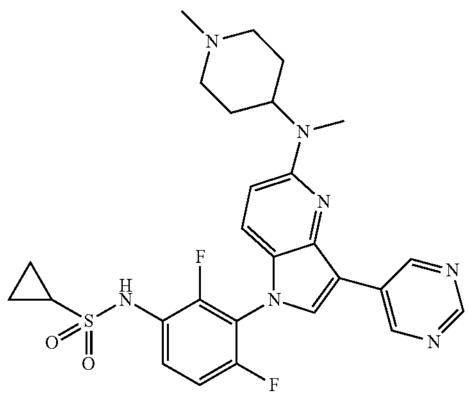 [SMILES: CN1CCC(N(C)c2ccc3c(n2)c(-c2cncnc2)cn3-c2c(F)ccc(NS(=O)(=O)C3CC3)c2F)CC1] | 0.97 method C | 554 |
| I-33 | 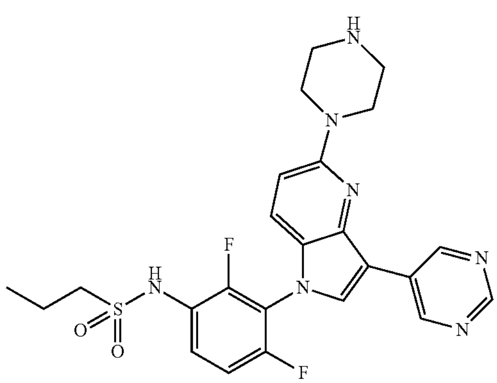 [SMILES: CCCS(=O)(=O)Nc1ccc(F)c(-n2cc(-c3cncnc3)c3nc(N4CCNCC4)ccc32)c1F] | 0.87 method C | 514 |
| I-34[4] | 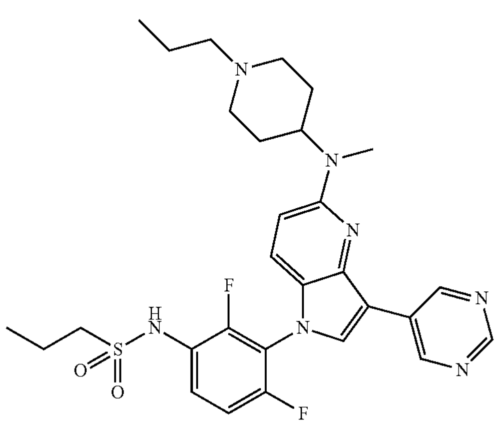 [SMILES: CCCN1CCC(N(C)c2ccc3c(n2)c(-c2cncnc2)cn3-c2c(F)ccc(NS(=O)(=O)CCC)c2F)CC1] | 1.12 method C | 584 |

TABLE 2-continued
Structure and analytical data of example compounds I-1 to I-47
| # | structure | t$_{Ret.}$ (HPLC) [min] | MS (M + H)$^+$ |
|---|---|---|---|
| I-35 | 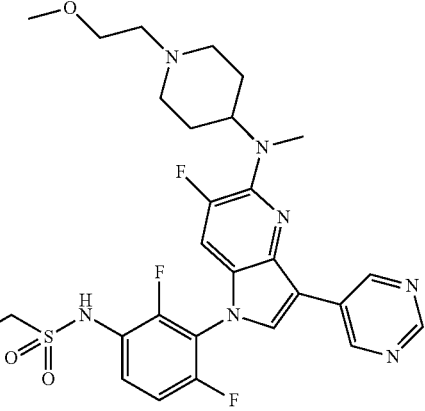 | 1.07 method C | 618 |
| I-36[5] | 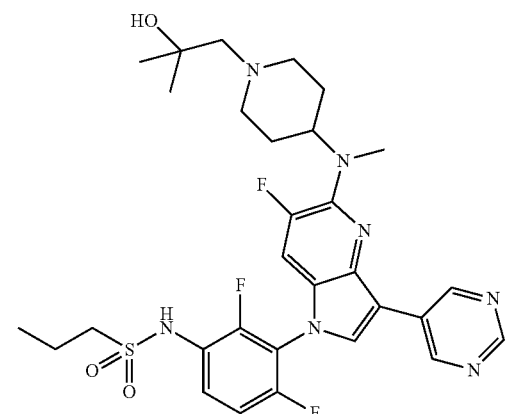 | 1.16 method C | 632 |
| I-37[3] | 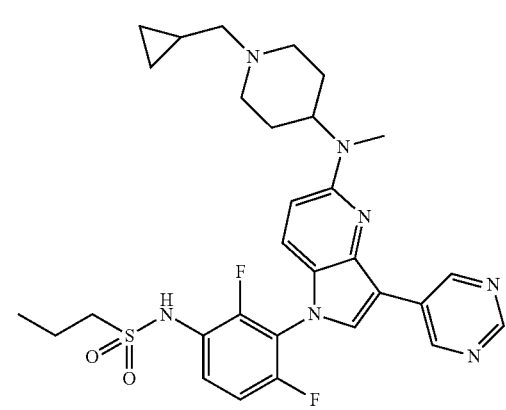 [SMILES: CCCS(=O)(=O)Nc1ccc(F)c(-n2cc(-c3cncnc3)c3nc(N(C)C4CCN(CC5CC5)CC4)ccc32)c1F] | 1.07 method C | 596 |

TABLE 2-continued

Structure and analytical data of example compounds I-1 to I-47

| # | structure | $t_{Ret.}$ (HPLC) [min] | MS $(M + H)^+$ |
|---|---|---|---|
| I-38[6] | 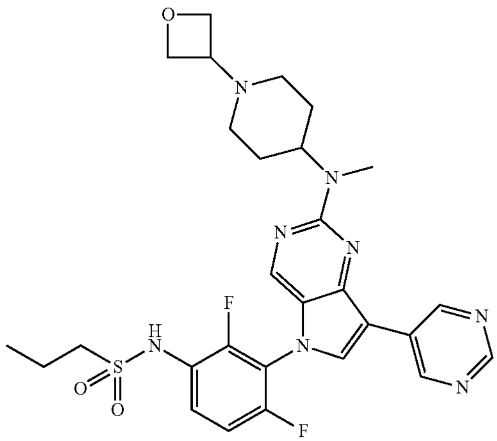 [SMILES: CCCS(=O)(=O)Nc1ccc(F)c(-n2cc(-c3cncnc3)c3nc(N(C)C4CCN(C5COC5)CC4)ncc32)c1F] | 0.95 method C | 599 |
| I-39[3] | 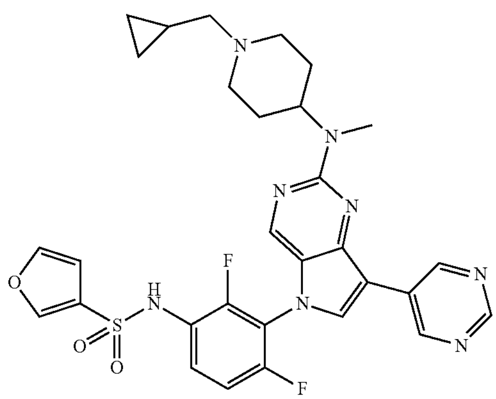 [SMILES: CN(c1ncc2c(n1)c(-c1cncnc1)cn2-c1c(F)ccc(NS(=O)(=O)c2ccoc2)c1F)C1CCN(CC2CC2)CC1] | 1.41 method C | 621 |
| I-40[1] | 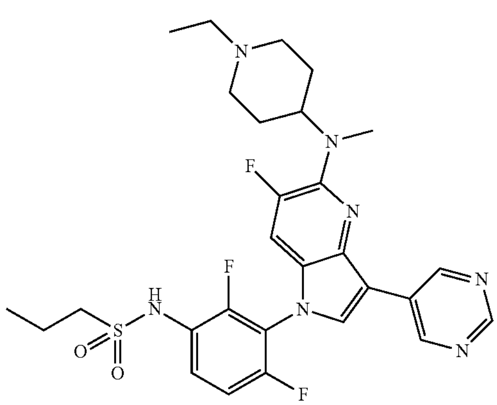 [SMILES: CCCS(=O)(=O)Nc1ccc(F)c(-n2cc(-c3cncnc3)c3nc(N(C)C4CCN(CC)CC4)c(F)cc32)c1F] | 1.06 method C | 588 |

TABLE 2-continued

Structure and analytical data of example compounds I-1 to I-47

| # | structure | $t_{Ret.}$ (HPLC) [min] | MS $(M + H)^+$ |
|---|---|---|---|
| I-41[1] | 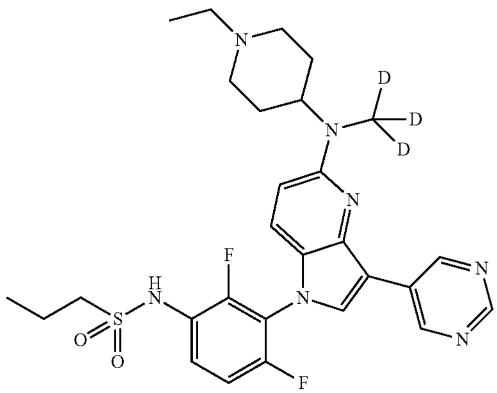 [SMILES: [2H]C([2H])([2H])N(c1ccc2c(n1)c(-c1cncnc1)cn2-c1c(F)ccc(NS(=O)(=O)CCC)c1F)C1CCN(CC)CC1] | 0.84 method C | 573 |
| I-42[1] | 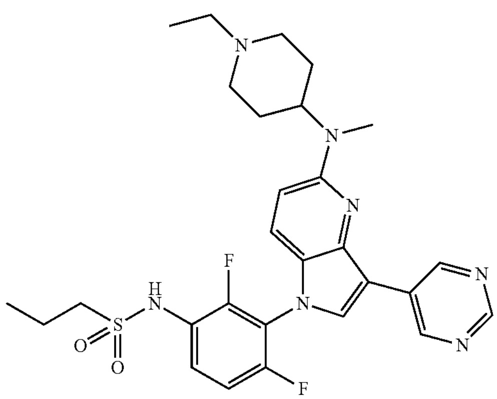 [SMILES: CCCS(=O)(=O)Nc1ccc(F)c(-n2cc(-c3cncnc3)c3nc(N(C)C4CCN(CC)CC4)ccc32)c1F] | 0.85 method C | 570 |
| I-43[3] | 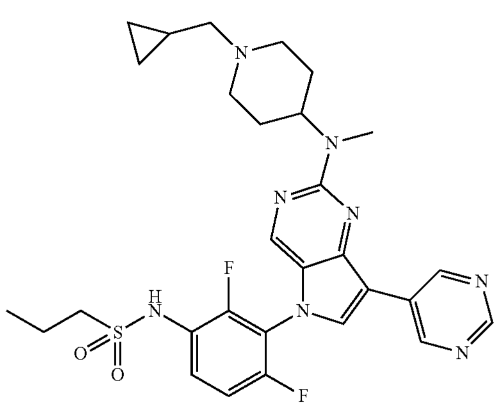 [SMILES: CCCS(=O)(=O)Nc1ccc(F)c(-n2cc(-c3cncnc3)c3nc(N(C)C4CCN(CC5CC5)CC4)ncc32)c1F] | 1.08 method C | 597 |

TABLE 2-continued
Structure and analytical data of example compounds I-1 to I-47
| # | structure | t_Ret. (HPLC) [min] | MS (M + H)+ |
|---|---|---|---|
| I-44[7] | 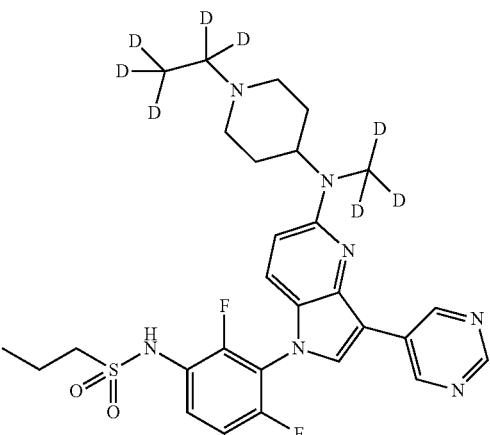 | 1.01 method C | 578 |
| I-45[5] | 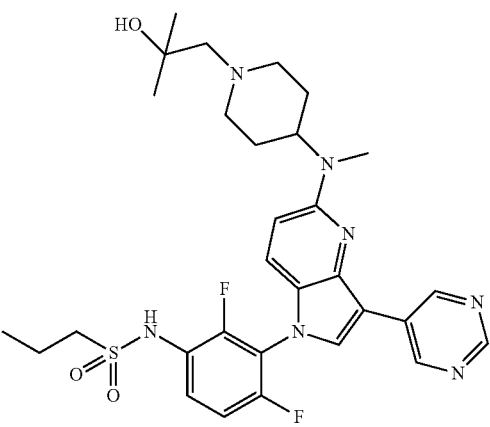 [SMILES: CCCS(=O)(=O)Nc1ccc(F)c(-n2cc(-c3cncnc3)c3nc(N(C)C4CCN(CC(C)(C)O)CC4)ccc32)c1F] | 1.13 method C | 614 |
| I-46[7] | 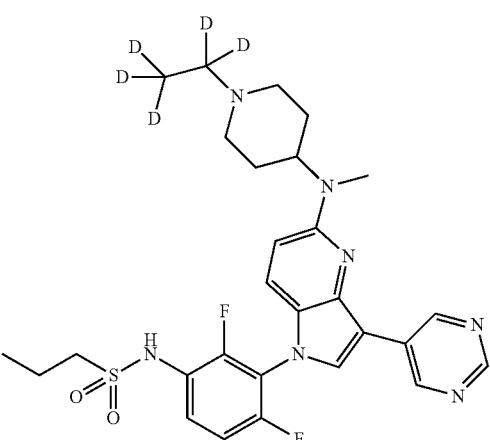 | 1.02 method C | 575 |

TABLE 2-continued

Structure and analytical data of example compounds I-1 to I-47

| # | structure | $t_{Ret.}$ (HPLC) [min] | MS $(M + H)^+$ |
|---|-----------|---|---|
| I-47[1] | 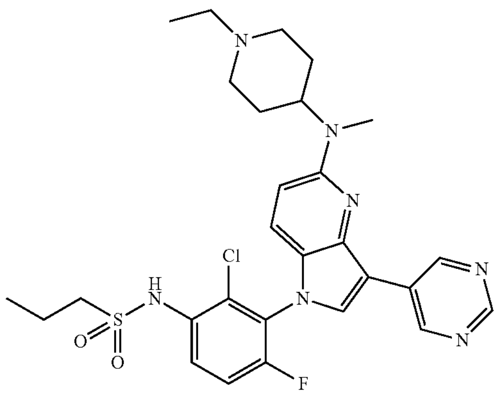 [SMILES: CCCS(=O)(=O)Nc1ccc(F)c(-n2cc(-c3cncnc3)c3nc(N(C)C4CCN(CC)CC4)ccc32)c1Cl] | 1.03 method C | 586 |

[1]obtained via reductive alkylation with acetaldehyde
[2]obtained via reductive alkylation with 1-methoxy-1-[(trimethylsilyl)oxy]-cyclopropane
[3]obtained via reductive alkylation with cyclopropanecarbaldehyde
[4]obtained via reductive alkylation with propanal
[5]obtained via ring opening with 2,2-dimethyloxirane
[6]obtained via reductive alkylation with oxetan-3-one
[7]obtained via alkylation with 1,1,1,2,2-pentadeuterio-2-iodo-ethane The following examples describe the biological activity of the compounds according to the invention without restricting the invention to these examples. Compounds of general formula (I) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

Kinase test B-Raf (V600E)

In a dilution series 10 µL/well of test substance solution are placed in a multiwell plate. The dilution series is selected so that generally a range of concentrations of 2 µM to 0.119 nM or 0.017 nM is covered. If necessary the initial concentration of 2 µM is changed to 50 µM, 10 µM, 0.4 µM or 0.2857 µM and further dilution is carried out accordingly. The final concentration of DMSO is 5%. 10 µL/well of the B-Raf (V600E)-kinase solution are pipetted in (containing 0.5 ng B-Raf (V600E)-kinase, e.g. from Upstate) in 20 mM Tris-HCl pH 7.5, 0.1 mM EDTA, 0.1 mM EGTA, 0.286 mM sodium orthovanadate, 10% glycerol, 1 mg/mL bovine serum albumin, 1 mM dithiothreitol) and the mixture is incubated for 1 h at RT with shaking. The kinase reaction is started by the addition of 20 µL/well ATP solution [final concentration: 250 µM ATP, 30 mM Tris-HCl pH 7.5, 0.02% Brij, 0.2 mM sodium orthovanadate, 10 mM magnesium acetate, 0.1 mM EGTA, phosphatase cocktail (Sigma, #P2850, dilution recommended by the manufacturer)] and 10 µL/well MEK1 solution [containing 50 ng biotinylated MEK1 (prepared from purified MEK1 according to standard procedure, e.g. with EZ-Link Sulpho-NHS-LC-Biotin reagent, Pierce, #21335)] and carried out for 60 min at RT with constant shaking. The reaction is stopped by the addition of 12 µL/well of a 100 mM EDTA solution and incubation is continued for a further 5 min. 55 µL/well of the reaction solution are transferred into a streptavidin-coated plate (e.g. Streptawell HighBond, Roche, #11989685001) and gently shaken for 1 h at RT in order to bind biotinylated MEK1 to the plate. After elimination of the liquid the plate is washed five times with 200 µL/well of 1×PBS and 100 µL/well solution of primary antibody plus europium-labelled secondary antibody [Anti Phospho-MEK (Ser217/221), Cell Signaling, #9121 and Eu—N1 labelled goat-anti-rabbit antibody, Perkin Elmer, #AD0105] is added, the primary antibody is diluted 1:2000 and the secondary antibody is diluted to 0.4-0.5 µg/mL in Delfia Assay Buffer (Perkin Elmer, #1244-111). After 1 h shaking at RT the solution is poured away and washed five times with 200 µL/well Delfia Wash Buffer (Perkin Elmer, #4010-0010/#1244-114). After the addition of 200 µL/well Enhancement Solution (Perkin Elmer, #4001-0010/#1244-105) the mixture is shaken for 10 min at RT and then measured in a Wallac Victor using the program "Delfia Time Resolved Fluorescence (Europium)". $IC_{50}$ values are obtained from these dosage-activity curves using a software program (GraphPadPrizm).

TABLE 3

$IC_{50}$ B-Raf V600E

| # | B-RAF $IC_{50}$ [nM] |
|---|---|
| I-3 | 297 |
| I-4 | 125 |
| I-5 | 16 |
| I-6 | 1613 |
| I-7 | 7 |
| I-8 | 4 |
| I-9 | 16 |
| I-10 | 29 |
| I-11 | 42 |
| I-12 | 41 |

Measurement of the Inhibition of the Proliferation of Cultivated Human Melanoma cells (SK-MEL-28, B-RAF$^{V600E}$ Mutated)

For measuring the proliferation of cultivated human tumour cells, cells of the melanoma cell line SK-MEL-28

[from American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, #BE13-114E) and 2 mM glutamine. SK-MEL-28 cells are placed in 96-well flat bottomed dishes in a density of 2500 cells per well in supplemented MEM medium (see above) and incubated overnight in an incubator (at 37° C. and 5% $CO_2$). The active substances are added to the cells in different concentrations, so that a concentration range of 50 µM to 3.2 nM is covered. If necessary the initial concentration of 50 µM is changed to 10 µM or 2 µM and further dilution is carried out accordingly (up to 0.6 nM or 0.12 nM). After an incubation period of a further 72 h 20 µL AlamarBlue reagent (Serotec Ltd., #BUF012B) are added to each well and the cells are incubated for a further 3-6 h. The colour change of the AlamarBlue reagent is determined in a fluorescence spectrophotometer (e.g. Gemini, Molecular Devices). $EC_{50}$ values are calculated using a software program (GraphPadPrizm).

The $EC_{50}$ values of example compounds determined using the above assay are shown in Table 4.

TABLE 4

| # | SK-MEL-28 $EC_{50}$ [nM] |
| --- | --- |
| I-3 | 114 |
| I-4 | 63 |
| I-5 | 41 |
| I-6 | 121 |
| I-7 | 40 |
| I-8 | 6 |
| I-9 | 11 |
| I-11 | 21 |
| I-12 | 60 |
| I-13 | 86 |
| I-14 | 6 |
| I-15 | 181 |
| I-16 | 491 |
| I-17 | 386 |
| I-18 | 90 |
| I-19 | 110 |
| I-20 | 72 |
| I-21 | 89 |
| I-22 | 112 |
| I-23 | 40 |
| I-24 | 68 |
| I-25 | 27 |
| I-26 | 73 |
| I-27 | 54 |
| I-28 | 7 |
| I-29 | 41 |
| I-30 | 2 |
| I-31 | 31 |
| I-32 | 2 |
| I-33 | 14 |
| I-34 | 2 |
| I-35 | 6 |
| I-36 | 7 |
| I-37 | 2 |
| I-38 | 5 |
| I-39 | 0.47 |
| I-40 | 3 |
| I-41 | 1 |
| I-42 | 0.84 |
| I-43 | 5 |
| I-44 | 1 |
| I-45 | 5 |
| I-46 | 3 |
| I-47 | 2 |

Measurement of the Inhibition of the Proliferation of Cultivated Human Melanoma cells (A375, B-RAF$^{V600E}$ Mutated)

For measuring the proliferation of cultivated human tumour cells, cells of the melanoma cell line A375 [from the American Type Culture Collection (ATCC)] are cultivated in DMEM medium, supplemented with 10% foetal calf serum and 2% sodium bicarbonate. Test substances are tested on A375 cells according to the procedure described for SK-MEL-28 cells (see above), but seeding them at 5000 cells per well.

Most of the example compounds I-1 to I-47 show very good activity in the cellular A375 assay, i.e. an $EC_{50}$ value of less than 500 nM, generally less than 100 nM.

The active substances are characterised in that they have a significantly lower antiproliferative activity on cell lines which have no B-RAF mutation. Thus, for example, example compounds I-1 to I-47 have an $EC_{50}$ value on melanoma cells (e.g. A375) without a B-Raf V600E mutation which is generally higher than that of B-RAF mutated melanoma cells (e.g. A375) by at least a factor of 100.

The $EC_{50}$ value of the phospho-ERK reduction and the $EC_{50}$ value of the antiproliferative activity in B-RAF mutated cell lines correlate well with cellular selectivity of the active substances.

Measurement of the Reduction of the Phospho-ERK Signal in Cultivated Human Melanoma Cells (SK-MEL-28, B-RAF$^{V600E}$ Mutated)

To measure the reduction in the phospho-ERK signal of cultivated human tumour cells, cells of the melanoma cell line SK-MEL-28 [from the American Type Culture Collection (ATCC)] in MEM medium, supplemented with 10% foetal calf serum, 2% sodium bicarbonate, 1 mM sodium pyruvate, 1% non-essential amino acids (e.g. obtained from Cambrex, #BE13-114E) and 2 mM glutamine, are cultivated. SK-MEL-28 cells are placed in 96-well flat bottomed dishes in a density of 7500 cells per well in supplemented MEM medium (see above) and incubated overnight in an incubator (at 37° C. and 5% $CO_2$). The active substances are added to the cells in different concentrations, so that a concentration range of 10 µM to 2.4 nM is covered. If necessary the initial concentration of 10 µM is changed to 50 µM or 2.5 µM and further dilution is carried out accordingly (up to 12.2 nM or 0.6 nM). After an incubation period of a further 2 h the cells are fixed with 4% formaldehyde and permeabilised with 0.1% Triton X-100 in PBS. Non-specific antibody binding is reduced by incubating with 5% skimmed milk powder dissolved in TBS-T. Phosphorylated ERK is detected with a murine monoclonal anti-diphosphorylated ERK½ antibody (from Sigma, #M8159). After washing steps using 0.1% Tween 20 in PBS the bound first antibody is detected by the second antibody (peroxidase coupled polyclonal rabbit anti mouse IgG from DAKO #P0161). After further washing steps the substrate (TMB Peroxidase Substrate Solution made by Bender MedSystems #BMS406) is added. The colour reaction is stopped after a few minutes with 1 M phosphoric acid. The staining is measured at 450 nm with a Spectra Max Plus reader made by Molecular Devices. $EC_{50}$ values are calculated using a software program (GraphPadPrizm).

The $EC_{50}$ value of the phospho-ERK reduction of the example compounds determined using the above assay is generally less than 100 nM.

The substances of the present invention are B-RAF-kinase inhibitors. As can be demonstrated by DNA staining followed by FACS or Cellomics Array Scan analysis, the inhibition of proliferation achieved by means of the compounds according to the invention is brought about above all by preventing entry into the DNA synthesis phase. The treated cells arrest in the G1 phase of the cell cycle.

Accordingly, the compounds according to the invention are also tested on other tumour cells. For example these compounds are effective on colon carcinoma lines, e.g. Colo205, HT29, and may be used in this and other indications. This demonstrates the usefulness of the compounds according to the invention for the treatment of different types of tumours.

On the basis of their biological properties the compounds of general formula (I) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto:

brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma, vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); tubuline inhibitors; PARP inhibitors, topoisomerase inhibitors (e.g. epipodophyllotoxins such as for example etoposide and etopophos, teniposide, amsacrin, topotecan, irinotecan, mitoxantron), serine/threonine kinase inhibitors (e.g. PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP, Mcl-1, MDM2/MDMX), MEK inhibitors, ERK inhibitors, IGF-1R inhibitors, ErbB receptor inhibitors, rapamycin analogs (e.g. everolimus, temsirolimus, ridaforolimus, sirolimus) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexafin gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEX$^{GM-CSF}$, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PDO325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhuMAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporfin, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZDI839, ZSTK-474, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |

-continued

| B) | Tablets | per tablet |
|---|---|---|
| | sodiumcarboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of the formula (I)

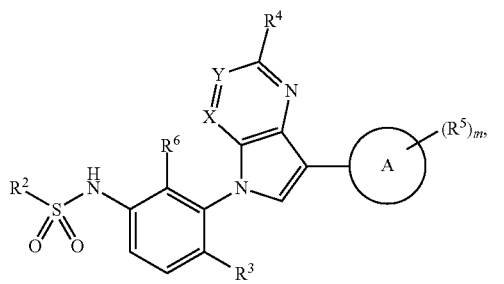

(I)

wherein
R$^2$ is a group optionally substituted by one or more, identical or different R$^{b1}$ and/or R$^{c1}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-10 membered heterocyclyl or R$^2$ is —NR$^{c1}$R$^{c1}$;
each R$^{b1}$ is independently selected from among —OR$^{c1}$, —NR$^{c1}$R$^{c1}$ halogen, —CN, —C(O)R$^{c1}$, C(O)OR$^{c1}$, —C(O)NR$^{c1}$R$^{c1}$, —S(O)$_2$R$^{c1}$; —S(O)$_2$NR$^{c1}$R$^{c1}$, —NHC(O)R$^{c1}$ and —N(C$_{1-4}$alkyl)C(O)R$^{c1}$ as well as the bivalent substituent =O, wherein the latter may only be a substituent in non-aromatic ring systems;
each R$^{c1}$ independently of one another denotes hydrogen or a group selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-10 membered heterocyclyl;

R$^3$ is selected from halogen,
R$^4$ is a 4-7 membered, nitrogen-containing heterocyclyl optionally substituted by one or more, identical or different R$^{a2}$ and/or R$^{b2}$,
or
R$^4$ is —NR$^{a3}$R$^{a3}$;
each R$^{a2}$ independently of one another denotes a group optionally substituted by one or more, identical or different R$^{b2}$ and/or R$^{c2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl and 3-10 membered heterocyclyl;
each R$^{b2}$ is independently selected from among —OR$^{c2}$, —NR$^{c2}$R$^{c2}$, halogen, —C(O)R$^{c2}$, —C(O)OR$^{c2}$, —C(O)NR$^{c2}$R$^{c2}$, —CN, —NHC(O)R$^{c2}$ and —NHC(O)OR$^2$;
each R$^{c2}$ independently of one another denotes hydrogen or a group selected from among C$_{1-6}$alkyl, C$_{2-6}$alkenyl, C$_{2-6}$alkynyl, C$_{3-6}$cycloalkyl, C$_{4-6}$cycloalkenyl and 3-10 membered heterocyclyl, wherein this heterocyclyl is optionally substituted by one or more, identical or different substituents selected from among halogen, C$_{1-6}$alkyl and —C(O)—C$_{1-6}$alkyl;
each R$^{a3}$ independently of one another denotes hydrogen or a group optionally substituted by one or more, identical or different R$^{b3}$ and/or R$^{c3}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl and 3-10 membered heterocyclyl;
each R$^{b3}$ is independently selected from among —OR$^{c3}$, —NR$^{c3}$R$^{c3}$, halogen, —C(O)R$^{c3}$, —C(O)OR$^{c3}$, —C(O)NR$^{c3}$R$^{c3}$, —CN, —NHC(O)R$^{c3}$ and —NHC(O)OR$^{c3}$;
each R$^{c3}$ independently of one another denotes hydrogen or a group selected from among C$_{1-6}$alkyl, C$_{2-6}$alkenyl, C$_{2-6}$alkynyl, C$_{3-6}$cycloalkyl, C$_{4-6}$cycloalkenyl, C$_{1-6}$alkyl-O—C$_{1-6}$alkyl, (C$_{1-4}$alkyl)HN—C$_{1-6}$alkyl, (C$_{1-4}$alkyl)$_2$N—C$_{1-6}$alkyl, C$_{1-6}$haloalkyl, 4-16 membered heterocyclylalkyl and 3-10 membered heterocyclyl, wherein the heterocyclyl ring in aforementioned groups is optionally substituted by one or more, identical or different C$_{1-6}$alkyl;
ring A is a 5-10 membered heteroaryl;
m denotes the number 0, 1 or 2;
each R$^5$ independently of one another denotes a group optionally substituted by one or more, identical or different R$^{a4}$ and/or R$^{b4}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-11 membered heterocyclyl, or is independently selected from among —OR$^{a5}$, —NR$^{a5}$R$^{a5}$, —N(OR$^{a5}$)R$^{a5}$, halogen, —CN, —C(O)R$^{a5}$, —C(O)OR$^{a5}$, —C(O)NR$^{a5}$R$^{a5}$, —C(NH)NR$^{a5}$R$^{a5}$, —S(O)$_2$NR$^{a5}$R$^{a5}$, —NHS(O)$_2$R$^{a5}$, —N(C$_{1-4}$alkyl)S(O)$_2$R$^{a5}$, —NHS(O)$_2$NR$^{a5}$R$^{a5}$, —NHC(O)R$^{a5}$, —N(C$_{1-4}$alkyl)C(O)R$^{a5}$, —NHC(O)OR$^{a5}$, —N(C$_{1-4}$alkyl)C(O)OR$^{a5}$, —NHC(O)NR$^{a5}$R$^{a5}$ and —N(C$_{1-4}$alkyl)C(O)NR$^{a5}$R$^{a5}$;
each R$^{a4}$ independently of one another denotes a group optionally substituted by one or more, identical or different R$^{b4}$ and/or R$^{c4}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl and 3-10 membered heterocyclyl;
each R$^{b4}$ is independently selected from among —OR$^{c4}$, —NR$^{c4}$R$^{c4}$, halogen, —C(O)R$^{c4}$, —C(O)OR$^{c4}$, —C(O)NR$^{c4}$R$^{c4}$, —CN, —NHC(O)R$^{c4}$ and —NHC(O)OR$^{c4}$;

each $R^{c4}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl;

each $R^{a5}$ independently of one another denotes hydrogen or a group optionally substituted by one or more, identical or different $R^{b5}$ and/or $R^{c5}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b5}$ is independently selected from among —$OR^{c5}$, —$NR^{c5}R^{c5}$, halogen, —C(O)$R^{c5}$, —C(O)$OR^{c5}$, —C(O)$NR^{c5}R^{c5}$, —CN, —NHC(O)$R^{c5}$ and —NHC(O)$OR^{c5}$;

each $R^{c5}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O—$C_{1-6}$alkyl, ($C_{1-4}$alkyl)HN—$C_{1-6}$alkyl, ($C_{1-4}$alkyl)$_2$N—$C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl;

X and Y are either both CH or one is CH and the other is CF or one is CH and the other is N;

$R^6$ is chlorine or fluorine;

wherein the compounds (I) may also be present in the form of the tautomers, racemates, enantiomers, diastereomers and the mixtures thereof or as the respective salts of all the above-mentioned forms.

2. The compound according to claim 1, wherein
$R^2$ is selected from among $C_{1-6}$alkyl, 5-6 membered heteroaryl, $C_{3-6}$cycloalkyl and $C_{4-7}$cycloalkylalkyl.

3. The compound according to claim 2, wherein
$R^2$ denotes $C_{1-6}$alkyl.

4. The compound according to claim 3, wherein
$R^2$ is selected from among ethyl, n-propyl, iso-propyl and iso-butyl.

5. The compound according to claim 4, wherein
$R^2$ is n-propyl.

6. The compound according to claim 2, wherein
$R^2$ denotes cyclopropyl or cyclopropylmethyl.

7. The compound according to claim 2, wherein
$R^2$ denotes furyl.

8. The compound according to claim 1, wherein
$R^3$ is fluorine.

9. The compound according to claim 1, wherein
ring A is a nitrogen-containing 5-10 membered heteroaryl.

10. The compound according to claim 9, wherein ring A is a nitrogen-containing 5-6 membered heteroaryl.

11. The compound according to claim 10, wherein
ring A is selected from among pyridyl and pyrimidyl.

12. The compound according to claim 11, wherein
ring A is pyridyl.

13. The compound according to claim 11, wherein
ring A is pyrimidyl.

14. The compound according to claim 1, wherein
m is 0.

15. The compound according to claim 1, wherein
m is 1.

16. The compound according to claim 1, wherein
m denotes 1;
$R^5$ and ring A together is

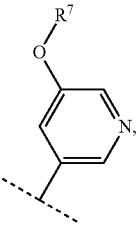

wherein
$R^7$ is $C_{1-6}$alkyl.

17. The compound according to claim 16, wherein
m denotes 1 and
$R^5$ and ring A together is

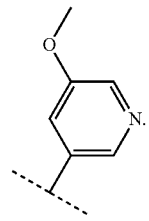

18. The compound according to claim 1, wherein
m denotes 0 and
ring A is

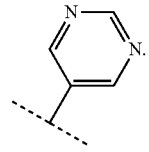

19. The compound according to claim 1, wherein
X is CH and Y is CH.

20. The compound according to claim 1, wherein
X is CH and Y is N.

21. The compound according to claim 1, wherein
X is N and Y is CH.

22. The compound according to claim 1, wherein
X is CH and Y is CF.

23. The compound according to claim 1, wherein
$R^4$ is selected from among piperazinyl, piperidinyl and morpholinyl, all optionally substituted by one or more, identical or different $R^{a2}$ and/or $R^{b2}$ each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b2}$ is independently selected from among —$OR^{c2}$, —$NR^{c2}R^{c2}$, halogen, —C(O)$R^{c2}$, —C(O)$OR^{c2}$, —C(O)$NR^{c2}R^{c2}$, —CN, —NHC(O)$R^2$ and —NHC(O)$OR^{c2}$, and each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

24. The compound according to claim 23, wherein
$R^4$ is selected from among piperazinyl, piperidinyl and morpholinyl, all bound to the azaindole ring system via a nitrogen atom and all optionally substituted by one or more, identical or different $R^{a2}$ and/or $R^{b2}$
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —NHC(O)$OR^{c2}$, and
each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

25. The compound according to claim 24, wherein
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl and 3-10 membered heterocyclyl;
each $R^{b2}$ is independently selected from among —$OR^{c2}$, —$NR^{c2}R^{c2}$, halogen, —$C(O)NR^{c2}R^{c2}$, and —CN, and
each $R^{c2}$ independently of one another denotes hydrogen or a group selected from among $C_{1-6}$alkyl, $C_{3-6}$cycloalkyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

26. The compound according to claim 1, wherein
$R^4$ is

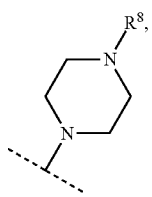

wherein
$R^8$ is selected from among $C_{1-6}$alkyl, $C_{3-6}$cycloalkyl, $C_{3-6}$cycloalkyl-$C_{1-6}$alkyl, —C(O)$C_{1-6}$alkyl and $C_{1-6}$alkyloxy-$C_{1-6}$alkyl.

27. The compound according to claim 1, wherein
$R^4$ is —$NR^9R^{10}$;
$R^9$ is $C_{1-6}$alkyl and
$R^{10}$ is 3-7 membered, nitrogen-containing heterocyclyl, optionally substituted by one or more, identical or different substituents selected from among $C_{1-6}$alkyl, $C_{3-6}$cycloalkyl, —C(O)$C_{1-6}$alkyl and $C_{1-6}$alkyloxy-$C_{1-6}$alkyl.

28. The compound according to claim 27, wherein
$R^4$ is

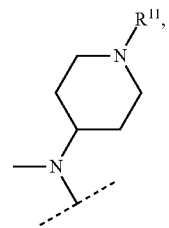

wherein
$R^{11}$ is selected from among $C_{1-6}$alkyl, $C_{3-6}$cycloalkyl, C(O)$C_{1-6}$alkyl and $C_{1-6}$alkyloxy-$C_{1-6}$alkyl.

29. The compound according to claim 28, wherein
$R^4$ is

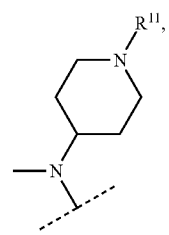

wherein
$R^{11}$ denotes $C_{1-6}$alkyl.

30. The compound according to claim 1, wherein
$R^6$ denotes chlorine.

31. The compound according to claim 1, wherein
$R^6$ denotes fluorine.

32. The compound or a pharmaceutically acceptable salt thereof—according to claim 1 selected from among:

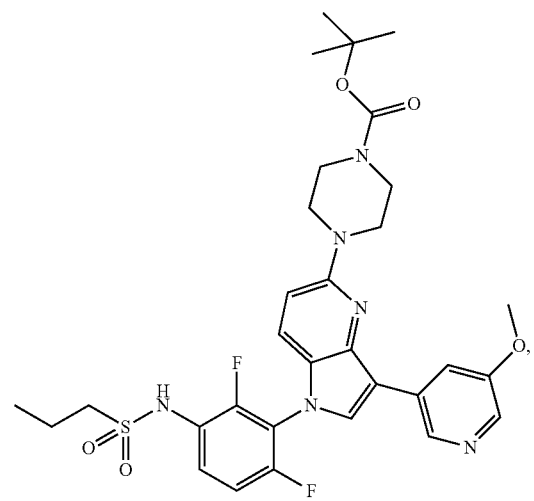

I-1

-continued
I-2
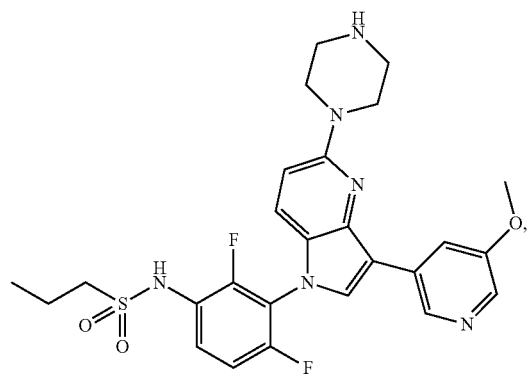
I-3
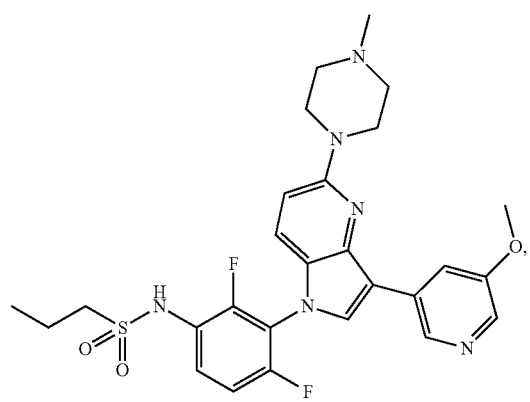
I-4
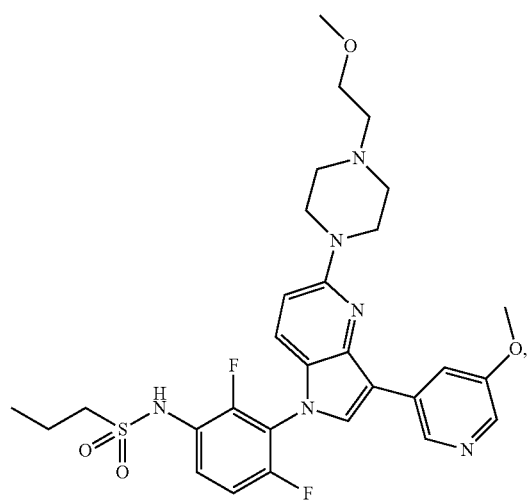
-continued
I-5
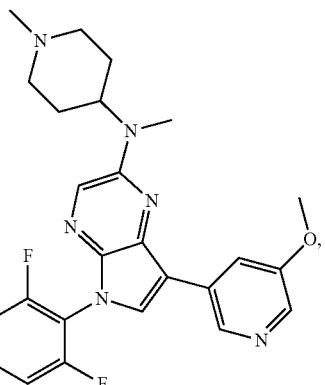
I-6
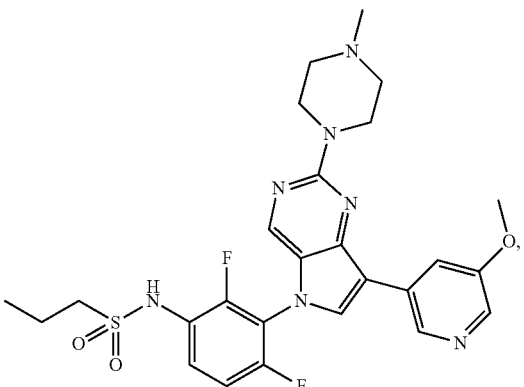
I-7
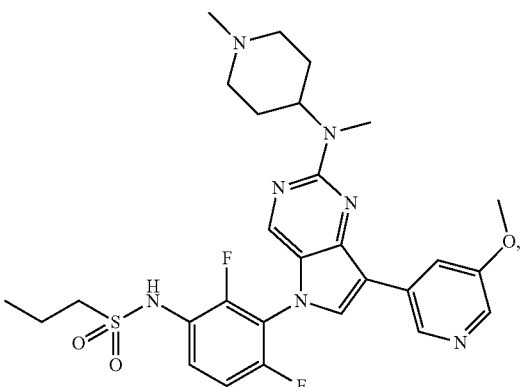
I-8
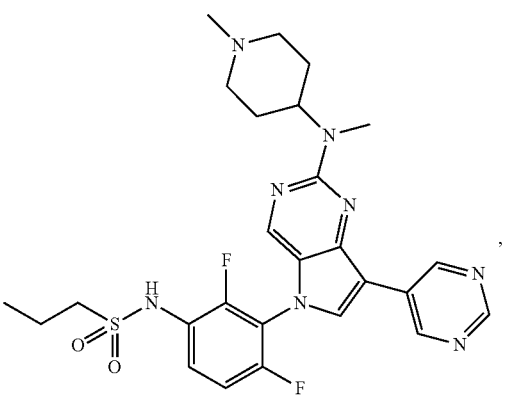

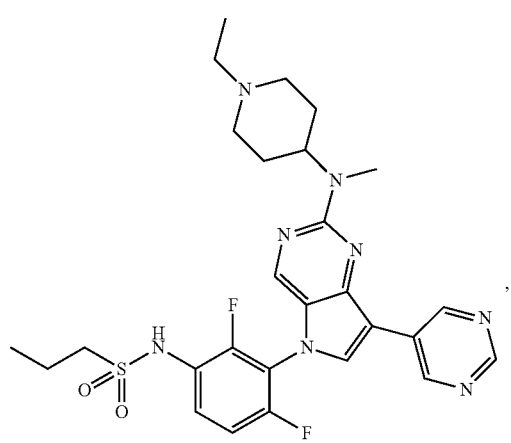
I-9
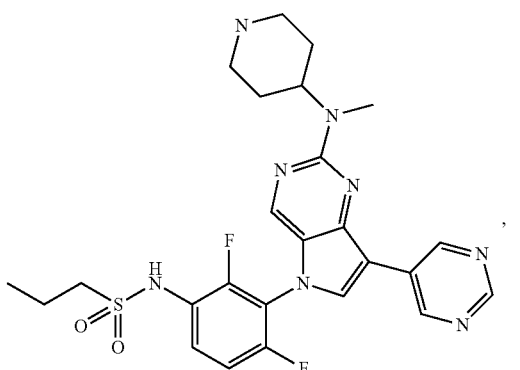
I-12
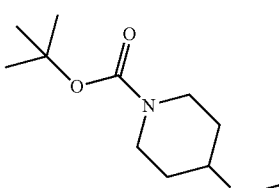
I-10
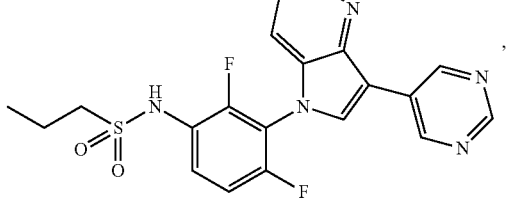
I-13
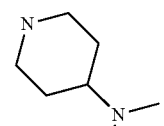
I-11
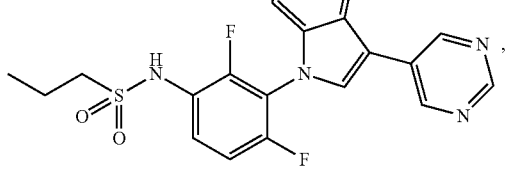
I-14
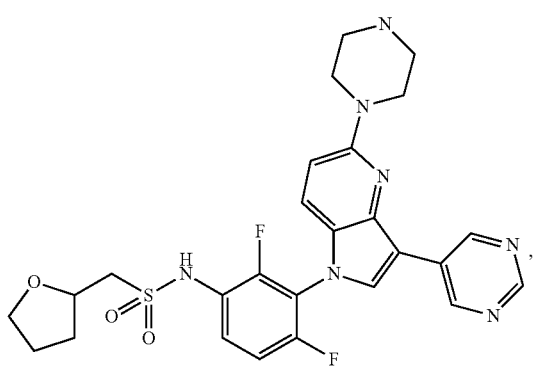
I-15

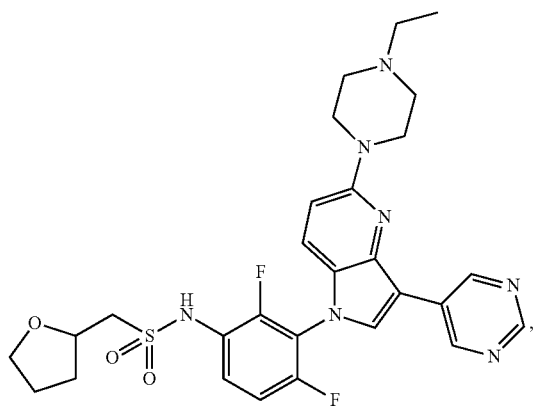
I-16
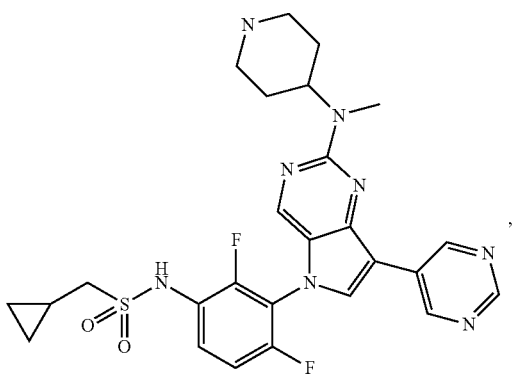
I-19
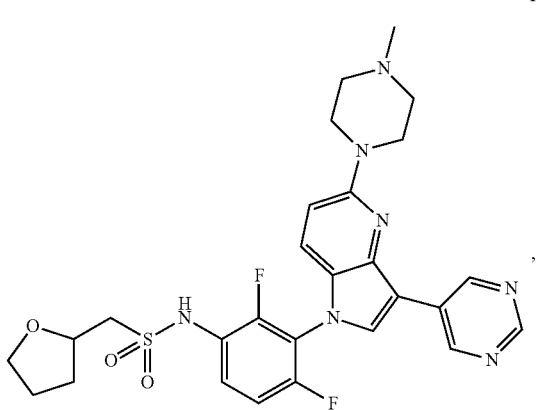
I-17
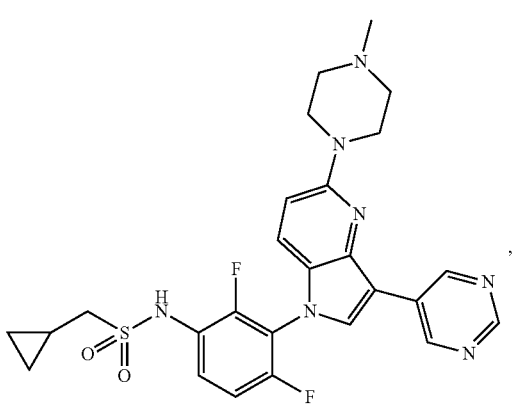
I-20
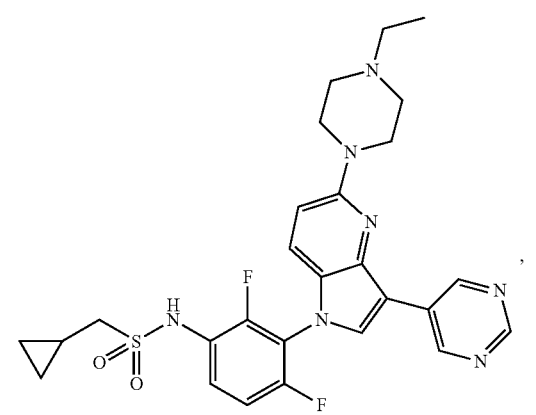
I-18
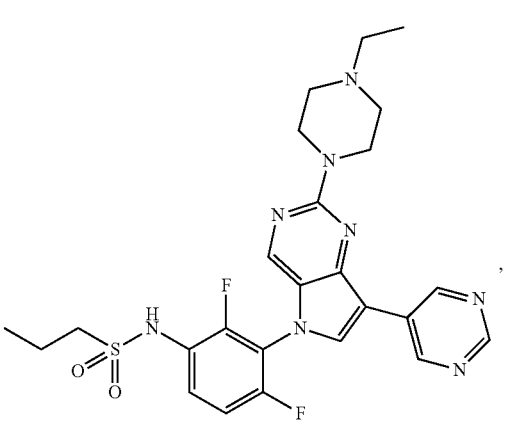
I-21

I-22
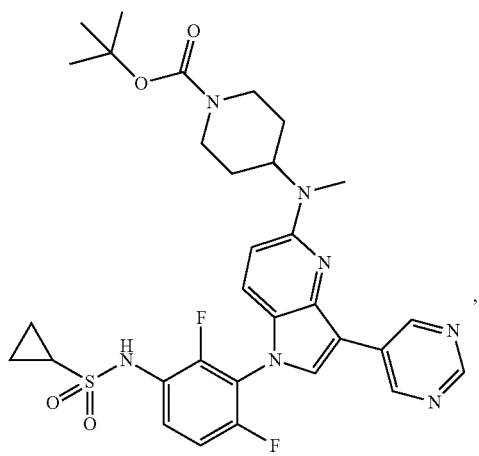
I-23
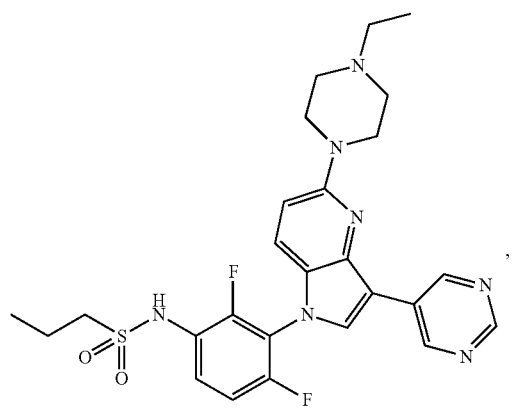
I-24
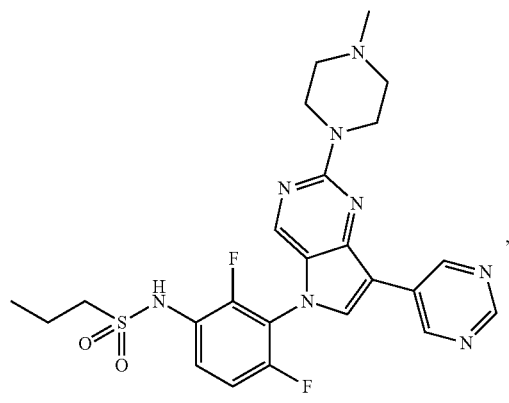
I-25
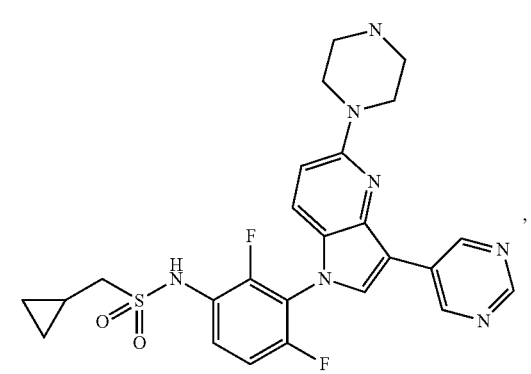
I-26
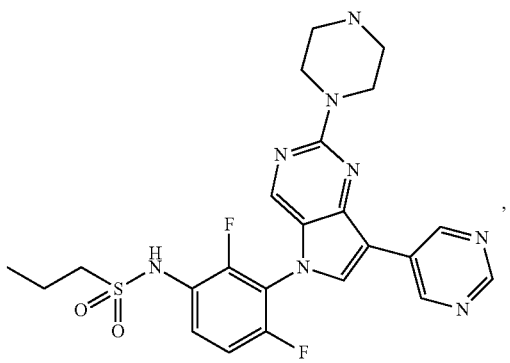
I-27
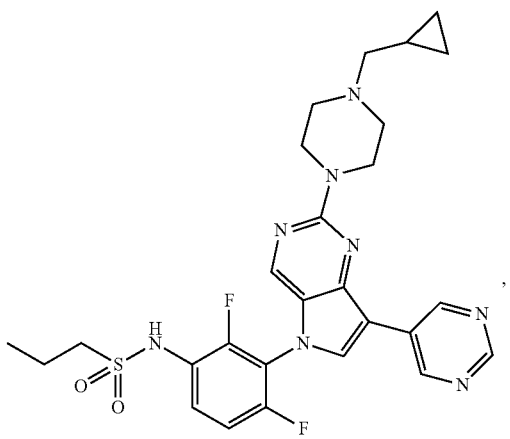
I-28
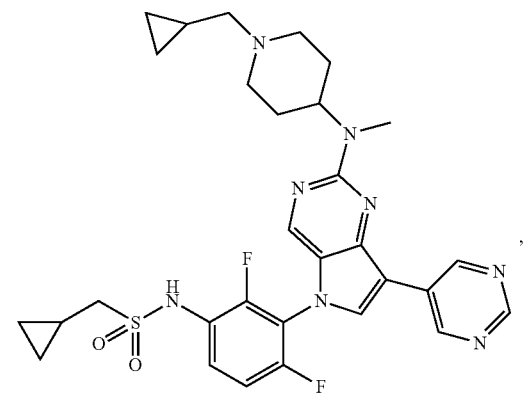
I-29
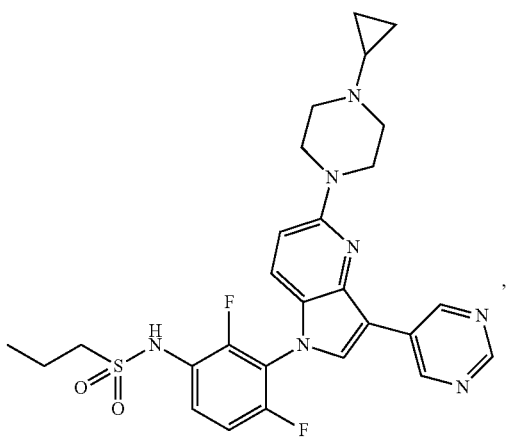

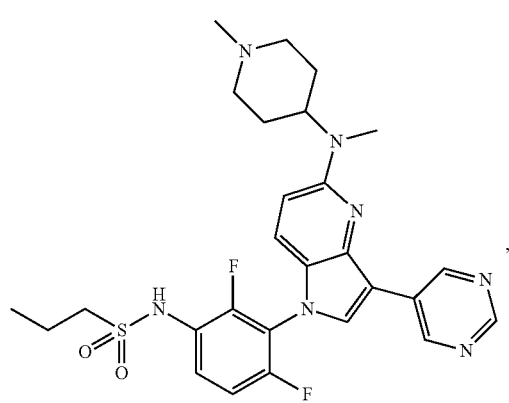
I-30
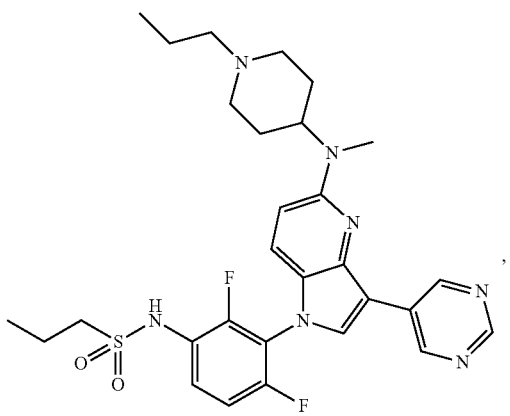
I-34
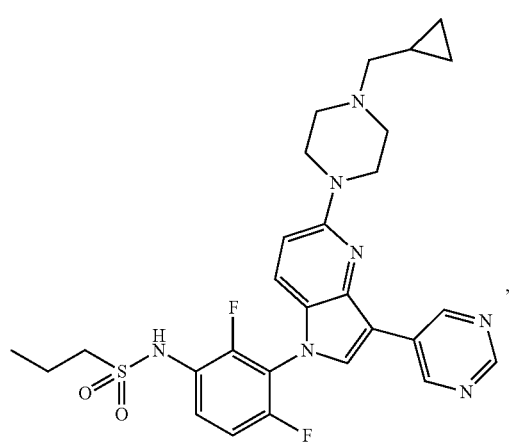
I-31
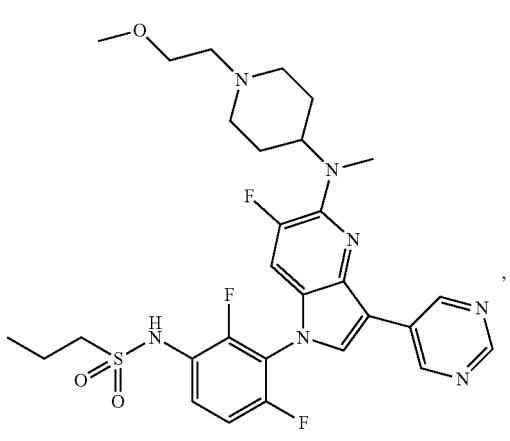
I-35
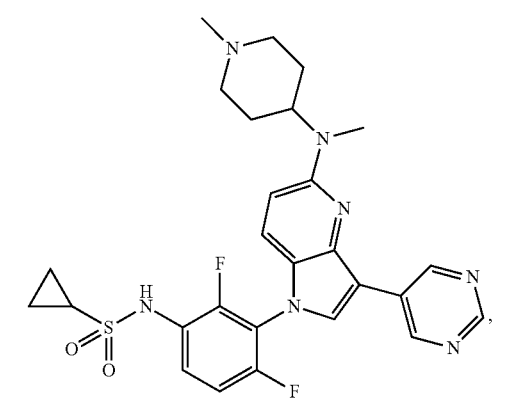
I-32
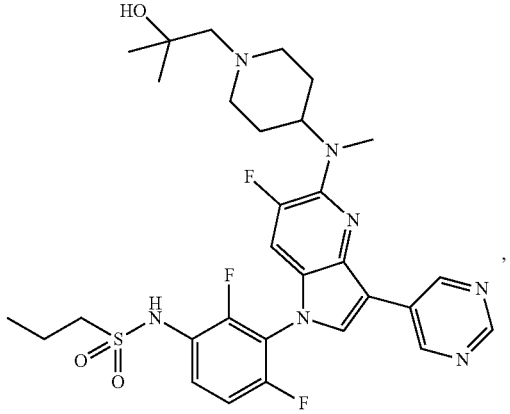
I-36
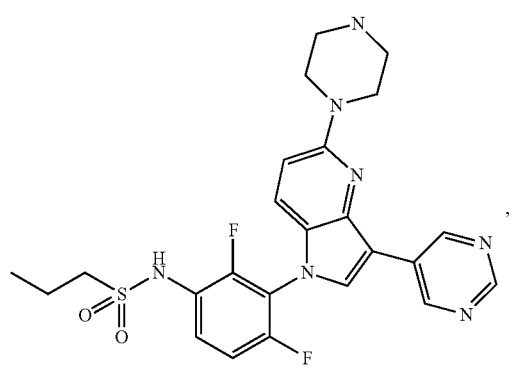
I-33
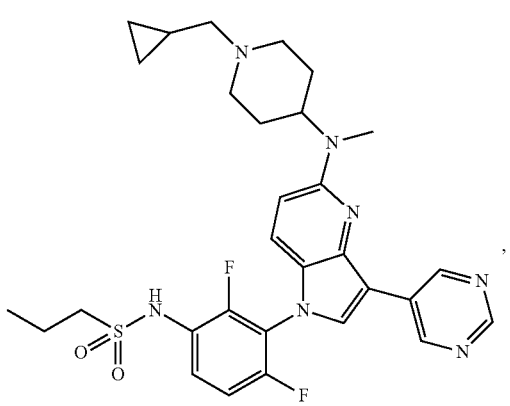
I-37

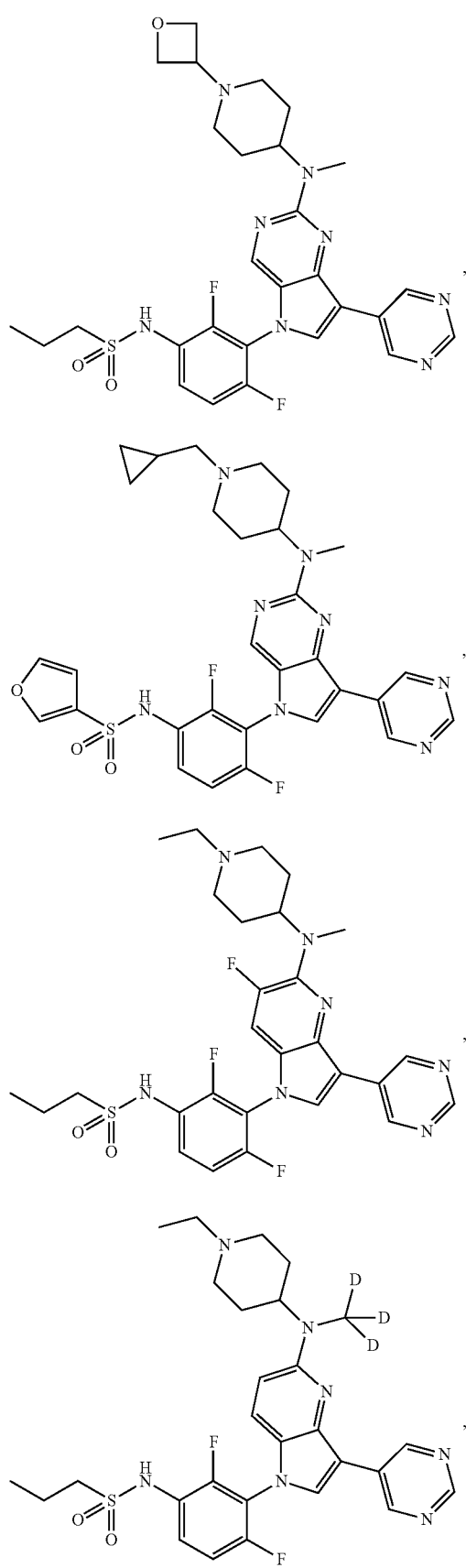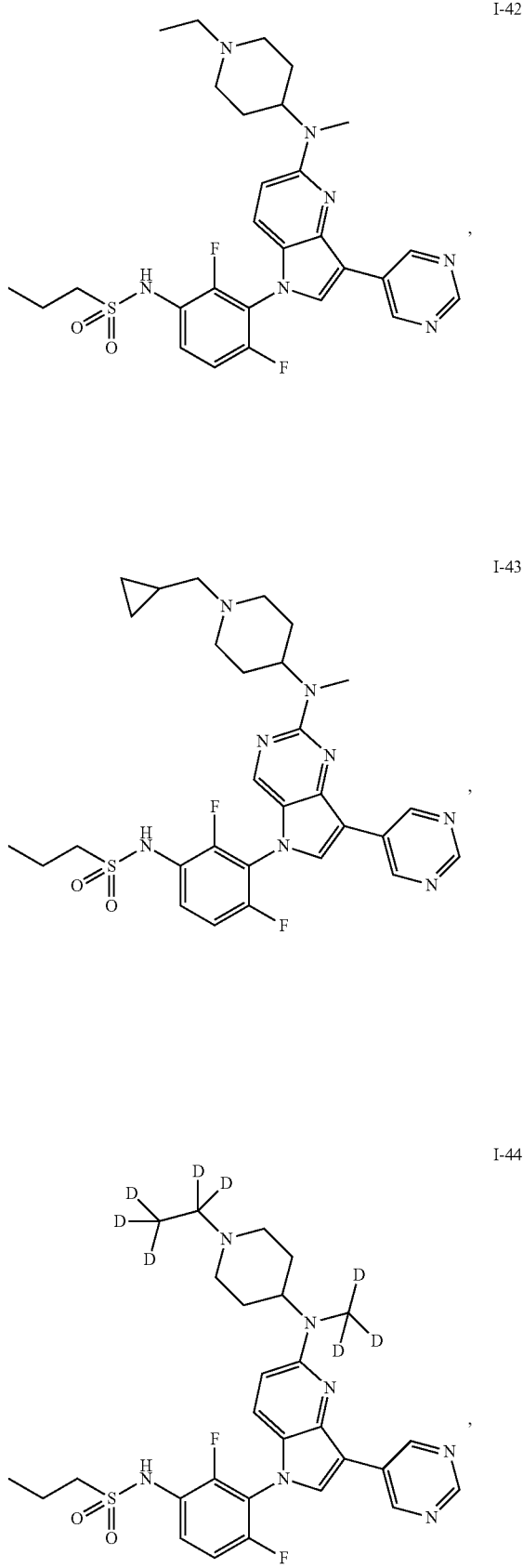

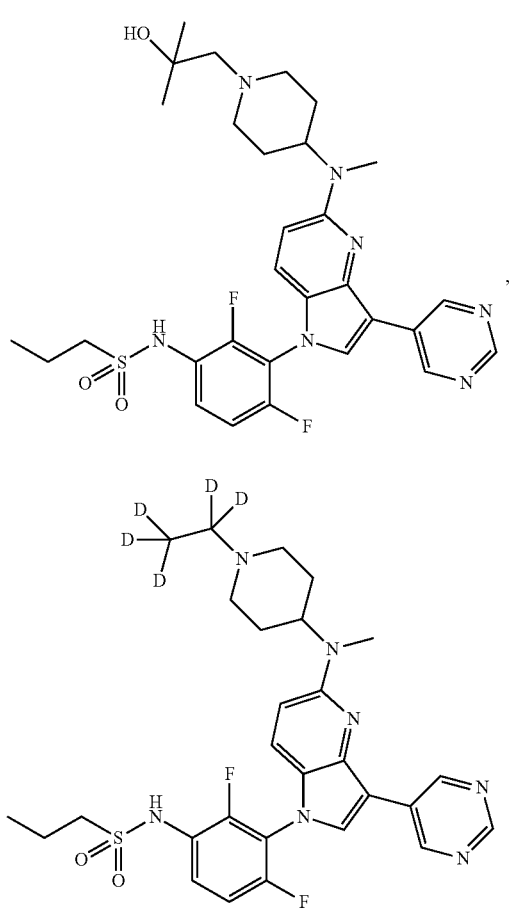

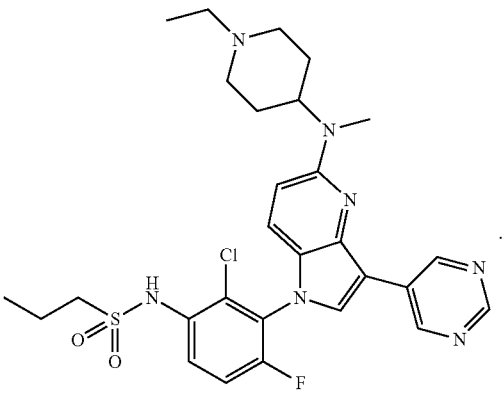

33. A pharmaceutical composition comprising a therapeutically effective amount of a compound of the formula (I) according to claim 1 or a pharmaceutically acceptable salt thereof—optionally in combination with conventional excipients and/or carriers.

34. The pharmaceutical composition according to claim 33 further comprising at least one other cytostatic or cytotoxic active substance, different from formula (I).

* * * * *